(12) United States Patent
Xiao

(10) Patent No.: US 8,841,269 B2
(45) Date of Patent: Sep. 23, 2014

(54) POLYNUCLEOTIDES FOR USE IN TREATING AND DIAGNOSING CANCERS

(75) Inventor: Gary Guishan Xiao, Rolling Hills Estates, CA (US)

(73) Assignee: Creighton University

( * ) Notice: Subject to any disclaimer, the term of this patent is extended or adjusted under 35 U.S.C. 154(b) by 285 days.

(21) Appl. No.: 13/033,056

(22) Filed: Feb. 23, 2011

(65) Prior Publication Data

US 2011/0224149 A1 Sep. 15, 2011

Related U.S. Application Data

(60) Provisional application No. 61/338,704, filed on Feb. 23, 2010.

(51) Int. Cl.
C12N 15/11 (2006.01)

(52) U.S. Cl.
USPC .......................................... 514/44 A

(58) Field of Classification Search
USPC ........................................ 514/44 A
See application file for complete search history.

(56) References Cited

U.S. PATENT DOCUMENTS

| | | | |
|---|---|---|---|
| 6,194,389 B1 | 2/2001 | Johnston et al. | |
| 6,617,162 B2 | 9/2003 | Dobie et al. | |
| 7,179,593 B1 | 2/2007 | Roy et al. | |
| 7,745,230 B2 | 6/2010 | Wang | |
| 2007/0092498 A1 | 4/2007 | Giordano | |
| 2007/0258895 A1 | 11/2007 | Wang | |
| 2008/0171715 A1* | 7/2008 | Brown et al. | 514/44 |
| 2009/0093026 A1 | 4/2009 | Dowdy et al. | |
| 2009/0163430 A1 | 6/2009 | Johnson et al. | |
| 2009/0263803 A1 | 10/2009 | Beaudenon et al. | |
| 2010/0016352 A1 | 1/2010 | Li et al. | |
| 2010/0029003 A1 | 2/2010 | Bartel et al. | |
| 2010/0257618 A1 | 10/2010 | Croce et al. | |
| 2010/0280099 A1 | 11/2010 | Elmen | |
| 2010/0310583 A1 | 12/2010 | Lieberman et al. | |

FOREIGN PATENT DOCUMENTS

WO WO2011/068865 A1 * 6/2011

OTHER PUBLICATIONS

Cochrane et al. Steroids 76, 2011, 1-10.*
Heneghan et al. Current Opinion in Pharmacology 2010, 10:543-550.*
Adams et al. "The micro-ribonucleic acid (miRNA) miR-206 targets the human estrogen receptor-alpha (ERalpha) and represses ERalpha messenger RNA and protein expression in breast cancer cell lines". 2007. *Mol Endocrinol.* 21:1132-1147.
Addis et al. "Generation of high-quality protein extracts from formalin-fixed, paraffin-embedded tissues". 2009. *Proteomics.* 9:3815-3823.
Barh et al. "MicroRNA let-7: an emerging next-generation cancer therapeutic". 2010. *Curr Oncol.* 17:70-80.
Berry et al. "Role of the two activating domains of the oestrogen receptor in the cell-type and promoter-context dependent agonistic activity of the anti-oestrogen 4-hydroxytamoxifen". 1990. *EMBO J.* 9(9):2811-2818.
Blenkiron et al. "MicroRNA expression profiling of human breast cancer identifies new markers of tumor subtype". 2007. *Genome Biol.* 8:R214.
Blenkiron et al., "miRNAs in cancer: approaches, aetiology, diagnostics and therapy". 2007. *Hum Mol Genet.* Apr. 15;16 Spec No. 1:R106-R113.
Castellano et al. "The estrogen receptor-{alpha}-induced microRNA signature regulates itself and its transcriptional response". 2009. *Proc Natl Acad Sci USA.* 106:15732-15737.
Clemons et al. "Estrogen and the risk of breast cancer". 2001, *N. Engl. J. Med.*, 344(4):276-285.
Cronin et al. "Measurement of gene expression in archival paraffin-embedded tissues: development and performance of a 92-gene reverse transcriptase-polymerase chain reaction assay". 2004. *Am J Pathol.* 164:35-42.
Dahiya et al. "MicroRNA expression and identification of putative miRNA targets in ovarian cancer". 2008. *PLoS One.* 3:e2436.
Eguchi et al. "Efficient siRNA delivery into primary cells by a peptide transduction domain-dsRNA binding domain fusion protein". 2009. *Nature Biotechnology.* 27:567-571.
Eisen et al. "Cluster analysis and display of genome-wide expression patterns". 1998. *Proc Natl Acad Sci USA.* 95:14863-14868.
Evans. "The steroid and thyroid hormone receptor superfamily". 1988. *Science.* 240(4854):889-895.
Flouriot et al., "Identification of a new isoform of the human estrogen receptor-alpha (hER-α) that is encoded by distinct transcripts and that is able to repress hER-α activation function 1". 2000. *EMBO J.* 19(17):4688-4700.
Gait. "Peptide-mediated cellular delivery of antisense oligonucleotides and their analogues". 2003. *Cell Mol Life Sci*, 60:1-10.

(Continued)

Primary Examiner — Brian Whiteman
(74) Attorney, Agent, or Firm — Advent, LLP

(57) ABSTRACT

The present invention provides methods for increasing sensitivity of cancer cells to an antiestrogen agent, such as a selective estrogen receptor modulator (SERM). The methods include administering to the subject a polynucleotide in an amount effective to increase the antiestrogen agent sensitivity of the cancer cells. The cancer cells may be estrogen receptor positive, such as ER-α66 positive or ER-α36 positive, prior to the administering. Also provided are methods for decreasing the amount of estrogen receptor present in a cancer cell, methods for determining whether antiestrogen agent sensitivity of cancer cells in a subject can be increased, methods for diagnosing whether a subject has, or is at risk for developing, cancer, and methods for identifying an agent that increases the amount of let-7 miRNA in a cell.

17 Claims, 27 Drawing Sheets

(56) References Cited

OTHER PUBLICATIONS

GenBank Accession No. BX640939. National Center for Biotechnology Information, National Library of Medicine, National Institutes of Health. "*Homo sapiens* mRNA; cDNA DKFZp686N23123 (from clone DKFZp686N23123)." Retrieved on Aug. 16, 2011. Retrieved from the internet: http://www.ncbi.nlm.nih.gov/nuccore/BX640939. 2 pages.
GenBank Accession No. AY390762. National Center for Biotechnology Information, National Library of Medicine, National Institutes of Health. "*Caenorhabditis elegans* microRNA let-7, complete sequence". Retrieved on Aug. 16, 2011. Retrieved from the internet http://www.ncbi.nlm.nih.gov/nuccore/AY390762. 1 page.
GenBank Accession No. AJ421724. National Center for Biotechnology Information, National Library of Medicine, National Institutes of Health. "*Homo sapiens* microRNA let-7a-1". Retrieved on Aug. 16, 2011. Retrieved from the internet http://www.ncbi.nlm.nih.gov/nuccore/AJ421724. 1 page.
GenBank Accession No. AJ421725. National Center for Biotechnology Information, National Library of Medicine, National Institutes of Health. *Homo sapiens* microRNA let-7a-2. Retrieved on Aug. 16, 2011. Retrieved from the internet http://www.ncbi.nlm.nih.gov/nuccore/AJ421725. 1 page.
GenBank Accession No. AJ421726. National Center for Biotechnology Information, National Library of Medicine, National Institutes of Health. *Homo sapiens* microRNA let-7a-3. Retrieved on Aug. 16, 2011. Retrieved from the internet http://www.ncbi.nlm.nih.gov/nuccore/AJ421726. 1 page.
GenBank Accession No. AJ421727. National Center for Biotechnology Information, National Library of Medicine, National Institutes of Health. "*Homo sapiens* microRNA let-7b". Retrieved on Aug. 16, 2011. Retrieved from the internet http://www.ncbi.nlm.nih.gov/nuccore/AJ421727. 1 page.
GenBank Accession No. AJ421728. National Center for Biotechnology Information, National Library of Medicine, National Institutes of Health. "*Homo sapiens* microRNA let-7c". Retrieved on Aug. 16, 2011. Retrieved from the internet http://www.ncbi.nlm.nih.gov/nuccore/AJ421728. 1 page.
GenBank Accession No. AJ421729. National Center for Biotechnology Information, National Library of Medicine, National Institutes of Health. "*Homo sapiens* microRNA let-7d". Retrieved on Aug. 16, 2011. Retrieved from the internet http://www.ncbi.nlm.nih.gov/nuccore/AJ421729. 1 page.
GenBank Accession No. AJ421730. National Center for Biotechnology Information, National Library of Medicine, National Institutes of Health. "*Homo sapiens* microRNA let-7e". Retrieved on Aug. 16, 2011. Retrieved from the internet http://www.ncbi.nlm.nih.gov/nuccore/AJ421730. 1 page.
GenBank Accession No. AJ421731. National Center for Biotechnology Information, National Library of Medicine, National Institutes of Health. "*Homo sapiens* microRNA let-7f-1". Retrieved on Aug. 16, 2011. Retrieved from the internet http://www.ncbi.nlm.nih.gov/nuccore/AJ421731. 1 page.
GenBank Accession No. AJ421732. National Center for Biotechnology Information, National Library of Medicine, National Institutes of Health. "*Homo sapiens* microRNA let-7f-2". Retrieved on Aug. 16, 2011. Retrieved from the internet http://www.ncbi.nlm.nih.gov/nuccore/AJ421732. 1 page.
GenBank Accession No. X03635. National Center for Biotechnology Information, National Library of Medicine, National Institutes of Health. "*Homo sapiens* mRNA for oestrogen receptor". Retrieved on Aug. 16, 2011. Retrieved from the internet http://www.ncbi.nlm.nih.gov/nuccore/X03635. 3 pages.
Gilad et al. "Serum microRNAs are promising novel biomarkers". 2008. *PLoS. One.* 3(9):e3418.
Gosden et al. "Localization of the human oestrogen receptor gene to chromosome 6q24----q27 by in situ hybridization". 1986, *Cytogenet Cell Genet.* 43(3-4):218-220.

Grosshans et al., "The temporal patterning microRNA let-7 regulates several transcription factors at the larval to adult transition in *C. elegans*". 2005. *Dev Cell.* 8:321-330.
Gunaratne. "Embryonic stem cell microRNAs: defining factors in induced pluripotent (iPS) and cancer (CSC) stem cells?". 2009. *Curr Stem Cell Res Ther.* 4:168-177.
Heneghan et al. "MicroRNAs as Novel Biomarkers for Breast Cancer". 2009. J Oncol. *J Oncol* doi:10.1155/2010/950201.
Heneghan et al. "Circulating microRNAs as novel minimally invasive biomarkers for breast cancer". 2010. *Ann. Surg.* 251(3):499-505.
Heo et al. "Linn Mediates the Terminal Uridylation of let-7 Precursor MicroRNA". 2008. *Molecular Cell.* 32:276-284.
Heo et al. "TUT4 in concert with Lin28 suppresses microRNA biogenesis through pre-microRNA uridylation". 2009. *Cell* 138:696-708.
Hossain et al. "Mir-17-5p regulates breast cancer cell proliferation by inhibiting translation of AIB1 mRNA". 2006. *Mol Cell Biol.* 26:8191-8201.
Hu et al. "MicroRNA-98 and let-7 confer cholangiocyte expression of cytokine-inducible Src homology 2-containing protein in response to microbial challenge". 2009. *J Immunol.* 183:1617-1624.
Hui et al. "Robust global micro-RNA profiling with formalin-fixed paraffin-embedded breast cancer tissues". 2009. *Lab Invest.* 89:597-606.
Iorio et al. "MicroRNA gene expression deregulation in human breast cancer". 2005. *Cancer Res.* 65(16):7065-7070.
Jacque et al. "Modulation of HIV-1 replication by RNA interference". 2002. *Nature.* 418:435-438.
Johnson et al. "RAS is regulated by the let-7 microRNA family". 2005. *Cell.* 120:635-647.
Kang et al. Involvement of estrogen receptor variant ER-α36, not GPR30, in nongenomic estrogen signaling. 2010. *Mol Endocrinol.* 24(4):709-721.
Kim et al. "HuR recruits let-7/RISC to repress c-Myc expression". 2009. *Genes Dev.* 23:1743-1748.
Kondo et al. "miR-206 Expression is down-regulated in estrogen receptor alpha-positive human breast cancer". 2008. *Cancer Res.* 68:5004-5008.
Kong et al. "MicroRNA-155 is regulated by the transforming growth factor beta/Smad pathway and contributes to epithelial cell plasticity by targeting RhoA". 2008. *Mol Cell Biol.* 28:6773-6784.
Kumar et al. "Suppression of non-small cell lung tumor development by the let-7 microRNA family". 2008. *Proc Natl Acad Sci USA* 105:3903-3908.2008.
Lau et al. "An abundant class of tiny RNAs with probable regulator roles in *Caenorhabditis elegans*". 2001. *Science.* 294(5543):858-862.
Lee et al. "An Extensive Class of Small RNAs in *Caenorhabditis elegans*". 2001. *Science.* 294:862-864.
Lee et al. "The tumor suppressor microRNA let-7 represses the HMGA2 oncogene". 2007. *Genes Dev.* 21:1025-1030.
Lee et al. ER-α36, a novel variant of ER-α, is expressed in ER-positive and -negative human breast carcinomas. *Anticancer Res.* 28:479-483, 2008.
Leivonen et al. "Protein lysate microarray analysis to identify microRNAs regulating estrogen receptor signaling in breast cancer cell lines". 2009. *Oncogene.* 28(44):3926-3936.
Li et al. "Plasma Membrane Localization and Function of the Estrogen Receptor a Variant (ER46) in Human Endothelial Cells". 2003. *Proc Natl Acad Sci USA.* 100:4807-4812.
Li et al. "Comparison of miRNA expression patterns using total RNA extracted from matched samples of formalin-fixed paraffin-embedded (FFPE) cells and snap frozen cells". 2007. *BMC Biotechnol.* 7:36.
Lim et al. "Vertebrate microRNA genes". 2003. *Science.* 299(5612):1540.
Lim et al. "The microRNAs of *Caenorhabditis elegans*". 2003. *Genes & Development.* 17:991-1008.
Lindsay et al. "Peptide-mediated cell delivery: application in protein target validation". 2002. *Curr Opin Pharmacol,* 2:587-594.

(56) References Cited

OTHER PUBLICATIONS

Liu et al. "MicroRNA Expression Profiling Outperforms mRNA Expression Profiling in Formalin-fixed Paraffin-embedded Tissues". 2009. *Int J Clin Exp Pathol.* 2:519-527.
Ma et al. "Tumour invasion and metastasis initiated by microRNA-10b in breast cancer". 2007. *Nature.* 449:682-688.
Marques et al. Research Letter. "A structural basis for discriminating between self and nonself double-stranded RNAs in mammaliam cells". 2006. *Nat. Biotech.* 24:559-565.
Mattie et al. "Optimized high-throughput microRNA expression profiling provides novel biomarker assessment of clinical prostate and breast cancer biopsies". 2006. *Mol Cancer.* 5:24.
Mayr et al. "Disrupting the pairing between let-7 and Hmga2 enhances oncogenic transformation". 2007. *Science.* 315:1576-1579.
Medina et al. "microRNAs and cancer: an overview". 2008. *Cell Cycle.* 7:2485-2492.
Michael et al. "Reduced accumulation of specific microRNAs in colorectal neoplasia". 2003. *Mol Cancer Res.* 1:882-891.
Mitchell et al. "Circulating microRNAs as stable blood-based markers for cancer detection". 2008. *Proc Natl Acad Sci USA.* 29:105:10513-10518.
Ng et al. "MicroRNAs as New Players for Diagnosis, Prognosis and Therapeutic Targets in Breast Cancer". 2009. *J Oncol,* doi:10.1155/2009/305420.
Ng et al. "Differential expression of microRNAs in plasma of patients with colorectal cancer: a potential marker for colorectal cancer screening". 2009. *GUT.* 58(10):1375-1381. Doi: 10. 1136/gut.2008. 167817.
Oxelmark et al. "The cochaperone p23 differentially regulates estrogen receptor target genes and promotes tumor cell adhesion and invasion". 2006. *Mol Cell Biol.* 26:5205-5213.
Pandey et al. "miR-22 inhibits estrogen signaling by directly targeting the estrogen receptor alpha mRNA". 2009. *Mol Cell Biol.* 29:3783-3790.
Pasquinelli et al. "Conservation of the sequence and temporal expression of let-7 heterochronic regulator RNA". 2000. *Nature.* 408:86-89.
Roush et al. "The let-7 family of microRNAs". 2008. *Trends Cell Biol.* 18:505-516.
Sambrook et al. 1989. Eds., $2^{nd}$ edition, Cold Spring Harbor Laboratory Press. Chapter 7. Title Page, Copyright Page, Table of Contents, and Chapter 7.
Sambrook et al. 1989. Eds., $2^{nd}$ edition, Cold Spring Harbor Laboratory Press. Title Page, Copyright Page, Table of Contents, and Chapter 10.
Sambrook et al. 1989. Eds., $2^{nd}$ edition, Cold Spring Harbor Laboratory Press. Title Page, Copyright Page, Table of Contents, and Chapter 11.
Schickel et al. "MicroRNAs: key players in the immune system, differentiation, tumorigenesis and cell death". 2008. *Oncogene.* 27:5959-5974.
Schultz et al. "MicroRNA let-7b targets important cell cycle molecules in malignant melanoma cells and interferes with anchorage-independent growth". 2008. *Cell Res.* 18:549-557.
Scott et al. "Coordinate suppression of ERBB2 and ERBB3 by enforced expression of micro-RNA miR-125a or miR-125b". 2007 *J Biol Chem.* 282:1479-1486.
Segars et al. "Estrogen action and cytoplasmic signaling cascades. Part I: Membrane-associated signaling complexes". 2002. *Trends Endocrinol. Metab.* 13:349-354.
Sempere et al. "Altered MicroRNA expression confined to specific epithelial cell subpopulations in breast cancer". 2007. *Cancer Res.* 67:11612-11620.
Shi et al. "Expression of ER-α36, a novel variation of estrogen receptor α, and resistance to tamoxifen treatment in breast cancer". 2009. *J Clin Oncol.* 27:3423-3429.
Sui et al. "A DNA vector-based RNAi technology to suppress gene suppression in mammalian cells". 2002. *Proc Natl Acad Sci USA.* 99:5515-5520.
Takamizawa et al. "Reduced expression of the let-7 microRNAs inhuman lung cancers in associate with shortened postoperative survival". 2004. *Cancer Res.* 64:3753-3756.
Torrisani et al. "Enjoy the Silience: The Story of let-7 MicroRNA and Cancer". 2007. *Current Genomics.* (4):229-233.
Valastyan et al. "A pleiotropically acting microRNA, miR-31, inhibits breast cancer metastasis". 2009. *Cell.* 137:1032-1046.
Vella et al. 2005., In:Wormbook, ed. The *C. elegans* Research Community, WormBook, doi/10.1895/wormbook.1.26.1.
Vranic et al. "ER-α36, a novel isoform of ER-α66, is commonly over-expressed in apocrine and adenoid cystic carcinomas of the breast", 2010. *J. Clin Pathol.* 64:54-57 (originally published online Nov. 2, 2010). Doi: 10.1136/jcp.2010.082776.
Wadia et al. "Protein transduction technology". 2002. *Curr Opin Biotechnol.* 13:52-56.
Wang et al. "Identification, cloning, and expression of human estrogen receptor-α36, a novel variant of human estrogen receptor-α66". 2005. *Biochem. Biophys. Res. Commun.* 336:1023-1027.
Wang et al. "A variant of estrogen receptor-{alpha}, hER-{alpha}36: transduction of estrogen- and antiestrogen-dependent membrane-initiated mitogenic signaling". 2006. *Proc Natl Acad Sci USA.* 103:9063-9068.
Wang et al. "miR-145 inhibits breast cancer cell growth through RTKN". 2009. *Int J Oncol.* 34:1461-1466.
Wang et al. "Circulating microRNAs, potential biomarkers for drug-induced liver injury". 2009. *Proc Natl Acad Sci USA.* 106(11):4402-4407.
Wang et al. "Correlation and quantitation of microRNA aberrant expression in tissues and sera from patients with breast tumor". 2010. *Gynecol Oncol.* 119(3):586-593.
Weihua et al. "Update on estrogen signaling". 2003. *FEBS Lett.* 546:17-24.
Xi et al. "Systematic analysis of microRNA expression of RNA extracted from fresh frozen and formalin-fixed paraffin-embedded samples". 2007. *RNA.* 13:1668-1674.
Yan et al. "MicroRNA miR-21 overexpression inhuman breast cancer is associated with advanced clinical stage, lymph node metastatis and patient poor prognosis". 2008. *RNA.* 14:2348-2360.
Yu et al. "let-7 regulates self renewal and tumorigenicity of breast cancer cells". 2007. *Cell.* 131:1109-1123.
Yu et al. "The immunohistochemically "ER-negative, PR-negative, HER2-negative, CK5/6-negative, and HER1-negative" subgroup is not a surrogate for the normal-like subtype in breast cancer". 2009. *Breast Cancer Res. Treat.* 118(3):661-663.
Zhang et al. "An array-based analysis of microRNA expression comparing matched frozen and formalin-fixed paraffin-embedded human tissue samples". 2008. *J Mol Diag.* 10:513-519.
Zhang et al. "Inhibition of Protein Phosphorylation in MIA Pancreatic Cancer Cells: Confluence of Metabolic and Signaling Pathways". 2010. *J Proteome Res.* 9(2):980-989.
Zhang et al. "A positive feedback loop of ER-α36/EGFR promotes malignant growth of ER-negative breast cancer cells", 2011. *Oncogene.* 30(7):770-780.
Zhao et al. "MicroRNA-221/222 negatively regulates estrogen receptor alpha and is associated with tamoxifen resistance in breast cancer". 2008. *J Biol Chem.* 283:31079-31086.
Zhao et al. PreClinical Study. "Let-7 family miRNAs regulate estrogen receptor alpha signaling in estrogen receptor positive breast cancer". 2010. *Breast Cancer Res. Treat.* DOI 10.1007/s10549-010-0972-2. Published online: Jun. 10, 2010. 12 pgs.
Zhao et al. "Let-7 microRNAs induce tamoxifen sensitivity by down-regulation of estrogen receptor alpha signaling in breast cancer". *Molecular Medicine.* Jul. 27, 2011. Doi: 10.2119/molmed.2010. 00225. (Epub ahead of print).44 pages total (with Abstract).
Zhu et al. "MicroRNA-21 targets tumor suppressor genes in invasion and metastasis". 2008. *Cell Res.* 18:350-359.
Zou et al. "Estrogen receptor-alpha (ER-α) suppresses expression of its variant ER-α36". 2009. *FEBS Lett.* 583:1368-1374.
Zuker et al. 1999. In:RNA Biochemistry and Biotechnology, Barciszewski and Clark, eds., NATO ASI Series, Kluwer Academic Publishers. pp. 11-43.

\* cited by examiner

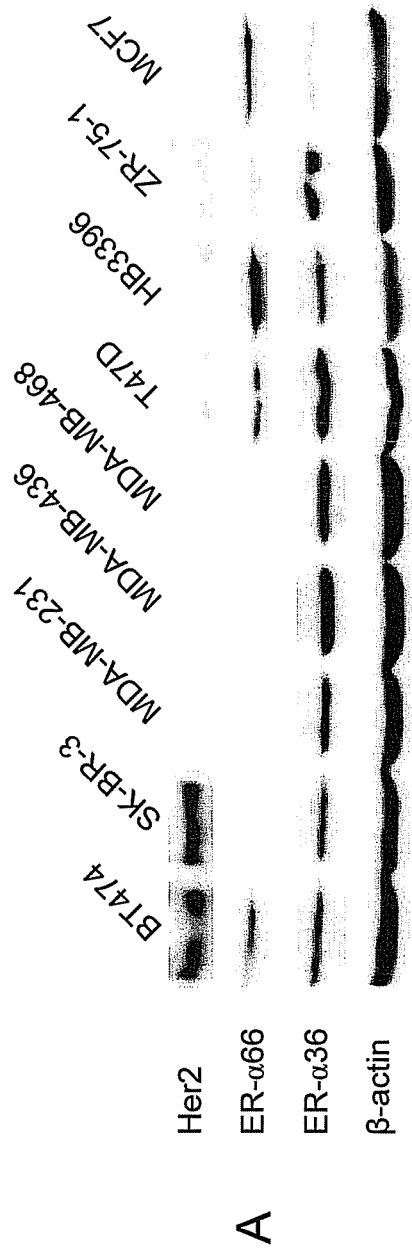
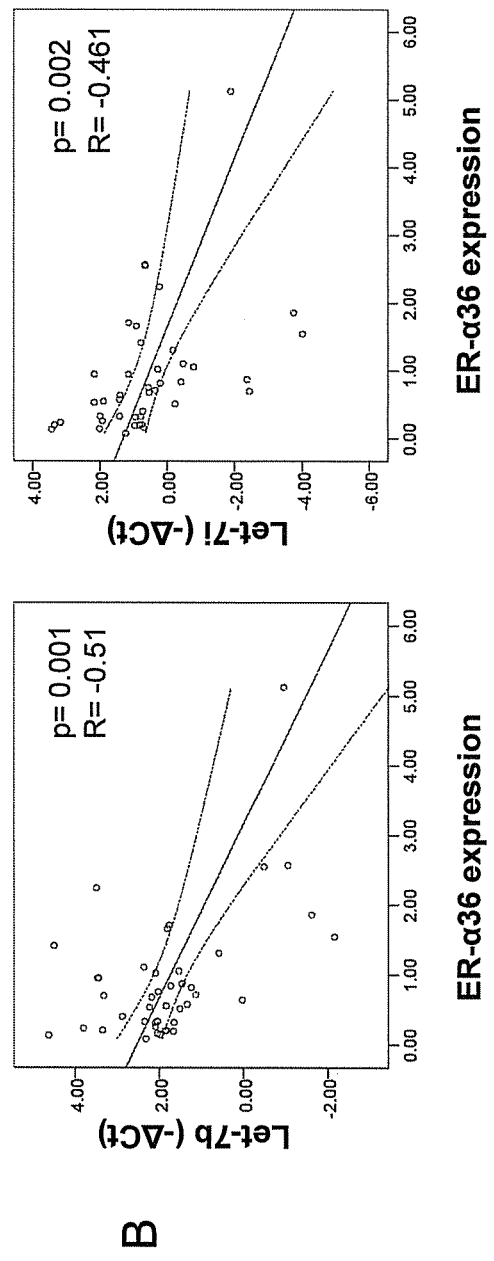
FIGURE 12

FIGURE 18

SEQ ID NO:1

```
GAGTTGTGCCTGGAGTGATGTTTAAGCCAATGTCAGGGCAAGGCAACAGTCCCTGGCCGTCCTCCAGCAC
CTTTGTAATGCATATGAGCTCGGGAGACCAGTACTTAAAGTTGGAGGCCCGGGAGCCCAGGAGCTGGCGG
AGGGCGTTCGTCCTGGGAGCTGCACTTGCTCCGTCGGGTCGCCGGCTTCACCGGACCGCAGGCTCCCGGG
GCAGGGCCGGGGCCAGAGCTCGCGTGTCGGCGGGACATGCGCTGCGTCGCCTCTAACCTCGGGCTGTGCT
CTTTTTCCAGGTGGCCCGCCGGTTTCTGAGCCTTCTGCCCTGCGGGGACACGGTCTGCACCCTGCCCGCG
GCCACGGACCATGACCATGACCCTCCACACCAAAGCATCTGGGATGGCCCTACTGCATCAGATCCAAGGG
AACGAGCTGGAGCCCCTGAACCGTCCGCAGCTCAAGATCCCCTGGAGCGGCCCCTGGGCGAGGTGTACC
TGGACAGCAGCAAGCCCGCCGTGTACAACTACCCCGAGGGCGCCGCCTACGAGTTCAACGCCGCGGCCGC
CGCCAACGCGCAGGTCTACGGTCAGACCGGCCTCCCCTACGGCCCCGGGTCTGAGGCTGCGGCGTTCGGC
TCCAACGGCCTGGGGGGTTTCCCCCCACTCAACAGCGTGTCTCCGAGCCCGCTGATGCTACTGCACCCGC
CGCCGCAGCTGTCGCCTTTCCTGCAGCCCACGGCCAGCAGGTGCCCTACTACCTGGAGAACGAGCCCAG
CGGCTACACGGTGCGCGAGGCCGGCCCGCCGGCATTCTACAGGCCAAATTCAGATAATCGACGCCAGGGT
GGCAGAGAAAGATTGGCCAGTACCAATGACAAGGGAAGTATGGCTATGGAATCTGCCAAGGAGACTCGCT
ACTGTGCAGTGTGCAATGACTATGCTTCAGGCTACCATTATGGAGTCTGGTCCTGTGAGGGCTGCAAGGC
CTTCTTCAAGAGAAGTATTCAAGGACATAACGACTATATGTGTCCAGCCACCAACCAGTGCACCATTGAT
AAAAACAGGAGGAAGAGCTGCCAGGCCTGCCGGCTCCGCAAATGCTACGAAGTGGGAATGATGAAAGGTG
GGATACGAAAAGACCGAAGAGCAGGGAGAATGTTGAAACACAAGCGCCAGAGAAGATGATGGGGAGGGCAG
GGGTGAAGTGGGGTCTGCTGGAGACATGAGAGCTGCCAACCTTTGGCCAAGCCCGCTCATGATCAAACGC
TCTAAGAAGAACAGCCTGGCCTTGTCCCTGACGGCCGACCAGATGGTCAGTGCCTTGTTGGATGCTGAGC
CCCCCATACTCTATTCCGAGTATGATCCTACCAGACCCTTCAGTGAAGCTTCCATGATGGCTTACTGAC
CAACCTGGCAGACAGGGAGCTGGTTCACATGATCAACTGGGCGAAGAGGGTGCCAGGCTTTGTGGATTTG
ACCCTCCATGATCAGGTCCACCTTCTAGAATGTGCCTGGCTAGAGATCCTGATGATTGGTCTCGTCTGGC
GCTCCATGGAGCACCCAGTGAAGCTACTGTTTGCTCCTAACTTGCTCTTGGACAGGAACCAGGGAAAATG
TGTAGAGGGCATGGTGGAGATCTTCGACATGCTGCTGGCTACATCATCTCGGTTCCGCATGATGAATCTG
CAGGGAGAGGAGTTTGTGTGCCTCAAATCTATTATTTTGCTTAATTCTGGAGTGTACACATTTCTGTCCA
GCACCCTGAAGTCTCTGGAAGAGAAGGACCATATCCACCGAGTCCTGGACAAGATCACAGACACTTTGAT
CCACCTGATGGCCAAGGCAGGCCTGACCCTGCAGCAGCAGCACCAGCGGCTGGCCCAGCTCCTCCTCATC
CTCTCCCACATCAGGCACATGAGTAACAAAGGCATGGAGCATCTGTACAGCATGAAGTGCAAGAACGTGG
TGCCCCTCTATGACCTGCTGCTGGAGATGCTGGACGCCCACCGCCTACATGCGCCCACTAGCCGTGGAGG
GGCATCCGTGGAGGAGACGGACCAAAGCCACTTGGCCACTGCGGGCTCTACTTCATCGCATTCCTTGCAA
AAGTATTACATCACGGGGGAGGCAGAGGGTTTCCCTGCCACAGTCTGAGAGCTCCCTGGCTCCCACACGG
TTCAGATAATCCCTGCTGCATTTTACCCTCATCATGCACCACTTTAGCCAAATTCTGTCTCCTGCATACA
CTCCGGCATGCATCCAACACCAATGGCTTTCTAGATGAGTGGCCATTCATTTGCTTGCTCAGTTCTTAGT
GGCACATCTTCTGTCTTCTGTTGGGAACAGCCAAAGGGATTCCAAGGCTAAATCTTTGTAACAGCTCTCT
TTCCCCCTTGCTATGTTACTAAGCGTGAGGATTCCCGTAGCTCTTCACAGCTGAACTCAGTCTATGGGTT
GGGGCTCAGATAACTCTGTGCATTTAAGCTACTTGTAGAGACCCAGGCCTGGAGAGTAGACATTTTGCCT
CTGATAAGCACTTTTTAAATGGCTCTAAGAATAAGCCACAGCAAAGAATTTAAAGTGGCTCCTTTAATTG
GTGACTTGGAGAAAGCTAGGTCAAGGGTTTATTATAGCACCCTCTTGTATTCCTATGGCAATGCATCCTT
TTATGAAAGTGGTACACCTTAAAGCTTTTATATGACTGTAGCAGAGTATCTGGTGATTGTCAATTCACTT
CCCCCTATAGGAATACAAGGGGCCACACAGGGAAGGCAGATCCCCTAGTTGGCCAAGACTTATTTTAACT
TGATACACTGCAGATTCAGAGTGTCCTGAAGCTCTGCCTCTGGCTTTCCGGTCATGGGTTCCAGTTAATT
CATGCCTCCCATGGACCTATGGAGAGCAACAAGTTGATCTTAGTTAAGTCTCCCTATATGAGGGATAAGT
TCCTGATTTTTGTTTTTATTTTTGTGTTACAAAAGAAAGCCCTCCCTCCCTGAACTTGCAGTAAGGTCAG
CTTCAGGACCTGTTCCAGTGGGCACTGTACTTGGATCTTCCCGGCGTGTGTGTGCCTTACACAGGGGTGA
ACTGTTCACTGTGGTGATGCATGATGAGGGTAAATGGTAGTTGAAAGGAGCAGGGCCCTGGTGTTGCAT
```

FIGURE 18 CONT'D

SEQ ID NO:1 CONT'D

```
TTAGCCCTGGGGCATGGAGCTGAACAGTACTTGTGCAGGATTGTTGTGGCTACTAGAGAACAAGAGGGAA
AGTAGGGCAGAAACTGGATACAGTTCTGAGCACAGCCAGACTTGCTCAGGTGGCCCTGCACAGGCTGCAG
CTACCTAGGAACATTCCTTGCAGACCCCGCATTGCCTTTGGGGGTGCCCTGGGATCCCTGGGGTAGTCCA
GCTCTTATTCATTTCCCAGCGTGGCCCTGGTTGGAAGAAGCAGCTGTCAAGTTGTAGACAGCTGTGTTCC
TACAATTGGCCCAGCACCCTGGGGCACGGGAGAAGGGTGGGGACCGTTGCTGTCACTACTCAGGCTGACT
GGGGCCTGGTCAGATTACGTATGCCCTTGGTGGTTTAGAGATAATCCAAAATCAGGGTTTGGTTTGGGGA
AGAAAATCCTCCCCCTTCCTCCCCCGCCCCGTTCCCTACCGCCTCCACTCCTGCCAGCTCATTTCCTTCA
ATTTCCTTTGACCTATAGGCTAAAAAAGAAAGGCTCATTCCAGCCACAGGGCAGCCTTCCCTGGGCCTTT
GCTTCTCTAGCACAATTATGGGTTACTTCCTTTTTCTTAACAAAAAAGAATGTTTGATTTCCTCTGGGTG
ACCTTATTGTCTGTAATTGAAACCCTATTGAGAGGTGATGTCTGTGTTAGCCAATGACCCACGTAGCTGC
TCGGGCTTCTCTTGGTATGTCTTGTTTGGAAAAGTGGATTTCATTCATTTCTGATTGTCCAGTTAAGTGA
TCACCAAAGGACTGAGAATCTGGGAGGGCAAAAAAAAAAAAAAAGTTTTTATGTGCACTTAAATTTGGG
GACAATTTTATGTATCTGTGTTAAGGATATGCTTAAGAACATAATTCTTTTGTTGCTGTTTGTTTAAGAA
GCACCTTAGTTTGTTTAAGAAGCACCTTATATAGTATAATATATATTTTTTTGAAATTACATTGCTTGTT
TATCAGACAATTGAATGTAGTAATTCTGTTCTGGATTTAATTTGACTGGGTTAACATGCAAAAACCAAGG
AAAAATATTTAGTTTTTTTTTTTTTTTTGTATACTTTTCAAGCTACCTTGTCATGTATACAGTCATTTA
TGCCTAAAGCCTGGTGATTATTCATTTAAATGAAGATCACATTTCATATCAACTTTTGTATCCACAGTAG
ACAAAATAGCACTAATCCAGATGCCTATTGTTGGATATTGAATGACAGACAATCTTATGTAGCAAAGATT
ATGCCTGAAAAGGAAAATTATTCAGGGCAGCTAATTTTGCTTTTACCAAAATATCAGTAGTAATATTTTT
GGACAGTAGCTAATGGGTCAGTGGGTTCTTTTTAATGTTTATACTTAGATTTTCTTTTAAAAAAATTAAA
ATAAAACAAAAAAAATTTCTAGGACTAGACGATGTAATACCAGCTAAAGCCAAACAATTATACAGTGGAA
GGTTTTACATTATTCATCCAATGTGTTTCTATTCATGTTAAGATACTACTACATTTGAAGTGGGCAGAGA
ACATCAGATGATTGAAATGTTCGCCCAGGGGTCTCCAGCAACTTTGGAAATCTCTTTGTATTTTTACTTG
AAGTGCCACTAATGGACAGCAGATATTTTCTGGCTGATGTTCGTATTGGGTGTAGGAACATGATTTAAAA
AAAAAACTCTTGCCTCTGCTTTCCCCCACTCTGAGGCAAGTTAAAATGTAAAAGATGTGATTTATCTGGG
GGGCTCAGGTATGGTGGGGAAGTGGATTCAGGAATCTGGGCAATGGCAAATATATTAAGAAGAGTATTGA
AAGTATTTGGAGGAAAATGGTTAATTCTGGGTGTGCACCAAGGTTCAGTAGAGTCCACTTCTGCCCTGGA
GACCACAAATCAACTAGCTCCATTTACAGCCATTTCTAAAATGGCAGCTTCAGTTCTAGAGAAGAAGAA
CAACATCAGCAGTAAAGTCCATGGAATAGCTAGTGGTCTGTGTTTCTTTTCGCCATTGCCTAGCTTGCCG
TAATGATTCTATAATGCCATCATGCAGCAATTATGAGAGGCTAGGTCATCCAAAGAGAAGACCCTATCAA
TGTAGGTTGCAAAATCTAACCCCTAAGGAAGTGCAGTCTTTGATTTCATTTCCCTAGTAACCTTGCAGAT
ATGTTTAACCAAGCCATAGCCCATGCCTTTTGAGGGCTGAACAAATAAGGGACTTACTGATAATTTACTT
TTGATCACATTAAGGTGTTCTCACCTTGAAATCTTATACACTGAAATGGCCATTGATTTAGGCCACTGGC
TTAGAGTACTCCTTCCCCTGCATGACACTGATTACAAATACTTTCCTATTCATACTTTCCAATTATGAGA
TGGACTGTGGGTACTGGGAGTGATCACTAACACCATAGTAATGTCTAATATTCACAGGCAGATCTGCTTG
GGGAAGCTAGTTATGTGAAAGGCAAATAAAGTCATACAGTAGCTCAAAAGGCAACCATAATTCTCTTTGG
TGCAAGTCTTGGGAGCGTGATCTAGATTACACTGCACCATTCCCAAGTTAATCCCCTGAAAACTTACTCT
CAACTGGAGCAAATGAACTTTCGTCCCAAATATCCATCTTTTCAGTAGCGTTAATTATGCTCTGTTTCCA
ACTGCATTTCCTTTCCAATTGAATTAAAGTGTGGCCTCGTTTTTAGTCATTTAAAATTGTTTTCTAAGTA
ATTGCTGCCTCTATTATGGCACTTCAATTTTGCACTGTCTTTTGAGATTCAAGAAAAATTTCTATTCATT
TTTTTGCATCCAATTGTGCCTGAACTTTTAAAATATGTAAATGCTGCCATGTTCCAAACCCATCGTCAGT
GTGTGTGTTTAGAGCTGTGCACCCTAGAAACAACATACTTGTCCCATGAGCAGGTGCCTGAGACACAGAC
CCCTTTGCATTCACAGAGAGGTCATTGGTTATAGAGACTTGAATTAATAAGTGACATTATGCCAGTTTCT
GTTCTCTCACAGGTGATAAACAATGCTTTTGTGCACTACATACTCTTCAGTGTAGAGCTCTTGTTTTAT
GGGAAAAGGCTCAAATGCCAAATTGTGTTTGATGGATTAATATGCCCTTTTGCCGATGCATACTATTACT
GATGTGACTCGGTTTTGTCGCAGCTTTGCTTTGTTTAATGAAACACACTTGTAAACCTCTTTTGCACTTT
GAAAAAGAATCCAGCGGGATGCTCGAGCACCTGTAAACAATTTTCTCAACCTATTTGATGTTCAAATAAA
GAATTAAACT
```

FIGURE 18 CONT'D

SEQ ID NO:2

MTMTLHTKASGMALLHQIQGNELEPLNRPQLKIPLERPLGEVYL
DSSKPAVYNYPEGAAYEFNAAAAANAQVYGQTGLPYGPGSEAAAFGSNGLGGFPPLNS
VSPSPLMLLHPPPQLSPFLQPHGQQVPYYLENEPSGYTVREAGPPAFYRPNSDNRRQG
GRERLASTNDKGSMAMESAKETRYCAVCNDYASGYHYGVWSCEGCKAFFKRSIQGHND
YMCPATNQCTIDKNRRKSCQACRLRKCYEVGMMKGGIRKDRRGGRMLKHKRQRDDGEG
RGEVGSAGDMRAANLWPSPLMIKRSKKNSLALSLTADQMVSALLDAEPPILYSEYDPT
RPFSEASMMGLLTNLADRELVHMINWAKRVPGFVDLTLHDQVRLLECAWLEILMIGLV
WRSMEHPVKLLFAFNLLLDRNQGKCVEGMVEIFDMLLATSSRFRMMNLQGEEFVCLKS
IILLNSGVYTFLSSTLKSLEEKDHIHRVLDKITDTLIHLMAKAGLTLQQQHQRLAQLL
LILSHIRHMSNKGMEHLYSMKCKNVVPLYDLLLEMLDAHRLHAPTSRGGASVEETDQS
HLATAGSTSSHSLQKYYITGEAEGFPATV

FIGURE 19

SEQ ID NO:3

GGCTTAAAAATAATCTCCTGCCAGCCCAGTGACAAGCCTGTCCCACCCGGGGAGAATGCCCCGGAGTGGC
GTGCGGGTCAGCCAGGGTCTGCGCCTCGCAGCCACTGTGGAAGGAGCGCGGCCGGTCCAGGACACAGGAG
ACCACTTTGTGACTTCAATGGCGAAGGCCAAATTCAGATAATCGACGCCAGGGTGGCAGAGAAAGATTGG
CCAGTACCAATGACAAGGGAAGTATGGCTATGGAATCTGCCAAGGAGACTCGCTACTGTGCAGTGTGCAA
TGACTATGCTTCAGGCTACCATTATGGAGTCTGGTCCTGTGAGGGCTGCAAGGCCTTCTTCAAGAGAAGT
ATTCAAGGACATAACGACTATATGTGTCCAGCCACCAACCAGTGCACCATTGATAAAAACAGGAGGAAGA
GCTGCCAGGCCTGCCGGCTCCGCAAATGCTACGAAGTGGGAATGATGAAAGGTGGGATACGAAAAGACCG
AAGAGGAGGGAGAATGTTGAAACACAAGCGCCAGAGAGATGATGGGGAGGGCAGGGGTGAAGTGGGGTCT
GCTGGAGACATGAGAGCTGCCAACCTTTGGCCAAGCCCGCTCATGATCAAACGCTCTAAGAAGAACAGCC
TGGCCTTGTCCCTGACGGCCGACCAGATGGTCAGTGCCTTGTTGGATGCTGAGCCCCCATACTCTATTC
CGAGTATGATCCTACCAGACCCTTCAGTGAAGCTTCGATGATGGGCTTACTGACCAACCTGGCAGACAGG
GAGCTGGTTCACATGATCAACTGGGCGAAGAGGGTGCCAGGCTTTGTGGATTGACCCTCCATGATCAGG
TCCACCTTCTAGAATGTGCCTGGCTAGAGATCCTGATGATTGGTCTCGTCTGGCGCTCCATGGAGCACCC
AGGGAAGCTACTGTTTGCTCCTAACTTGCTCTTGGACAGGAACCAGGGAAAATGTGTAGAGGGCATGGTG
GAGATCTTCGACATGCTGCTGGCTACATCATCTCGGTTCCGCATGATGAATCTGCAGGGAGAGGAGTTTG
TGTGCCTCAAATCTATTCTTTTGCTTAATTCTGGTATCTCACATGTAGAAGCAAAGAAGAGAATCCTGAA
CTTGCATCCTAAAATATTTGGAAACAAGTGGTTTCCTCGTGTCTAAAGCCTCTGGTCATAAGGCCTCACA
GTATCCTGCAGATCATCAAATCCGTGTGTGGACGTGGGACATTTTGTTTTGAGGCAGTTACATGACCAT
GGGCAAGTGGATTGGTCTCTCTGGCCTTCAGTTTTCTCATTTGCAATGATTCAATGGTTTGCCTTAAAGT
GTCTTAAGAAGGATAGGATAGCTACCCACAAACTTTGGATCAAATTTTCTTCAAAACATCCTTCCCCTGA
CTTTAAAATATGCCCTGGCAACCAACACTCAACACCCGTAGCTAGATGAGTTATAACAGAGTGACTGAAG
AGAGCTCCCACAATTCCTAGTTATTAAATACCTGACTAATTTTCATTAGGAGACATTTAAGAACTTTAGT
GATGGGAAGATTTACATATATAATTGATAGTACAATCTGACAGAGCTGAATAGCTCCTGTTTGTCAACTG
TTAAATTCTTTGTGCAATTAGGTCAAAGATCAAGATCAAAACAAGGGCTGCCCATTGACCTGTTCACTCC
TGAGAAAAATGGCAAACCATTGAATCATAAATCATGACAGCCAAAATAATTTTAGGATATTAATGCACCC
CTCATCTTTGCAAGTGAGAAAACTGAAGGCCAGAGAGACTAATTTACTTGCCCATTTTTGATAAAAATGT
CACCATTTACAGAATGTGGACTCCTATGTTGGAGTCTGTTGAAGGACATGGCACATTTAACAGCATCAGA
GCATTTTTTATTAAAATTTAATTTGTGCATGACTTCTAATGCTGAAGAACGCCAAGCTAGGAAGAAGTCA
TGGGCTGAGATGGGGACAGAGAGAACACACAATATTCAGTGACTGTCCGTGCAGCTGGCTGCCCTTGAAA
ATATCCGAACTATCCACTGGGAAAATGCCTGTCCCCTTGGGGTAATTACCAGAGTTTCAACATGCCCAAA
GCTGCCTCATCTTCAGGGGGAACTTGTTCTAGCGATTTTAGTATCAAGAAGCTAATGGTCCCAGGGAAAG
GGTTATTTTTAATATTTAGCTACTGTGCTAAAAATCACCTAAGTTTCTAGAGTCTTGGGAAATTTCATAA
GGGAAAGAACAAAGGCAACTTGTTGACTACCCACTGGTCATTCTCCTCTGGTCTTATTACATACATGGAT
GCCAGTTTAGATTGTGTTTATATAGGAAAATTTAAATGTGTGAGCCTCCTTAAGGAACATCATCAATACA
GATATATCAGATAGTTCTGTCCAGCAAAAACGTGCTTATTTGCTACAAGTAAATTTTATTTATTTTTC
TCACTTCCCTCACTCCTTCAAATTTCCAGGTAAATAGCTGCCCAGGAGTTGCTTCATCTCTGTCCCAAAA
TACCTAGACAATTGCGGATAAGGAGAATGGCAGGGAGGGAGTAGTGGCTAAAATCACACCCTTCAAAAG
AAAGTGTGTAGGACACACAATTGTGAGAAGTCTGAATGCCATGCACATAGGGTATGACTCACTTTGAAAA
TTGTTTATAATCAAGGAAATGAAAATGAGTTAATTTCGTGCATGCATCATTTAAAGCCAAATGAGAAGAA
ACTTCTAATTTATTTTGTTACTTTTCGGCTAACACTGGCAGTATGTAACAGATTTATTTTGCAGAAACAT
CTAGATTGTCGGTGATCTTGATCCTGCCCTTATGTGTCTTGTCTTTGAAACCCAGTGTTTCCTGGATATA
TGGTTCAGGAGACAAGTTTCCAGAATCAAGTTAGGACCCAGGTCTTCTTTTTTTCCAAACCAAACATTCT
TGCTAATCCTAAACTACCTGAGGCAGCCTGTGGTGGCCTCAGCTCTAAAACCATTGTTTAAAGGCTTCTA
CCCATCAATGGCCCTTCAGCAGAGTGGTACGGTTAACGGGGTAGGGTCTGGAGTCAGGGGAGACCTGGGT

FIGURE 19 CONT'D

SEQ ID NO:3 CONT'D

TCAAATCCTACATCTTTACACCTCTAATCCCCAGTGTCCTTGTCTATAAATTGGGAATATAGCCATGTCA
TGGGATTCTTGTGAGGGTTAAATGAGGTAAAACACATACAATGCTTAGCATGTATACAATTAAGCACTAA
ATAATTGAAACACATTAAGTACTAAATGAATGTCAGCAGCTTATCACTATTATCTGTATAATGATACCAA
GGGTGTGCCGACTCATACCCTAGGGGTTGGCTGGATTCGGCCTTTTCTCTCGGGAAAACATACCCTGATT
TATTAATAGTGCTTTCAAGCATGTGATAAATTTCTCAAACTGCCTGTCTTGTTCCCTAGAAACACCAGGA
AGGCCTACCTCAAATAGCAACAGAGAAACCTATCGGAGCCTTACCCTACAGCTTTCCTTGGGGCACGGGT
GAGCAATCTGCCTTAGAGGGGAGAGCCTCTGTGCTGAGGCTCTTTGAATGCTTTGAATAAATAGATCCCC
AGATAATGAAAAGACTTCAAAACAAATTCTACAAGAAACTGAGTAGTGTTTATAGTGAGGCCCTAGTGTA
CATGCAAAAAACCCCACTGCCCTTGCTTAAATGTATCTGATTAACTTGAATACATTTTTAAATGAGGGC
TTTTTTTCCCTCTTTCAGTGTTTCGGCCAGTCATTTGCCACTTCTCATTCCATCTTAGTTCTCTGTAAAG
AAGGTGCCAGAGACCTAAGGTGCCCAAGGCAATTTTGCATTTTACAATTCTAAGCTTTAGAATGAAGTCA
TCAATTTGCTACATCCGGACTACAGTGCAATTATTCCTTTGCCTTGCTGGAAATTGGAGTGAAATCTTTC
TAGCTGTCAATTTCAACTCAGTTGCAGTAGTGTTTTGAAGAATTAATGGCGATAAGGTTAGAAAATTTTA
AGTCAAACGTAGGGAAAAAGTACCAGCTAGACCATCATAAGCATTTGCTTTGAAAGCATGCTTCTAAAGT
GTGTTTAACCTCAAATAACAGTCACAAATATGGTTATTATGAATGTATGCACAGATTTTTATGTTTCTAA
TTTTAAGAAGTTCTAGGGAGCTCCCTGTAACGATTTAGGGAATCTCTAGATTCTGATATACTGCAAGTCT
TTTAATGGTAGGAATCACATTGAATTAATTTTGTAGGCCCAGGGCCTAAATTTAGTAGGTGTTCAGTACC
TATTGGCATCAATTCATATGTAGGTTTAAAATACTGTATGAAGATACAGAATCACCACCATCAAATCAAA
TTGAAATATGTAACAGGCTAGTATAATATTAACATCTGACTTTAAACAACAACAAAGAAACCAAATGAGT
AACTCCTCCCTTCAAACTAATAGTCAGTTTCTTCCAACTCAGTCTCTTTCTCCTCTCAGGAAGAATGCGT
ATCTAAAAATTTCCCATTGCAGACTGCTGGAAACAACATTCTAAACTATTTATGCTTCTGCAATAACCTT
TCCAATTTGCTGGACCAGTGCAAGATTAAACACGAGATATCTCAAGTCTCAATGTAAAGGAACACCACGA
CAGCCTGGACTGTGGGTGAAGTTCATTCTTCCCCAGCAGACTCTGCCTTTCATTCTCGGGGTTGGGTGTG
CCCCAAACAGAGGTACCGACGGTAACGAAGCCCAAGAATGTTCAACCACAACCTGTCTGTGAAGGTGTTG
GATGACGTTTGCCATTCAGGTGAAGATTATTTATGTTCCAGTCCCACCTGAGTAGCAAAGTGAACACTGT
GCTGAATGCTCAGAAAGATGTTAATGAACCGTGCTGGACAGAGCAGAGCTGAAAGGCGCCTTGCGAGTGT
CGTAGTGAGAATGTGGCTGTCCCAGCTGCAAAGCCCTGTTAGGAGGCATGAGGAAGCACTTGCTGCCCTA
AGAAACGATGCCTTCGACATTTTCAAAAGATCTATGTGGCTGTCTGAAACAATGCGGAGAGCAGATAGAC
GCAATATTTGGGAACCAAAGAGTGACTGCTGTTGGCGTTGCATCATAACATAAGCGCTTTCCCCCTTCTC
GTCACTATCATTTGTATCAACCAAAGAACTGATCTCTGGTATCCTCGAAGCAATGCTGTGGGGATATTCT
TCATCTCTGTTCATGGTACATCAGCAATTTGTGGGGAAAAGATGGACTATATAACACAATGATCTGCCTA
AAAGAAACTGTCTCTACTTATAGGGGGCTGAGCAAACCTTAGAGCATCTGCGGATGCTCGTCATTATCTT
CAAAAGTCCCCAAGAGTTTTTCTCCATACTTTATTATTGCTATTTTGTTTAGGCTAGAAAAAAAAAAAAC
TCATAAAATTGTCTTCAAACCAAACCAAAGGAAAAAAAAAAAAAAAAA

SEQ ID NO:4

MAMESAKETRYCAVCNDYASGYHYGVWSCEGCKAFFKRSIQGHN
DYMCPATNQCTIDKNRRKSCQACRLRKCYEVGMMKGGIRKDRRGGRMLKHKRQRDDGE
GRGEVGSAGDMRAANLWPSPLMIKRSKKNSLALSLTADQMVSALLDAEPPILYSEYDP
TRPFSEASMMGLLTNLADRELVHMINWAKRVPGFVDLTLHDQVHLLECAWLEILMIGL
VWRSMEHPGKLLFAPNLLLDRNQGKCVEGMVEIFDMLLATSSRFRMMNLQGEEFVCLK
SILLLNSGISHVEAKKRILNLSPKIFGNKWFPRV

SEQUENCE LISTING

```
<160> NUMBER OF SEQ ID NOS: 43

<210> SEQ ID NO 1
<211> LENGTH: 6450
<212> TYPE: DNA
<213> ORGANISM: Homo sapiens

<400> SEQUENCE: 1
gagttgtgcc tggagtgatg tttaagccaa tgtcagggca aggcaacagt ccctggccgt      60
cctccagcac ctttgtaatg catatgagct cgggagacca gtacttaaag ttggaggccc     120
gggagcccag gagctggcgg agggcgttcg tcctgggagc tgcacttgct ccgtcgggtc     180
gccggcttca ccggaccgca ggctcccggg gcagggccgg ggccagagct cgcgtgtcgg     240
cgggacatgc gctgcgtcgc ctctaacctc gggctgtgct cttttccag gtggcccgcc     300 ggtttctgag ccttctgccc tgcggggaca cggtctgcac cctgcccgcg gccacggacc     360
atgaccatga ccctccacac caaagcatct gggatggcc tactgcatca gatccaaggg     420
aacgagctgg agcccctgaa ccgtccgcag ctcaagatcc cctggagcg gccctgggc      480 gaggtgtacc tggacagcag caagcccgcc gtgtacaact accccgaggg cgccgcctac    540
gagttcaacg ccgcggccgc cgccaacgcg caggtctacg gtcagaccgg cctccctac     600 ggccccgggt ctgaggctgc ggcgttcggc tccaacggcc tgggggtttt cccccactc    660
```

-continued

```
aacagcgtgt ctccgagccc gctgatgcta ctgcacccgc cgccgcagct gtcgcctttc      720
ctgcagcccc acggccagca ggtgccctac tacctggaga acgagcccag cggctacacg      780
gtgcgcgagg ccggcccgcc ggcattctac aggccaaatt cagataatcg acgccagggt      840
ggcagagaaa gattggccag taccaatgac aagggaagta tggctatgga atctgccaag      900
gagactcgct actgtgcagt gtgcaatgac tatgcttcag gctaccatta tggagtctgg      960
tcctgtgagg gctgcaaggc cttcttcaag agaagtattc aaggacataa cgactatatg     1020
tgtccagcca ccaaccagtg caccattgat aaaaacagga ggaagagctg ccaggcctgc     1080
cggctccgca atgctacga agtgggaatg atgaaaggtg ggatacgaaa agaccgaaga     1140
ggagggagaa tgttgaaaca caagcgccag agagatgatg gggagggcag gggtgaagtg     1200
gggtctgctg gagacatgag agctgccaac ctttggccaa gcccgctcat gatcaaacgc     1260
tctaagaaga acagcctggc cttgtccctg acggccgacc agatggtcag tgccttgttg     1320
gatgctgagc cccccatact ctattccgag tatgatccta ccagacccct cagtgaagct     1380
tcgatgatgg gcttactgac caacctggca gacagggagc tggttcacat gatcaactgg     1440
gcgaagaggg tgccaggctt tgtggatttg accctccatg atcaggtcca ccttctagaa     1500
tgtgcctggc tagagatcct gatgattggt ctcgtctggc gctccatgga gcacccagtg     1560
aagctactgt ttgctcctaa cttgctcttg gacaggaacc agggaaaatg tgtagagggc     1620
atggtggaga tcttcgacat gctgctggct acatcatctc ggttccgcat gatgaatctg     1680
cagggagagg agtttgtgtg cctcaaatct attattttgc ttaattctgg agtgtacaca     1740
tttctgtcca gcaccctgaa gtctctggaa gagaaggacc atatccaccg agtcctggac     1800
aagatcacag acactttgat ccacctgatg gccaaggcag gcctgaccct gcagcagcag     1860
caccagcggc tggcccagct cctcctcatc ctctcccaca tcaggcacat gagtaacaaa     1920
ggcatggagc atctgtacag catgaagtgc aagaacgtgg tgccctcta tgacctgctg     1980 ctggagatgc tggacgccca ccgcctacat gcgcccacta gccgtggagg ggcatccgtg     2040
gaggagacgg accaaagcca cttggccact gcgggctcta cttcatcgca ttccttgcaa     2100
aagtattaca tcacggggga ggcagagggt ttccctgcca cagtctgaga gctccctggc     2160
tcccacacgg ttcagataat ccctgctgca ttttaccctc atcatgcacc actttagcca     2220
aattctgtct cctgcataca ctccggcatg catccaacac caatggcttt ctagatgagt     2280
ggccattcat ttgcttgctc agttcttagt ggcacatctt ctgtcttctg ttgggaacag     2340
ccaaagggat tccaaggcta aatctttgta acagctctct ttccccttg ctatgttact      2400 aagcgtgagg attcccgtag ctcttcacag ctgaactcag tctatgggtt ggggctcaga     2460
taactctgtg catttaagct acttgtagag acccaggcct ggagagtaga cattttgcct     2520
ctgataagca cttttttaaat ggctctaaga ataagccaca gcaaagaatt taaagtggct     2580
cctttaattg gtgacttgga gaaagctagg tcaagggttt attatagcac cctcttgtat     2640
tcctatggca atgcatcctt ttatgaaagt ggtacacctt aaagctttta tatgactgta     2700
gcagagtatc tggtgattgt caattcactt cccctatag gaatacaagg ggccacacag     2760
ggaaggcaga tcccctagtt ggccaagact tattttaact tgatacactg cagattcaga     2820
gtgtcctgaa gctctgcctc tggctttccg gtcatgggtt ccagttaatt catgcctccc     2880
atggacctat ggagagcaac aagttgatct tagttaagtc tccctatatg agggataagt     2940
tcctgatttt tgttttttatt tttgtgttac aaaagaaagc cctccctccc tgaacttgca     3000
```

```
gtaaggtcag cttcaggacc tgttccagtg ggcactgtac ttggatcttc ccggcgtgtg    3060
tgtgccttac acaggggtga actgttcact gtggtgatgc atgatgaggg taaatggtag    3120
ttgaaaggag caggggccct ggtgttgcat ttagccctgg ggcatggagc tgaacagtac    3180
ttgtgcagga ttgttgtggc tactagagaa caagagggaa agtagggcag aaactggata    3240
cagttctgag cacagccaga cttgctcagg tggccctgca caggctgcag ctacctagga    3300
acattccttg cagaccccgc attgcctttg ggggtgccct gggatccctg ggtagtcca    3360 gctcttattc atttcccagc gtggccctgg ttggaagaag cagctgtcaa gttgtagaca    3420
gctgtgttcc tacaattggc ccagcaccct ggggcacggg agaagggtgg ggaccgttgc    3480
tgtcactact caggctgact ggggcctggt cagattacgt atgcccttgg tggtttagag    3540
ataatccaaa atcagggttt ggtttgggga agaaaatcct cccccttcct cccccgcccc    3600
gttccctacc gcctccactc ctgccagctc atttccttca atttcctttg acctataggc    3660 taaaaagaa aggctcattc cagccacagg gcagccttcc ctgggccttt gcttctctag    3720
cacaattatg ggttacttcc ttttcttaa caaaaagaa tgtttgattt cctctgggtg    3780 acttattgt ctgtaattga aaccctattg agaggtgatg tctgtgttag ccaatgaccc    3840
aggtagctgc tcgggcttct cttggtatgt cttgtttgga aaagtggatt tcattcattt    3900
ctgattgtcc agttaagtga tcaccaaagg actgagaatc tgggagggca aaaaaaaaa    3960 aaaaagtttt tatgtgcact taaatttggg gacaatttta tgtatctgtg ttaaggatat    4020
gcttaagaac ataattcttt tgttgctgtt tgtttaagaa gcaccttagt ttgtttaaga    4080
agcaccttat atagtataat atatatttt ttgaaattac attgcttgtt tatcagacaa    4140
ttgaatgtag taattctgtt ctggatttaa tttgactggg ttaacatgca aaaaccaagg    4200
aaaaatattt agtttttttt tttttttg tatacttttc aagctacctt gtcatgtata    4260
cagtcattta tgcctaaagc ctggtgatta ttcatttaaa tgaagatcac atttcatatc    4320 aactttgta tccacagtag acaaaatagc actaatccag atgcctattg ttggatattg    4380
aatgacagac aatcttatgt agcaaagatt atgcctgaaa aggaaaatta ttcagggcag    4440
ctaattttgc ttttaccaaa atatcagtag taatatttt ggacagtagc taatgggtca    4500
gtgggttctt tttaatgttt atacttagat tttcttttaa aaaattaaa ataaaacaaa    4560 aaaaatttct aggactagac gatgtaatac cagctaaagc caaacaatta tacagtggaa    4620
ggttttacat tattcatcca atgtgtttct attcatgtta agatactact acatttgaag    4680
tgggcagaga acatcagatg attgaaatgt tcgcccaggg gtctccagca actttggaaa    4740 tctcttttgta ttttttacttg aagtgccact aatggacagc agatattttc tggctgatgt    4800
tggtattggg tgtaggaaca tgatttaaaa aaaaaactct tgcctctgct ttccccccact    4860 ctgaggcaag ttaaaatgta aaagatgtga tttatctggg gggctcaggt atggtgggga    4920
agtggattca ggaatctggg gaatggcaaa tatattaaga agagtattga aagtatttgg    4980
aggaaaatgg ttaattctgg gtgtgcacca aggttcagta gagtccactt ctgccctgga    5040
gaccacaaat caactagctc catttacagc catttctaaa atggcagctt cagttctaga    5100
gaagaaagaa caacatcagc agtaaagtcc atggaatagc tagtggtctg tgtttctttt    5160
cgccattgcc tagcttgccg taatgattct ataatgccat catgcagcaa ttatgagagg    5220
ctaggtcatc caaagagaag accctatcaa tgtaggttgc aaaatctaac ccctaaggaa    5280
gtgcagtctt tgatttgatt tccctagtaa ccttgcagat atgtttaacc aagccatagc    5340
ccatgccttt tgagggctga acaaataagg gacttactga taatttactt ttgatcacat    5400
```

-continued

```
taaggtgttc tcaccttgaa atcttataca ctgaaatggc cattgattta ggccactggc    5460
ttagagtact ccttcccctg catgacactg attacaaata ctttcctatt catactttcc    5520
aattatgaga tggactgtgg gtactgggag tgatcactaa caccatagta atgtctaata    5580
ttcacaggca gatctgcttg gggaagctag ttatgtgaaa ggcaaataaa gtcatacagt    5640
agctcaaaag gcaaccataa ttctctttgg tgcaagtctt gggagcgtga tctagattac    5700
actgcaccat tcccaagtta atcccctgaa aacttactct caactggagc aaatgaactt    5760
tggtcccaaa tatccatctt ttcagtagcg ttaattatgc tctgtttcca actgcatttc    5820
ctttccaatt gaattaaagt gtggcctcgt ttttagtcat ttaaaattgt tttctaagta    5880
attgctgcct ctattatggc acttcaattt tgcactgtct tttgagattc aagaaaaatt    5940
tctattcatt tttttgcatc caattgtgcc tgaactttta aaatatgtaa atgctgccat    6000
gttccaaacc catcgtcagt gtgtgtgttt agagctgtgc accctagaaa caacatactt    6060
gtcccatgag caggtgcctg agacacagac ccctttgcat tcacagagag gtcattggtt    6120
atagagactt gaattaataa gtgacattat gccagtttct gttctctcac aggtgataaa    6180
caatgctttt tgtgcactac atactcttca gtgtagagct cttgttttat gggaaaaggc    6240
tcaaatgcca aattgtgttt gatggattaa tatgcccttt tgccgatgca tactattact    6300
gatgtgactc ggttttgtcg cagctttgct ttgtttaatg aaacacactt gtaaacctct    6360
tttgcacttt gaaaaagaat ccagcgggat gctcgagcac ctgtaaacaa ttttctcaac    6420
ctatttgatg ttcaaataaa gaattaaact                                      6450
```

<210> SEQ ID NO 2
<211> LENGTH: 595
<212> TYPE: PRT
<213> ORGANISM: Homo sapiens

<400> SEQUENCE: 2

```
Met Thr Met Thr Leu His Thr Lys Ala Ser Gly Met Ala Leu Leu His
  1               5                  10                  15

Gln Ile Gln Gly Asn Glu Leu Glu Pro Leu Asn Arg Pro Gln Leu Lys
                 20                  25                  30

Ile Pro Leu Glu Arg Pro Leu Gly Glu Val Tyr Leu Asp Ser Ser Lys
             35                  40                  45

Pro Ala Val Tyr Asn Tyr Pro Glu Gly Ala Ala Tyr Glu Phe Asn Ala
         50                  55                  60

Ala Ala Ala Ala Asn Ala Gln Val Tyr Gly Gln Thr Gly Leu Pro Tyr
     65                  70                  75                  80

Gly Pro Gly Ser Glu Ala Ala Ala Phe Gly Ser Asn Gly Leu Gly Gly
                 85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
        130                 135                 140

Gly Pro Pro Ala Phe Tyr Arg Pro Asn Ser Asp Asn Arg Arg Gln Gly
    145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
```

-continued

```
                180                 185                 190
Ser Gly Tyr His Tyr Gly Val Trp Ser Cys Glu Gly Cys Lys Ala Phe
            195                 200                 205
Phe Lys Arg Ser Ile Gln Gly His Asn Asp Tyr Met Cys Pro Ala Thr
            210                 215                 220
Asn Gln Cys Thr Ile Asp Lys Asn Arg Arg Lys Ser Cys Gln Ala Cys
225                 230                 235                 240
Arg Leu Arg Lys Cys Tyr Glu Val Gly Met Met Lys Gly Gly Ile Arg
                245                 250                 255
Lys Asp Arg Arg Gly Gly Arg Met Leu Lys His Lys Arg Gln Arg Asp
                260                 265                 270
Asp Gly Glu Gly Arg Gly Glu Val Gly Ser Ala Gly Asp Met Arg Ala
                275                 280                 285
Ala Asn Leu Trp Pro Ser Pro Leu Met Ile Lys Arg Ser Lys Lys Asn
            290                 295                 300
Ser Leu Ala Leu Ser Leu Thr Ala Asp Gln Met Val Ser Ala Leu Leu
305                 310                 315                 320
Asp Ala Glu Pro Pro Ile Leu Tyr Ser Glu Tyr Asp Pro Thr Arg Pro
                325                 330                 335
Phe Ser Glu Ala Ser Met Met Gly Leu Leu Thr Asn Leu Ala Asp Arg
                340                 345                 350
Glu Leu Val His Met Ile Asn Trp Ala Lys Arg Val Pro Gly Phe Val
                355                 360                 365
Asp Leu Thr Leu His Asp Gln Val His Leu Leu Glu Cys Ala Trp Leu
            370                 375                 380
Glu Ile Leu Met Ile Gly Leu Val Trp Arg Ser Met Glu His Pro Val
385                 390                 395                 400
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
                420                 425                 430
Ser Arg Phe Arg Met Met Asn Leu Gln Gly Glu Glu Phe Val Cys Leu
            435                 440                 445
Lys Ser Ile Ile Leu Leu Asn Ser Gly Val Tyr Thr Phe Leu Ser Ser
            450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Gln Arg Leu Ala Gln Leu Leu Leu Ile Leu Ser
            500                 505                 510
His Ile Arg His Met Ser Asn Lys Gly Met Glu His Leu Tyr Ser Met
            515                 520                 525
Lys Cys Lys Asn Val Val Pro Leu Tyr Asp Leu Leu Leu Glu Met Leu
            530                 535                 540
Asp Ala His Arg Leu His Ala Pro Thr Ser Arg Gly Gly Ala Ser Val
545                 550                 555                 560
Glu Glu Thr Asp Gln Ser His Leu Ala Thr Ala Gly Ser Thr Ser Ser
                565                 570                 575
His Ser Leu Gln Lys Tyr Tyr Ile Thr Gly Glu Ala Glu Gly Phe Pro
            580                 585                 590
Ala Thr Val
        595
```

```
<210> SEQ ID NO 3
<211> LENGTH: 5439
<212> TYPE: DNA
<213> ORGANISM: Homo sapiens
<220> FEATURE:
<221> NAME/KEY: 5'UTR
<222> LOCATION: (1)..(233)
<220> FEATURE:
<221> NAME/KEY: CDS
<222> LOCATION: (234)..(1166)
<220> FEATURE:
<221> NAME/KEY: 3'UTR
<222> LOCATION: (1167)..(5439)

<400> SEQUENCE: 3
ggcttaaaaa taatctcctg ccagcccagt gacaagcctg tcccacccgg ggagaatgcc      60
ccggagtggc gtgcgggtca gccagggtct gcgcctcgca gccactgtgg aaggagcgcg     120
gccggtccag gacacaggag accactttgt gacttcaatg gcgaaggcca aattcagata     180
atcgacgcca gggtggcaga gaaagattgg ccagtaccaa tgacaaggga agt atg       236
                                                          Met
                                                          1 gct atg gaa tct gcc aag gag act cgc tac tgt gca gtg tgc aat gac       284
Ala Met Glu Ser Ala Lys Glu Thr Arg Tyr Cys Ala Val Cys Asn Asp
            5                  10                  15 tat gct tca ggc tac cat tat gga gtc tgg tcc tgt gag ggc tgc aag       332
Tyr Ala Ser Gly Tyr His Tyr Gly Val Trp Ser Cys Glu Gly Cys Lys
         20                  25                  30 gcc ttc ttc aag aga agt att caa gga cat aac gac tat atg tgt cca       380
Ala Phe Phe Lys Arg Ser Ile Gln Gly His Asn Asp Tyr Met Cys Pro
     35                  40                  45 gcc acc aac cag tgc acc att gat aaa aac agg agg aag agc tgc cag       428
Ala Thr Asn Gln Cys Thr Ile Asp Lys Asn Arg Arg Lys Ser Cys Gln
 50                  55                  60                  65 gcc tgc cgg ctc cgc aaa tgc tac gaa gtg gga atg atg aaa ggt ggg       476
Ala Cys Arg Leu Arg Lys Cys Tyr Glu Val Gly Met Met Lys Gly Gly
                 70                  75                  80 ata cga aaa gac cga aga gga ggg aga atg ttg aaa cac aag cgc cag       524
Ile Arg Lys Asp Arg Arg Gly Gly Arg Met Leu Lys His Lys Arg Gln
             85                  90                  95 aga gat gat ggg gag ggc agg ggt gaa gtg ggg tct gct gga gac atg       572
Arg Asp Asp Gly Glu Gly Arg Gly Glu Val Gly Ser Ala Gly Asp Met
        100                 105                 110 aga gct gcc aac ctt tgg cca agc ccg ctc atg atc aaa cgc tct aag       620
Arg Ala Ala Asn Leu Trp Pro Ser Pro Leu Met Ile Lys Arg Ser Lys
    115                 120                 125 aag aac agc ctg gcc ttg tcc ctg acg gcc gac cag atg gtc agt gcc       668
Lys Asn Ser Leu Ala Leu Ser Leu Thr Ala Asp Gln Met Val Ser Ala
130                 135                 140                 145 ttg ttg gat gct gag ccc ccc ata ctc tat tcc gag tat gat cct acc       716
Leu Leu Asp Ala Glu Pro Pro Ile Leu Tyr Ser Glu Tyr Asp Pro Thr
                150                 155                 160 aga ccc ttc agt gaa gct tcg atg atg ggc tta ctg acc aac ctg gca       764
Arg Pro Phe Ser Glu Ala Ser Met Met Gly Leu Leu Thr Asn Leu Ala
            165                 170                 175 gac agg gag ctg gtt cac atg atc aac tgg gcg aag agg gtg cca ggc       812
Asp Arg Glu Leu Val His Met Ile Asn Trp Ala Lys Arg Val Pro Gly
        180                 185                 190 ttt gtg gat ttg acc ctc cat gat cag gtc cac ctt cta gaa tgt gcc       860
Phe Val Asp Leu Thr Leu His Asp Gln Val His Leu Leu Glu Cys Ala
    195                 200                 205
```

```
tgg cta gag atc ctg atg att ggt ctc gtc tgg cgc tcc atg gag cac      908
Trp Leu Glu Ile Leu Met Ile Gly Leu Val Trp Arg Ser Met Glu His
210                 215                 220                 225 cca ggg aag cta ctg ttt gct cct aac ttg ctc ttg gac agg aac cag      956
Pro Gly Lys Leu Leu Phe Ala Pro Asn Leu Leu Leu Asp Arg Asn Gln
            230                 235                 240 gga aaa tgt gta gag ggc atg gtg gag atc ttc gac atg ctg ctg gct     1004
Gly Lys Cys Val Glu Gly Met Val Glu Ile Phe Asp Met Leu Leu Ala
    245                 250                 255 aca tca tct cgg ttc cgc atg atg aat ctg cag gga gag gag ttt gtg     1052
Thr Ser Ser Arg Phe Arg Met Met Asn Leu Gln Gly Glu Glu Phe Val
260                 265                 270 tgc ctc aaa tct att ctt ttg ctt aat tct ggt atc tca cat gta gaa     1100
Cys Leu Lys Ser Ile Leu Leu Leu Asn Ser Gly Ile Ser His Val Glu
275                 280                 285 gca aag aag aga atc ctg aac ttg cat cct aaa ata ttt gga aac aag     1148
Ala Lys Lys Arg Ile Leu Asn Leu His Pro Lys Ile Phe Gly Asn Lys
290                 295                 300                 305 tgg ttt cct cgt gtc taa agcctctggt cataaggcct cacagtatcc            1196
Trp Phe Pro Arg Val
                310 tgcagatcat caaatccgtg tgtggacgtg gggacatttt gttttgaggc agttacatga   1256 ccatgggcaa gtggattggt ctctctggcc ttcagttttc tcatttgcaa tgattcaatg   1316 gtttgcctta agtgtctta agaaggatag gatagctacc cacaaacttt ggatcaaatt    1376 ttcttcaaaa catccttccc ctgactttaa aatatgccct ggcaaccaac actcaacacc   1436 cgtagctaga tgagttataa cagagtgact gaagagagct cccacaattc ctagttatta   1496 aatacctgac taattttcat taggagacat ttaagaactt tagtgatggg aagatttaca   1556 tatataattg atagtacaat ctgacagagc tgaatagctc ctgtttgtca actgttaaat   1616 tctttgtgca attaggtcaa agatcaagat caaaacaagg ctgcccatt gacctgttca    1676 ctcctgagaa aaatggcaaa ccattgaatc ataaatcatg acagccaaaa taattttagg   1736 atattaatgc acccctcatc tttgcaagtg agaaaactga aggccagaga gactaattta   1796 cttgcccatt tttgataaaa atgtcaccat ttacagaatg tggactccta tgttggagtc   1856 tgttgaagga catggcacat ttaacagcat cagagcattt tttattaaaa tttaatttgt   1916 gcatgacttc taatgctgaa gaacgccaag ctaggaagaa gtcatgggct gagatgggga   1976 cagagagaac acacaatatt cagtgactgt ccgtgcagct ggctgcccTt gaaaatatcc   2036 gaactatcca ctgggaaaat gcctgtcccc ttggggtaat taccagagtt caacatgcc    2096 caaagctgcc tcatcttcag ggggaacttg ttctagcgat tttagtatca agaagctaat   2156 ggtcccaggg aaaggttat ttttaatatt tagctactgt gctaaaaatc acctaagttt    2216 ctagagtctt gggaaatttc ataagggaaa gaacaaaggc aacttgttga ctacccactg   2276 gtcattctcc tctggtctta ttacatacat ggatgccagt ttagattgtg tttatatagg   2336 aaaatttaaa tgtgtgagcc tccttaagga acatcatcaa tacagatata tcagatagtt   2396 ctgtccagca aaaacgtgc ttatttgcta caagtaaatt tttatttatt tttctcactt    2456 ccctcactcc ttcaaatttc caggtaaata gctgcccagg agttgcttca tctctgtccc   2516 aaaataccta gacaattgcg ggataaggag aatggcaggg agggagtagt ggctaaaatc   2576 acacccttca aaagaaagtg tgtaggacac acaattgtga gaagtctgaa tgccatgcac   2636 ataggtatg actcactttg aaaattgttt ataatcaagg aaatgaaaat gagttaattt    2696
```

```
cgtgcatgca tcatttaaag ccaaatgaga agaaacttct aatttatttt gttacttttc   2756
ggctaacact ggcagtatgt aacagattta ttttgcagaa acatctagat tgtccgtgat   2816
cttgatcctg cccttatgtg tcttgtcttt gaaacccagt gtttcctgga tatatggttc   2876
aggagacaag tttccagaat caagttagga cccaggtctt cttttttttcc aaaccaaaca   2936
ttcttgctaa tcctaaacta cctgaggcag cctgtggtgg cctcagctct aaaaccattg   2996
tttaaaggct tctacccatc aatggcccct cagcagagtg gtacggttaa cggggtaggg   3056
tctggagtca ggggagacct gggttcaaat cctacatctt tacacctcta atccccagtg   3116
tccttgtcta taaattggga atatagccat gtcatgggat tcttgtgagg gttaaatgag   3176
gtaaaacaca tacaatgctt agcatgtata caattaagca ctaaataatt gaaacacatt   3236
aagtactaaa tgaatgtcag cagcttatca ctattatctg tataatgata ccaagggtgt   3296
gccgactcat acccttaggg gttggctgga ttcggccttt tctctcggga aaacatacct   3356
gatttattaa tagtgctttc aagcatgtga taaatttctc aaactgcctg tcttgttccc   3416
tagaaacacc aggaaggcct acctcaaata gcaacagaga aacctatcgg agccttaccc   3476
tacagctttc cttggggcac gggtgagcaa tctgccttag aggggagagg ctctgtgctg   3536
aggctctttg aatgctttga ataaatagat ccccagataa tgaaaagact tcaaaacaaa   3596
ttctacaaga aactgagtag tgtttatagt gaggccctag tgtacatgca aaaaccccc    3656
actgcccttg cttaaatgta tctgattaac ttgaatacat ttttaaatga gggctttttt   3716
tccctctttc agtgtttcgg ccagtcattt gccacttctc attccatctt agttctctgt   3776
aaagaaggtg ccagagacct aaggtgccca aggcaatttt gcattttaca attctaagct   3836
ttagaatgaa gtcatcaatt tgctacatcc ggactacagt gcaattattc ctttgccttg   3896
ctggaaattg gagtgaaatc tttctagctg tcaatttcaa ctcagttgca gtagtgtttt   3956
gaagaattaa tggcgataag gttagaaaat tttaagtcaa acgtagggaa aaagtaccag   4016
ctagaccatc ataagcattt gctttgaaag catgcttcta aagtgtgttt aacctcaaat   4076
aacagtcaca aatatggtta ttatgaatgt atgcacagat ttttatgttt ctaattttaa   4136
gaagttctag ggagctccct gtaacgattt agggaatctc tagattctga tatactgcaa   4196
gtctttttaat ggtaggaatc acattgaatt aattttgtag gcccagggcc taaatttagt   4256
aggtgttcag tacctattgg catcaattca tatgtaggtt taaaatactg tatgaagata   4316
cagaatcacc accatcaaat caaattgaaa tatgtaacag gctagtataa tattaacatc   4376
tgactttaaa caacaacaaa gaaaccaaat gagtaactcc tcccttcaaa ctaatagtca   4436
gtttcttcca actcagtctc tttctcctct caggaagaat gcgtatctaa aaatttccca   4496
ttgcagactg ctggaaacaa cattctaaac tatttatgct tctgcaataa cctttccaat   4556
ttgctggacc agtgcaagat taaacacgag atatctcaag tctcaatgta aaggaacacc   4616
acgacagcct ggactgtggg tgaagttcat tcttccccag cagactctgc ctttcattct   4676
cggggttggg tgtgccccaa acagaggtac cgacggtaac gaagcccaag aatgttcaac   4736
cacaacctgt ctgtgaaggt gttggatgac gtttgccatt caggtgaaga ttatttatgt   4796
tccagtccca cctgagtagc aaagtgaaca ctgtgctgaa tgctcagaaa gatgttaatg   4856
aaccgtgctg gacagagcag agctgaaagg cgccttgcga gtgtcgtagt gagaatgtgg   4916
ctgtcccagc tgcaaagccc tgttaggagg catgaggaag cacttgctgc cctaagaaac   4976
gatgccttcg acattttcaa aagatctatg tggctgtctg aaacaatgcg gagagcagat   5036
agacgcaata tttgggaacc aaagagtgac tgctgttggc gttgcatcat aacataagcg   5096
```

-continued

```
ctttcccct tctcgtcact atcatttgta tcaaccaaag aactgatctc tggtatcctc    5156
gaaggaatgc tgtggggata ttcttcatct ctgttcatgg tacatcagca atttgtgggg    5216
aaaagatgga ctatataaca caatgatctg cctaaaagaa actgtctcta cttatagggg    5276
gctgagcaaa ccttagagca tctgcggatg ctcgtcatta tcttcaaaag tccccaagag    5336
tttttctcca tactttatta ttgctatttt gtttaggcta gaaaaaaaaa aaactcataa    5396
aattgtcttc aaaccaaacc aaaggaaaaa aaaaaaaaa aaa                      5439
```

<210> SEQ ID NO 4
<211> LENGTH: 310
<212> TYPE: PRT
<213> ORGANISM: Homo sapiens

<400> SEQUENCE: 4

```
Met Ala Met Glu Ser Ala Lys Glu Thr Arg Tyr Cys Ala Val Cys Asn
1               5                   10                  15

Asp Tyr Ala Ser Gly Tyr His Tyr Gly Val Trp Ser Cys Glu Gly Cys
            20                  25                  30

Lys Ala Phe Phe Lys Arg Ser Ile Gln Gly His Asn Asp Tyr Met Cys
        35                  40                  45

Pro Ala Thr Asn Gln Cys Thr Ile Asp Lys Asn Arg Arg Lys Ser Cys
    50                  55                  60

Gln Ala Cys Arg Leu Arg Lys Cys Tyr Glu Val Gly Met Met Lys Gly
65                  70                  75                  80

Gly Ile Arg Lys Asp Arg Arg Gly Gly Arg Met Leu Lys His Lys Arg
                85                  90                  95

Gln Arg Asp Asp Gly Glu Gly Arg Gly Glu Val Gly Ser Ala Gly Asp
            100                 105                 110

Met Arg Ala Ala Asn Leu Trp Pro Ser Pro Leu Met Ile Lys Arg Ser
        115                 120                 125

Lys Lys Asn Ser Leu Ala Leu Ser Leu Thr Ala Asp Gln Met Val Ser
    130                 135                 140

Ala Leu Leu Asp Ala Glu Pro Pro Ile Leu Tyr Ser Glu Tyr Asp Pro
145                 150                 155                 160

Thr Arg Pro Phe Ser Glu Ala Ser Met Met Gly Leu Leu Thr Asn Leu
                165                 170                 175

Ala Asp Arg Glu Leu Val His Met Ile Asn Trp Ala Lys Arg Val Pro
            180                 185                 190

Gly Phe Val Asp Leu Thr Leu His Asp Gln Val His Leu Leu Glu Cys
        195                 200                 205

Ala Trp Leu Glu Ile Leu Met Ile Gly Leu Val Trp Arg Ser Met Glu
    210                 215                 220

His Pro Gly Lys Leu Leu Phe Ala Pro Asn Leu Leu Asp Arg Asn
225                 230                 235                 240

Gln Gly Lys Cys Val Glu Gly Met Val Glu Ile Phe Asp Met Leu Leu
                245                 250                 255

Ala Thr Ser Ser Arg Phe Arg Met Met Asn Leu Gln Gly Glu Glu Phe
            260                 265                 270

Val Cys Leu Lys Ser Ile Leu Leu Asn Ser Gly Ile Ser His Val
        275                 280                 285

Glu Ala Lys Lys Arg Ile Leu Asn Leu His Pro Lys Ile Phe Gly Asn
    290                 295                 300

Lys Trp Phe Pro Arg Val
```

```
<210> SEQ ID NO 5
<211> LENGTH: 22
<212> TYPE: RNA
<213> ORGANISM: artificial
<220> FEATURE:
<223> OTHER INFORMATION: mutant ER-alpha target sequence

<400> SEQUENCE: 5
uuucuacguc auggaggaag au                                              22

<210> SEQ ID NO 6
<211> LENGTH: 22
<212> TYPE: RNA
<213> ORGANISM: artificial
<220> FEATURE:
<223> OTHER INFORMATION: ER-alpha target sequence

<400> SEQUENCE: 6
uuucuaagua auugcugccu cu                                              22

<210> SEQ ID NO 7
<211> LENGTH: 22
<212> TYPE: RNA
<213> ORGANISM: artificial
<220> FEATURE:
<223> OTHER INFORMATION: microRNA targeting ER-alpha

<400> SEQUENCE: 7
uugauauguu ggaugaugga gu                                              22

<210> SEQ ID NO 8
<211> LENGTH: 22
<212> TYPE: RNA
<213> ORGANISM: artificial
<220> FEATURE:
<223> OTHER INFORMATION: microRNA targeting ER-alpha

<400> SEQUENCE: 8
uuggugucuu ggaugaugga gu                                              22

<210> SEQ ID NO 9
<211> LENGTH: 22
<212> TYPE: RNA
<213> ORGANISM: artificial
<220> FEATURE:
<223> OTHER INFORMATION: microRNA targeting ER-alpha

<400> SEQUENCE: 9
uugguauguu ggaugaugga gu                                              22

<210> SEQ ID NO 10
<211> LENGTH: 22
<212> TYPE: RNA
<213> ORGANISM: artificial
<220> FEATURE:
<223> OTHER INFORMATION: microRNA targeting ER-alpha

<400> SEQUENCE: 10
uugauacguu ggaugaugga ga                                              22

<210> SEQ ID NO 11
<211> LENGTH: 22
<212> TYPE: RNA
<213> ORGANISM: artificial
```

```
<220> FEATURE:
<223> OTHER INFORMATION: microRNA targeting ER-alpha

<400> SEQUENCE: 11
uugauauguu ggaggaugga gu                                              22

<210> SEQ ID NO 12
<211> LENGTH: 22
<212> TYPE: RNA
<213> ORGANISM: artificial
<220> FEATURE:
<223> OTHER INFORMATION: microRNA targeting ER-alpha

<400> SEQUENCE: 12
uugauauguu agaugaugga gu                                              22

<210> SEQ ID NO 13
<211> LENGTH: 22
<212> TYPE: RNA
<213> ORGANISM: artificial
<220> FEATURE:
<223> OTHER INFORMATION: microRNA targeting ER-alpha

<400> SEQUENCE: 13
uugacauguu ugaugaugga gu                                              22

<210> SEQ ID NO 14
<211> LENGTH: 22
<212> TYPE: RNA
<213> ORGANISM: artificial
<220> FEATURE:
<223> OTHER INFORMATION: microRNA targeting ER-alpha

<400> SEQUENCE: 14
uugucguguu ugaugaugga gu                                              22

<210> SEQ ID NO 15
<211> LENGTH: 22
<212> TYPE: RNA
<213> ORGANISM: artificial
<220> FEATURE:
<223> OTHER INFORMATION: mutant ER-alpha36 target sequence

<400> SEQUENCE: 15
aacaccagga aggcagcaag aa                                              22

<210> SEQ ID NO 16
<211> LENGTH: 22
<212> TYPE: RNA
<213> ORGANISM: artificial
<220> FEATURE:
<223> OTHER INFORMATION: ER-alpha36 target sequence

<400> SEQUENCE: 16
aacaccagga aggccuaccu ca                                              22

<210> SEQ ID NO 17
<211> LENGTH: 15
<212> TYPE: DNA
<213> ORGANISM: artificial
<220> FEATURE:
<223> OTHER INFORMATION: synthetic oligonucleotide primer

<400> SEQUENCE: 17
gcggccacgg accat                                                      15
```

```
<210> SEQ ID NO 18
<211> LENGTH: 22
<212> TYPE: DNA
<213> ORGANISM: artificial
<220> FEATURE:
<223> OTHER INFORMATION: synthetic oligonucleotide primer

<400> SEQUENCE: 18
ttcccttgga tctgatgcag ta                                                  22

<210> SEQ ID NO 19
<211> LENGTH: 25
<212> TYPE: DNA
<213> ORGANISM: artificial
<220> FEATURE:
<223> OTHER INFORMATION: synthetic oligonucleotide probe
<220> FEATURE:
<221> NAME/KEY: misc_feature
<222> LOCATION: (1)..(1)
<223> OTHER INFORMATION: 5' FAM fluorescent reporter
<220> FEATURE:
<221> NAME/KEY: misc_feature
<222> LOCATION: (25)..(25)
<223> OTHER INFORMATION: 3' TAMRA fluorescent quencher

<400> SEQUENCE: 19
ccatgaccct ccacaccaaa gcatc                                               25

<210> SEQ ID NO 20
<211> LENGTH: 15
<212> TYPE: DNA
<213> ORGANISM: artificial
<220> FEATURE:
<223> OTHER INFORMATION: synthetic oligonucleotide primer

<400> SEQUENCE: 20
gcggccacgg accat                                                          15

<210> SEQ ID NO 21
<211> LENGTH: 22
<212> TYPE: DNA
<213> ORGANISM: artificial
<220> FEATURE:
<223> OTHER INFORMATION: synthetic oligonucleotide primer

<400> SEQUENCE: 21
ttcccttgga tctgatgcag ta                                                  22

<210> SEQ ID NO 22
<211> LENGTH: 25
<212> TYPE: DNA
<213> ORGANISM: artificial
<220> FEATURE:
<223> OTHER INFORMATION: synthetic oligonucleotide probe
<220> FEATURE:
<221> NAME/KEY: misc_feature
<222> LOCATION: (1)..(1)
<223> OTHER INFORMATION: 5' FAM fluorescent reporter
<220> FEATURE:
<221> NAME/KEY: misc_feature
<222> LOCATION: (25)..(25)
<223> OTHER INFORMATION: 3' TAMRA fluorescent quencher

<400> SEQUENCE: 22
ccatgaccct ccacaccaaa gcatc                                               25

<210> SEQ ID NO 23
<211> LENGTH: 24
```

```
<212> TYPE: DNA
<213> ORGANISM: artificial
<220> FEATURE:
<223> OTHER INFORMATION: synthetic oligonucleotide primer

<400> SEQUENCE: 23
caagtggttt cctcgtgtct aaag                                          24

<210> SEQ ID NO 24
<211> LENGTH: 20
<212> TYPE: DNA
<213> ORGANISM: artificial
<220> FEATURE:
<223> OTHER INFORMATION: synthetic oligonucleotide primer

<400> SEQUENCE: 24
acgtccacac acggatttga                                               20

<210> SEQ ID NO 25
<211> LENGTH: 22
<212> TYPE: DNA
<213> ORGANISM: C. elegans

<400> SEQUENCE: 25
tgaggtagta ggttgtatag tt                                            22

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000
```

<210> SEQ ID NO 33

<400> SEQUENCE: 33

000

<210> SEQ ID NO 34

<400> SEQUENCE: 34

000

<210> SEQ ID NO 35
<211> LENGTH: 24
<212> TYPE: DNA
<213> ORGANISM: artificial
<220> FEATURE:
<223> OTHER INFORMATION: synthetic oligonucleotide primer

<400> SEQUENCE: 35
caagtggttt cctcgtgtct aaag                                    24

<210> SEQ ID NO 36
<211> LENGTH: 20
<212> TYPE: DNA
<213> ORGANISM: artificial
<220> FEATURE:
<223> OTHER INFORMATION: synthetic oligonucleotide primer

<400> SEQUENCE: 36
acgtccacac acggatttga                                         20

<210> SEQ ID NO 37
<211> LENGTH: 15
<212> TYPE: DNA
<213> ORGANISM: artificial
<220> FEATURE:
<223> OTHER INFORMATION: synthetic oligonucleotide primer

<400> SEQUENCE: 37
gcggccacgg accat                                              15

<210> SEQ ID NO 38
<211> LENGTH: 22
<212> TYPE: DNA
<213> ORGANISM: artificial
<220> FEATURE:
<223> OTHER INFORMATION: synthetic oligonucleotide primer

<400> SEQUENCE: 38
ttcccttgga tctgatgcag ta                                      22

<210> SEQ ID NO 39
<211> LENGTH: 48
<212> TYPE: DNA
<213> ORGANISM: Homo sapiens

<400> SEQUENCE: 39
ctagtttaaa attgttttct aagtaattgc tgcctctatt atggcaca           48

<210> SEQ ID NO 40
<211> LENGTH: 48
<212> TYPE: DNA
<213> ORGANISM: Homo sapiens

```
<400> SEQUENCE: 40
agcttgtgcc ataatagagg cagcaattac ttagaaaaca attttaaa                    48

<210> SEQ ID NO 41
<211> LENGTH: 48
<212> TYPE: DNA
<213> ORGANISM: Homo sapiens

<400> SEQUENCE: 41
ctagtgttcc ctagaaacac caggaaggcc tacctcaaat agcaacaa                    48

<210> SEQ ID NO 42
<211> LENGTH: 48
<212> TYPE: DNA
<213> ORGANISM: Homo sapiens

<400> SEQUENCE: 42
agctttgttg ctatttgagg taggccttcc tggtgtttct agggaaca                    48

<210> SEQ ID NO 43
<211> LENGTH: 28
<212> TYPE: DNA
<213> ORGANISM: artificial
<220> FEATURE:
<223> OTHER INFORMATION: synthetic oligonucleotide probe
<220> FEATURE:
<221> NAME/KEY: misc_feature
<222> LOCATION: (1)..(1)
<223> OTHER INFORMATION: 5' FAM fluorescent reporter
<220> FEATURE:
<221> NAME/KEY: misc_feature
<222> LOCATION: (28)..(28)
<223> OTHER INFORMATION: 3' TAMRA fluorescent quencher

<400> SEQUENCE: 43
tggtcataag gcctcacagt atcctgca                                          28
```

POLYNUCLEOTIDES FOR USE IN TREATING AND DIAGNOSING CANCERS

CROSS-REFERENCE TO RELATED APPLICATIONS

This application claims the benefit of U.S. Provisional Application Ser. No. 61/338,704, filed Feb. 23, 2010, which is incorporated by reference herein.

BACKGROUND

Breast cancer is the second most common cause of death from cancer in women in Europe and North America. Annually, more than 1.3 million women are diagnosed with breast cancer worldwide, and approximately half a million die from the disease (Heneghan et al., 2009, J Oncol doi:10.1155/2010/950201). The involvement of estrogen in mammary carcinogenesis has been known for more than 100 years (Clemons and Goss, 2001, N. Engl. J. Med., 344:276-85). It is prevailingly known that estrogen signaling is mediated by two major estrogen receptors (ER), ER-α and ER-β (Weihua et al., 2003, FEBS Lett., 546:17-24), which share a common structural architecture. ER-α is often used to refer to a 66 kD protein that functions as a transcription factor and regulates the transcription of estrogen-responsive genes. ER-α is comprised of 6 domains, A-F (Evans, 1988, Science, 240:889-95). The A/B region contains a ligand-independent transactivation domain (AF-1). Regions C and E are responsible for DNA and ligand binding, respectively. A ligand-inducible transcription activating function (AF-2) is present in the ligand-binding domain D/E/F (Berry et al., 1990, EMBO J., 9:2811-8). Recent research revealed the existence of a truncated form of ER-α with a molecular weight of 46 kDa, which lacks the first 173 aa (AF-1 domain) of ER-α and is designated as ER-α46 (Flouriot et al., 2000, EMBO J., 19:4688-700). The full-length ER-α is therefore recognized as ER-α66. ER-α46 functions to inhibit the transcriptional activity mediated by the AF-1 domain of ER-α66 (Flouriot et al., 2000, EMBO J., 19:4688-700) and to signal a membrane-initiated estrogen pathway (Li et al., 2003, Proc. Natl. Acad. Sci. U.S.A., 100:4807-12). Previously, we identified and cloned a 36-kD novel isoform of ER-α66, ER-α36 (Wang et al., 2005, Biochem. Biophys. Res. Commun. 336:1023-7). ER-α36 is transcribed from a promoter located in the first intron of the ER-α66 gene and lacks both transcriptional activation domains (AF-1 and AF-2), but retains the DNA binding, dimerization, and partial ligand-binding domains. Additionally, it possesses an extra, unique 27-aa domain to replace the last 138 aa of the ER-α66. ER-α36 is predominantly localized on the plasma membranes and mediates membrane-initiated estrogen signal pathway (Wang et al., 2006, Proc. Natl. Acad. Sci. U. S. A., 103:9063-8) such as activation of the mitogen-activated protein kinase/extracellular signal-regulated kinase (the MAPK/ERK) signaling pathway (Segars and Driggers, 2002, Trends Endocrinol. Metab., 13:349-54). ER-α36 expression was detected in both ER-α66-positive and -negative breast cancer tumors (Lee et al., 2008, Anticancer Res. 28:479-83, Zhang et al., 2010, Oncogene, October 11, doi:10.1038/onc.2010.458). High levels of ER-α36 expression are also associated with tamoxifen resistance; breast cancer patients with tumors highly expressing ER-α36 benefit less from tamoxifen treatment (Shi et al., 2009, J. Clin. Oncol., 27:3423-9).

The discovery of microRNAs (miRNAs), which are ~22 nt long, has brought new concepts to breast cancer research. A line of studies have shown that deregulation of mRNAs causes tumorigenesis and metastasis (Medina and Slack, 2008 Cell Cycle 7:2485-92). Further, growing evidence shows that miRNAs may be 'master' regulators that regulate cancer cell proliferation through different mechanisms. For example, miR-21 has been demonstrated to be an onco-microRNA (oncomiR) in breast tumorigenesis. Up-regulation of this miRNA causes aggressive malignant growth of breast cancer via regulation of the anti-apoptotic factors Bcl-2, TPM1, tumor suppressor PTEN, and PDCD4 (Ng et al., 2009, J Oncol, doi: 10.1155/2009/305420). MiR-206 significantly down-regulated ER-α by binding to the 3' UTR (Adams et al., 2007, Mol Endocrinol 21:1132-47, Kondo et al., 2008, Cancer Res 68:5004-8). MiR-17-5p regulates malignant growth of breast cancer by targeting a transcriptional factor, AIB1 (Hossain et al., 2006 Mol Cell Biol 26:8191-201), which is a coactivator for nuclear receptors, such as ER-α. Overexpression of miR-125a/b suppressed the activities of two important tyrosine kinase receptors, HER2 and HER3 (Scott 2007 J Biol Chem 282:1479-86), which are often deregulated in breast cancer. Recently, miR-10b has been shown to be associated with progression and metastasis in breast carcinoma (Ma et al., 2007 Nature 449:682-8). The same group also found that miR-31 is inversely correlated with metastasis in breast cancer (Valastyan et al., 2009, Cell 137:1032-46). Another interesting study shows that down-regulation of let-7 miRNAs was observed in breast tumor-initiation cells (BT-IC), and an increased level of let-7 was detected during BT-IC differentiation (Yu 2007, Cell 131:1109-23). Restoration of let-7 in BT-IC reduced proliferation and mammosphere formation in vitro, tumor formation, and metastasis in NOD/SCID mice (Yu 2007, Cell 131:1109-23). However, the detailed mechanisms underlying let-7 regulation in breast tumorigenesis are still unknown.

Previous studies have shown that let-7 sequences are highly conserved in vertebrates and invertebrates. Expression of let-7 miRNAs can be regulated temporally during cancer development (Yu 2007, Cell 131:1109-23) and embryonic development (Grosshans et al., 2005, Dev Cell 8:321-30). For example, expression of let-7 miRNAs increases during differentiation and in mature tissue, but is barely detectable in embryonic stage (Gunaratne 2009, Curr Stem Cell Res Ther 4:168-77). Let-7 is also considered as a tumor suppressor to inhibit malignant growth of cancer cells by targeting RAS (Johnson et al., 2005, Cell 120:635-47), HMGA2 (Lee and Dutta 2005, Genes Dev 21:1025-30, Mayr et al., 2007, Science 15:1576-9), and c-Myc (Kim et al., 2009, Genes Dev 23:1743-8). Reduced expression of let-7 miRNAs has been observed in colon cancer (Michael et al., 2003 Mol Cancer Res 1:882-91), lung cancer (Takamizawa et al., 2004 Cancer Res 64:3753-6), ovary cancer (Dahiya et al., 2008, PLoS One 3:e2436) and breast cancer (Yu 2007, Cell 131:1109-23).

SUMMARY OF THE INVENTION

The present invention provides a method for increasing sensitivity of cancer cells to an antiestrogen agent, such as a selective estrogen receptor modulator (SERM). The method may include identifying a subject that has cancer cells that are resistant to an antiestrogen agent. The antiestrogen agent may be a SERM, such as tamoxifen. The method may further include administering to the subject a polynucleotide in an amount effective to increase the antiestrogen agent sensitivity of the cancer cells compared to the cancer cells before the administering. The cancer cells may be breast cancer cells, ovarian cancer cells, pancreatic cancer cells, endometrial cancer cells, lung cancer cells, or colon cancer cells. The method may further include determining whether the cancer cells are ER-α66 negative or ER-α66 positive prior to the administering. The cancer cells may be ER-α66 positive prior to the administering, or ER-α66negative prior to the administering. The method may further include determining whether the cancer cells are ER-α36 negative or ER-α36 positive prior to the administering. The cancer cells may be ER-α36 positive prior to the administering, or ER-α36 negative prior to the administering. In one embodiment, the cancer cells are ER-α36 positive and ER-α66 negative prior to the administering. In one embodiment, the cancer cells are progesterone receptor negative and Human Epidermal growth factor Receptor 2 (HER2) negative prior to the administering. The method may further include administering an antiestrogen agent, such as a SERM.

The present invention also provides a method for decreasing the amount of estrogen receptor present in a cancer cell. The method may include administering to a subject in need thereof a polynucleotide in an amount effective to decrease the amount of estrogen receptor present in a cancer cell. The cancer cell may be a breast cancer cell, an ovarian cancer cell, a pancreatic cancer cell, an endometrial cancer cell, a lung cancer cell, or a colon cancer cell. The method may further include identifying whether the subject has a cancer cell that is ER-α66 positive or ER-α66 negative. The method may further include identifying whether the subject has a cancer cell that is ER-α36 positive or ER-α36 negative. In one embodiment, the subject as a cancer cell is ER-α66 negative and ER-α36 positive. In one embodiment, the cancer cells are progesterone receptor negative and Human Epidermal growth factor Receptor 2 (HER2) negative prior to the administering. The method may further include administering an antiestrogen agent, such as a SERM.

A polynucleotide used in methods described herein may be substantially complementary to 5'-AACACCAGGAAGGC-CUACCUCA (SEQ ID NO:16). For instance, in one embodiment, between 12 and 17 nucleotides of the polynucleotide are complementary to 5'-AACACCAGGAAGGCCUAC-CUCA (SEQ ID NO:16). In another embodiment, the polynucleotide may be substantially complementary to 5'-UUU-CUAAGUAAUUGCUGCCUCU (SEQ ID NO:6). For instance, in one embodiment, between 15 and 17 nucleotides of the polynucleotide are complementary to 5'-UUUC-UAAGUAAUUGCUGCCUCU (SEQ ID NO:6). In one embodiment the polynucleotide may be between 17 and 26 nucleotides. For instance, the polynucleotide may be chosen from SEQ ID NO:17, SEQ ID NO:18, SEQ ID NO:19, SEQ ID NO:20, SEQ ID NO:21, SEQ ID NO:22, SEQ ID NO:23, SEQ ID NO:24. The polynucleotide may be double stranded or single stranded, and may include ribonucleotides, deoxynucleotides, or be a combination thereof. The polynucleotide may be present in a vector, and the polynucleotide may include one or more modifications. The modifications may be selected from a modified nucleic acid sugar, a modified base, a modified backbone, or a combination thereof. In one embodiment two or more polynucleotides are administered.

The present invention further provides a method for determining whether antiestrogen agent sensitivity of cancer cells in a subject can be increased. Such a method may also be used to evaluate treatment options for a subject having a cancer. The antiestrogen agent may be a SERM, such as tamoxifen. The method may include determining the estrogen receptor status of cancer cells from the subject. For instance, the method may include determining the expression of ER-α66, ER-α36, or the combination thereof. The presence of an antiestrogen agent resistant breast cancer cell that is positive for either ER-α36 or ER-α66 indicates the sensitivity of cancer cells to an antiestrogen agent in a subject can be increased. The method may further include obtaining a biological sample from the subject, wherein the biological sample includes antiestrogen agent resistant cancer cells. The biological sample may be, for instance, blood, plasma, serum, or urine. The cancer cells may be breast cancer cells, ovarian cancer cells, pancreatic cancer cells, endometrial cancer cells, lung cancer cells, or colon cancer cells.

Further provided by the present invention is a method for diagnosing whether a subject has, or is at risk for developing, cancer. The method may include measuring the level of a let-7 miRNA in the biological sample from a subject, wherein an increase in the level of let-7 miRNA in the biological sample relative to the level of the let-7 miRNA in a control sample, indicates the subject has, or is at risk for developing, cancer. The biological sample may be blood, plasma, serum, or urine. The cancer cell may be breast cancer, ovarian cancer, pancreatic cancer, endometrial cancer, lung cancer, or colon cancer. In one embodiment, the cancer is an early stage breast cancer. The cancer may be an estrogen receptor positive cancer, such as ER-α36 positive or ER-α66 positive. The subject may have one or more signs, symptoms, or a combination thereof, of a cancer. The method may further include treating the subject with a polynucleotide described herein in an amount effective to increase the level of the polynucleotide in a cancer cell of the subject.

Also provided by the present invention is a method for identifying an agent that increases the amount of let-7 miRNA in a cell. The method may include exposing a cell to an agent, and measuring the amount of let-7 in the cell, wherein an increase in the amount of let-7 miRNA in the cell compared to the cell not exposed to the agent indicates the agent increases the amount of let-7 miRNA. The cell may be a cancer cell, and may be positive or negative for ER-α36 or ER-α66. In one embodiment the cancer cell is ER-α36 positive, ER-α66 negative, progesterone receptor negative, and HER2 negative. The cancer cell may be a breast cancer cell, an ovarian cancer cell, a pancreatic cancer cell, an endometrial cancer cell, a lung cancer cell, or a colon cancer cell.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 12. A), The expression of HER2, ER-α66, and ER-α36 in commonly used breast cell lines. B), The inverse correlation between the expression of let-7b, let-7i and the expression of ER-α36 in our collected FFPE breast tissues. Confidence Interval (95% CI) on Pearson's Correlation is shown in each chart.

FIG. 18. A nucleotide sequence (SEQ ID NO:1) encoding an ER-α66 polypeptide (SEQ ID NO:2).

FIG. 19. A nucleotide sequence (SEQ ID NO:3) encoding an ER-α36 polypeptide (SEQ ID NO:4).

DETAILED DESCRIPTION OF ILLUSTRATIVE EMBODIMENTS

Polynucleotides

Figure 1:
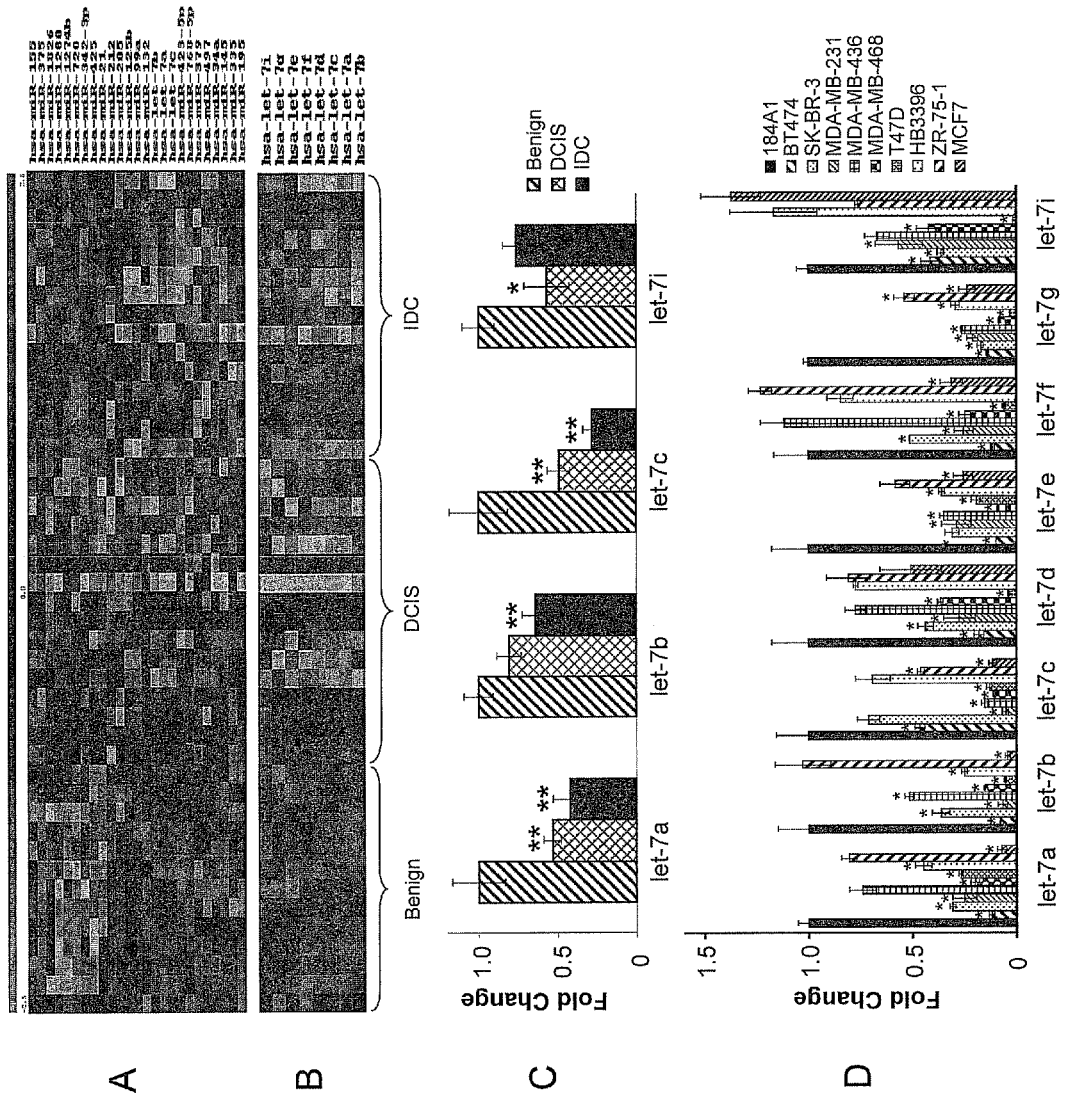
FIG. 1. A), B), heat-map of miRNA microarray of FFPE breast cancer tissues. A), all deregulated miRNAs that reach the $p<0.01$ level. B), let-7 family miRNAs are deregulated in breast cancer tissues, although some of them do not reach the $p<0.01$ level. C), Real-time PCR validation on the expression of let-7a, let-7b, let-7c, and let-7i in the same set of FFPE samples. *, $p<0.05$; **, $p<0.01$. D), Real-time PCR results of let-7 miRNAs in commonly used breast cancer cell lines. Most let-7 miRNAs are down-regulated in breast cancer cell lines in comparison to a benign cell line, 184A1. Cells were collected at three different times and each sample had three technical repeats on PCR plate. *, $p<0.05$.

The invention described herein is based on observations that certain micro RNAs (miRNAs) will alter the expression of estrogen receptor alpha 66 (ER-α66) and/or estrogen receptor alpha 36 (ER-α36) in a cell. As described herein, the inventors have also discovered that the tamoxifen resistance of certain cells can be altered to make the cells more sensitive to tamoxifen. In particular, the inventors have discovered that let-7 miRNAs will decrease the expression of ER-α66 and ER-α36, and, in certain cells, let-7 miRNAs will increase the sensitivity of a cell to tamoxifen.

The present invention includes polynucleotides and the uses thereof. As used herein, the term "polynucleotide" refers to a polymeric form of nucleotides of any length, either ribonucleotides, deoxynucleotides, peptide nucleic acids, or a combination thereof, and includes both single-stranded molecules and double-stranded duplexes. A polynucleotide can be obtained directly from a natural source, or can be prepared with the aid of recombinant, enzymatic, or chemical techniques. A polynucleotide of the present invention may be isolated. An "isolated" polynucleotide is one that has been removed from its natural environment. Polynucleotides that are produced by recombinant, enzymatic, or chemical techniques are considered to be isolated and purified by definition, since they were never present in a natural environment. As used herein, "gene" refers to a nucleotide sequence that encodes an mRNA or an unprocessed RNA (e.g., an RNA molecule that includes both exons and introns and is processed to produce an mRNA, or a pri-miRNA that is processed to produce an miRNA). A gene has at its 5' end a transcription initiation site and a transcription terminator at its 3' end. As used herein, a "target gene" refers to a specific gene whose expression is inhibited by a polynucleotide of the present invention. As used herein, a "target mRNA" is an mRNA encoded by a target gene. Unless noted otherwise, a target gene can result in multiple mRNAs distinguished by the use of different combinations of exons. Such related mRNAs are referred to as splice variants or transcript variants of a gene.

A polynucleotide of the present invention may be referred to as a sense strand. A sense strand has between 17 and 29 nucleotides, for instance, 17, 18, 19, 20, 21, 22, 23, 24, 25, 26, 27, 28, or 29 nucleotides. A sense strand is substantially identical, preferably, identical, to a target mRNA. As used herein, the term "identical" means the nucleotide sequence of the sense strand has the same nucleotide sequence as a portion of a polynucleotide, such as a target mRNA. As used herein, the term "substantially identical" means the sequence of the sense strand differs from the sequence of a target mRNA at 1, 2, 3, 4, 5, 6, 7, 8, 9 or 10 nucleotides, and the remaining nucleotides are identical to the sequence of a polynucleotide, such as a mRNA.

A polynucleotide of the present invention may be referred to as an antisense strand. The antisense strand may be between 17 and 29 nucleotides, for instance, 17, 18, 19, 20, 21, 22, 23, 24, 25, 26, 27, 28, or 29 nucleotides. An antisense strand is substantially complementary, preferably, complementary, to a target mRNA. The term "complementary" refers to the ability of two single stranded polynucleotides to base pair with each other, where an adenine on one polynucleotide will base pair to a thymine or uracil on a second polynucleotide and a cytosine on one polynucleotide will base pair to a guanine on a second polynucleotide. An antisense strand that is "complementary" to another polynucleotide, such as a target mRNA, means the nucleotides of the antisense strand are complementary to a nucleotide sequence of a polynucleotide, such as a target mRNA. As used herein, the term "substantially complementary" means the antisense strand includes 1, 2, 3, 4, 5, 6, 7, 8, 9 or 10 nucleotides that are not complementary to a nucleotide sequence of a polynucleotide, such as a target mRNA. In one embodiment, an antisense strand may include 1, 2, or 3 nucleotides that are unpaired, i.e., they do not have a corresponding complementary nucleotide in the other strand of a polynucleotide, such as a target mRNA (see FIG. 13, where SEQ ID NOs:7-15 each have an unpaired nucleotide relative to the target sequence depicted at SEQ ID NO:16). In one embodiment, a polynucleotide, such as a target mRNA, may include 1, 2, or 3 nucleotides that are unpaired, i.e., they do not have a corresponding complementary nucleotide in an antisense strand of a polynucleotide of the present invention.

The polynucleotides of the present invention also include a double stranded RNA (dsRNA) that includes a sense strand and antisense strand. In one embodiment the two strands of a dsRNA are complementary, and in another embodiment the two strands of a dsRNA are substantially complementary. Polynucleotides of the present invention also include the double stranded DNA polynucleotides that correspond to the dsRNA polynucleotides described herein. In one embodiment, the sense strand and the antisense strand of a double stranded polynucleotide have different lengths (Marques et al., Nat. Biotech., 24:559-565 (2006)). Also included in the present invention are the single stranded RNA polynucleotides and single stranded DNA polynucleotides corresponding to the sense strands and antisense strands disclosed herein. It should be understood that the sequences disclosed herein as DNA sequences can be converted from a DNA sequence to an RNA sequence by replacing each thymidine nucleotide with a uracil nucleotide.

A polynucleotide of the present invention may include overhangs on one or both strands of a double stranded polynucleotide. An overhang is one or more nucleotides present in one strand of a double stranded polynucleotide that are unpaired, i.e., they do not have a corresponding complementary nucleotide in the other strand of the double stranded polynucleotide. An overhang may be at the 3' end of a sense strand, an antisense strand, or both sense and antisense strands. An overhang is typically 1, 2, or 3 nucleotides in length. In one embodiment, the overhang is at the 3' terminus and has the sequence thymine-thymine (or uracil-uracil if it is an RNA). Without intending to be limiting, such an overhang may be used to increase the stability of a dsRNA. If an overhang is present, it is preferably not considered a when determining whether a sense strand is identical or substantially identical to a target mRNA, and it is preferably not considered a when determining whether an antisense strand is complementary or substantially complementary to a target mRNA.

The sense and antisense strands of a double stranded polynucleotide of the present invention may also be covalently attached, for instance, by a spacer made up of nucleotides. Such a polynucleotide is often referred to in the art as a short hairpin RNA (shRNA). Upon base pairing of the sense and antisense strands, the spacer region typically forms a loop. The number of nucleotides making up the loop can vary, and loops between 3 and 23 nucleotides have been reported (Sui et al., Proc. Nat'l. Acad. Sci. USA, 99:5515-5520 (2002), and Jacque et al., Nature, 418:435-438 (2002)). In one embodiment, an shRNA includes a sense strand followed by a nucleotide loop and the analogous antisense strand. In one embodiment, the antisense strand can precede the nucleotide loop structure and the sense strand can follow.

Polynucleotides described herein may be modified. Such modifications can be useful to increase stability of the polynucleotide in certain environments. Modifications can include a nucleic acid sugar, base, or backbone, or any combination thereof. The modifications can be synthetic, naturally occurring, or non-naturally occurring. A polynucleotide of the present invention can include modifications at one or more of the nucleic acids present in the polynucleotide. Examples of backbone modifications include, but are not limited to, phosphonoacetates, thiophosphonoacetates, phosphorothioates, phosphorodithioates, phosphoramidates, methyl phosphonates, chiral-methyl phosphonates, 2-O-methyl ribonucleotides, and peptide-nucleic acids. Examples of nucleic acid base modifications include, but are not limited to, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), or propyne modifications. Examples of nucleic acid sugar modifications include, but are not limited to, 2'-sugar modification, e.g., 2'-O-methyl nucleotides, 2'-deoxy-2'-fluoro nucleotides, 2'-deoxy-2'-fluoroarabino, 2'-O-methoxyethyl nucleotides, 2'-O-trifluoromethyl nucleotides, 2'-O-ethyl-trifluoromethoxy nucleotides, 2'-O-difluoromethoxy-ethoxy nucleotides, or 2'-deoxy nucleotides. Polynucletotides can be obtained commercially synthesized to include such modifications (for instance, Dharmacon Inc., Lafayette, Colo.).

Polynucleotides described herein are biologically active. A biologically active polynucleotide causes the post-transcriptional inhibition of expression, also referred to as silencing, of a target gene. The polynucleotides described herein may be referred to as RNAi, siRNA, shRNA, miRNA, or antisense oligonucleotides. Without intending to be limited by theory, after introduction into a cell a polynucleotide of the present invention will hybridize with a target mRNA if present and signal cellular polypeptides to cleave the target mRNA or to inhibit translation of the target mRNA. The result is the inhibition of expression of the polypeptide encoded by the mRNA. Whether the expression of a target gene is inhibited can be determined, for instance, by measuring a decrease in the amount of the target mRNA in the cell, measuring a decrease in the amount of polypeptide encoded by the mRNA, or by measuring a decrease in the activity of the polypeptide encoded by the mRNA. As used herein, the term "polypeptide" refers broadly to a polymer of two or more amino acids joined together by peptide bonds. The teen "polypeptide" also includes molecules which contain more than one polypeptide joined by a disulfide bond, or complexes of polypeptides that are joined together, covalently or noncovalently, as multimers (e.g., dimers, tetramers). Thus, the terms peptide, oligopeptide, and protein are all included within the definition of polypeptide and these terms are used interchangeably.

An example of a target gene is the gene encoding estrogen receptor-alpha (ER-α). The gene encoding ER-α is located at 6q24-q27, extends over 140 kb, and includes nine exons (Gosden et al., 19865, Cytogenet Cell Genet., 43 (3-4):218-20). The present invention includes polynucleotides that inhibit expression of a polypeptide encoded by ER-α.

ER-α36

One of the polypeptides encoded by the ER-α gene is ER-α36. ER-α36 polypeptides are described in Wang (U.S. Pat. No. 7,745,230), Wang et al., 2005, Biochem Biophys Res Commun 336: 1023-1027, and Wang et al., 2006, Proc Natl Acad Sci USA 103:9063-9068. In one embodiment, a polynucleotide of the present invention is complementary to nucleotides of a target ER-α36 mRNA. In one embodiment, a polynucleotide of the present invention includes nucleotides that are not complementary to nucleotides of a target ER-α36 mRNA, e.g., the polynucleotide of the present invention is substantially complementary to a target ER-α36 mRNA. The nucleotides in the target may be consecutive nucleotides. One example of a target mRNA encoding ER-α36 is depicted at SEQ ID NO:3 (FIG. 19, see also Genbank accession number BX640939). Other mRNA polynucleotides encoding ER-α36 having different nucleotide sequences may also be the target of a polynucleotide of the present invention. For example, the mRNA depicted at SEQ ID NO:3 is but one member of the class of nucleotide sequences encoding a polypeptide having the amino acid sequence SEQ ID NO:4. The class of nucleotide sequences encoding SEQ ID NO:4 is large but finite, and the nucleotide sequence of each member of the class can be readily determined by one skilled in the art by reference to the standard genetic code, wherein different nucleotide triplets (codons) are known to encode the same amino acid. Other mRNA polynucleotides encoding ER-α36 are also available in databases, and others can be readily identified in cells using routine methods that do not require undue experimentation.

The nucleotides to which a polynucleotide of the present invention hybridize in a target mRNA may be part of the 5' untranslated region (5' UTR), the coding region, the 3' untranslated region (3' UTR), or a combination thereof (e.g., part of the 5' UTR and the coding region, or part of the coding region and the 3' UTR). As used herein, a "coding region" and "coding sequence" are used interchangeably and refer to a nucleotide sequence that is translated into a polypeptide. A coding region includes a translation initiation codon at the 5' end and a translation stop codon at the 3' end. In the example of the target ER-α36 mRNA shown at SEQ ID NO:3, the 5' UTR corresponds to nucleotides 1-233, the coding region corresponds to nucleotides 234-1166, and the 3' UTR corresponds to nucleotides 1167-5439.

In one embodiment, a polynucleotide of the present invention may be complementary to nucleotides of a target ER-α36 mRNA. Without intending to be limited by theory, it is expected that a polynucleotide of the present invention that is complementary to nucleotides of a target mRNA, such as the nucleotides of an mRNA encoding an ER-α36 polypeptide, will hybridize with a target mRNA and signal cellular endonucleases to cleave the target mRNA. The result is the inhibition of expression of the polypeptide encoded by the mRNA. Such an inhibitory polynucleotide is often referred to as an siRNA. In some embodiments, a polynucleotide of the present invention that is complementary to the target mRNA will hybridize with nucleotides that correspond to the coding region, for instance, nucleotides 234-1166 of SEQ ID NO:3. Examples of siRNAs that can be used to silence expression of ER-α36 may be found in Zhang et al., 2011, Oncogene, 30 (7):770-780, and Kang et al., 2010, Mol. Endocrinol., 24 (4):709-721.

Figure 13:
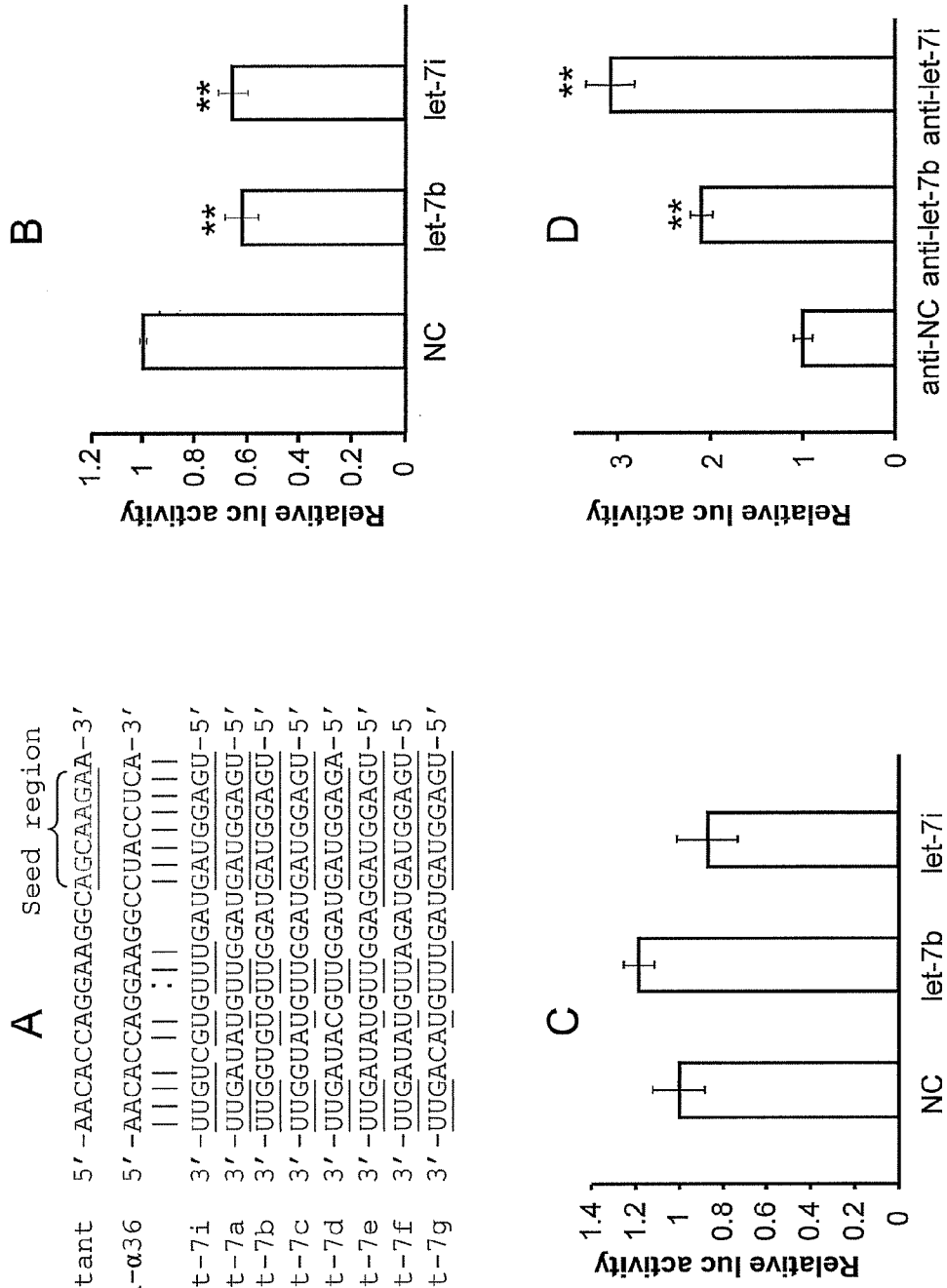
FIG. 13. Let-7 miRNAs target ER-α36. A), let-7 target prediction: The pairing between let-7 miRNAs and 3'UTR of ER-α36 mRNAs. The paired nucleotides are underlined. The mutated nucleotides in luciferase assays are underlined in the sequence marked "Mutant." Mutant, SEQ ID NO:15; ER-α36, SEQ ID NO:16; let-7i, SEQ ID NO:14; let-7a, SEQ ID NO:7; let-7b, SEQ ID NO:8; let-7c, SEQ ID NO:9; let-7d, SEQ ID NO:10; let-7e, SEQ ID NO:11; let-7f, SEQ ID NO:12; and let-7g, SEQ ID NO:13. B), let-7b and let-7i significantly inhibited the luciferase activity when the ER-α36 binding site was in the 3' UTR of the luciferase gene in MCF7 cells. C), they did not show inhibition when a mutated sequence was inserted into the 3' UTR of luciferase in MCF7 cells. D), anti-let7b and anti-let7i strongly induced luciferase activity when the putative binding site was inserted into the 3' UTR of luciferase in 184A1 cells. **, $p<0.01$.

In one embodiment, a polynucleotide of the present invention may be substantially complementary to a target ER-α36 mRNA. Without intending to be limited by theory, it is expected that a polynucleotide of the present invention that is substantially complementary to nucleotides of a target mRNA, such as the nucleotides of an mRNA encoding an ER-α36 polypeptide, will hybridize with a target mRNA and inhibit translation of the target mRNA. The result is the inhibition of expression of the polypeptide encoded by the mRNA. Such an inhibitory polynucleotide is often referred to as a miRNA (Barh et al., 2010, Curr. Oncol., 17:70-80). When the polynucleotide of the present invention is substantially complementary to a target ER-α36 mRNA, the target nucleotides may be located in the 5'UTR, the coding region, or the 3' UTR. In one embodiment, the target nucleotides are located in the 3'UTR. An example of a target within a 3' UTR of an mRNA encoding a ER-α36 polypeptide is 5'-AACACCAG-GAAGGCCUACCUCA (SEQ ID NO:16). Examples of polynucleotides targeting 5'-AACACCAGGAAGGCCUAC-CUCA (SEQ ID NO:16) that are substantially complementary to the target include the following: 3'-UUGUCGUGU-UUGAUGAUGGAGU-5' (SEQ ID NO:14), 3'-UUGAUAUGUUGGAUGAUGGAGU-5' (SEQ ID NO:7), 3'-UUGGUGUGUUGGAUGAUGGAGU-5' (SEQ ID NO:8), 3'-UUGGUAUGUUGGAUGAUGGAGU-5' (SEQ ID NO:9), 3'-UUGAUACGUUGGAUGAUGGAGA-5' (SEQ ID NO:10), 3'-UUGAUAUGUUGGAGGAUG-GAGU-5' (SEQ ID NO:11), 3'-UUGAUAUGUUA-GAUGAUGGAGU-5 (SEQ ID NO:12), and 3'-UUGACAUGUUUGAUGAUGGAGU-5' (SEQ ID NO:13). As can be seen at FIG. 13, polynucleotides with biological activity, e.g., that acted to inhibit the expression of ER-α36, included between 5 and 10 out of 22 nucleotides that were not complementary to the target. Further, the location of the complementary nucleotides was largely in defined regions. In some embodiments, the AG of an RNA duplex between an antisense strand of a polynucleotide of the present invention and a target ER-α36 mRNA is between −6.0 kcal/mole and −40 kcal/mole, and in one embodiment is −15.8 kcal/mole. Methods for measuring the ΔG of an RNA duplex are known and routine (see Zuker et al., 1999, In: RNA Biochemistry and Biotechnology, Barciszewski and Clark, eds., NATO ASI Series, Kluwer Academic Publishers).

In one embodiment, a polynucleotide of the present invention may have identity with SEQ ID NO:7, SEQ ID NO:8, SEQ ID NO:9, SEQ ID NO:10, SEQ ID NO:11, SEQ ID NO:12, SEQ ID NO:13, or SEQ ID NO:14. As used herein, "identity" refers to sequence similarity between two polynucleotides. The sequence similarity between two polynucleotides is determined by aligning the residues of the two polynucleotides (e.g., a candidate nucleotide sequence and a reference nucleotide sequence, such as SEQ ID NO:7) to optimize the number of identical nucleotides along the lengths of their sequences; gaps in either or both sequences are permitted in making the alignment in order to optimize the number of shared nucleotides, although the nucleotides in each sequence must nonetheless remain in their proper order. The sequence similarity is typically at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. Sequence similarity may be determined, for example, using sequence techniques such as GCG FastA (Genetics Computer Group, Madison, Wis.), MacVector 4.5 (Kodak/IBI software package) or other suitable sequencing programs or methods known in the art. Preferably, sequence similarity between two nucleotide sequences is determined using the Blastn program of the BLAST search algorithm, available through the World Wide Web, for instance at the internet site maintained by the National Center for Biotechnology Information, National Institutes of Health. Preferably, the default values for all Blastn search parameters are used. In the comparison of two nucleotide sequences using the BLAST search algorithm, sequence similarity is referred to as "identities."

Other examples of polynucleotides that may be used in the methods described herein to target ER-α36 mRNAs include let-7 miRNAs. As used herein, the term "let-7" refers to small non-coding regulatory RNAs. Examples of let-7 miRNAs include the polynucleotide encoding the C. elegans let-7 (TGAGGTAGTAGGTTGTATAGTT (SEQ ID NO:25) GenBank accession number AY390762), and the polynucleotides encoding human let-7 family members including, but not limited to, the polynucleotides disclosed at Genbank accession numbers AJ421724, AJ421725, AJ421726, AJ421727, AJ421728, AJ421729, AJ421730, AJ421731, AJ421732.

A let-7 miRNA may be a mature miRNA, which is a single-stranded RNA molecule of 17, 18, 19, 20, 21, 22, 23, 24, 25, 26, 27, 28, or 29 nucleotides in length. In some embodiments, a mature miRNA is 21-23 nucleotides in length. miRNAs themselves are encoded by genes that are transcribed but not translated into protein; instead they are processed from primary transcripts known as pri-miRNA to short stem-loop structures called pre-miRNA and finally to functional miRNA. miRNA sequences have been described in Vella and Slack, 2005, In: WormBook, ed. The C. elegans Research Community, WormBook, doi/10.1895/wormbook.1.26.1, Lim, et al., 2003, Genes & Development, 17:991-1008, Lim et al., 2003, Science 299:1540, Lee and Ambros 2001, Science, 294:862, and Lau et al., 2001, Science 294:858-861. A mature miRNA is produced as a result of a series of miRNA maturation steps. First a gene encoding the miRNA is transcribed. The gene encoding the miRNA is typically much longer than the processed mature miRNA molecule; miRNAs are first transcribed as primary transcripts or "pri-miRNA" with a cap and poly-A tail, which is subsequently processed to short, about 70-nucleotide "stem-loop structures" known as "pre-miRNA" in the cell nucleus (Lieberman et al., U.S. Published Patent Application 2010/0310583).

The term "pri-miRNA" refers to a precursor to a mature miRNA molecule which includes an miRNA sequence and a stem-loop component which are both flanked by microRNA flanking sequences, where each flanking sequence typically ends in either a cap or poly-A tail. A pri-microRNA, is composed of any type of nucleic acid based molecule capable of accommodating the microRNA flanking sequences and the microRNA sequence. The nucleotide sequence of the pri-miRNA precursor and its stem-loop components can vary widely. In one aspect a pre-miRNA molecule can be an isolated nucleic acid, including microRNA flanking sequences and a stem-loop structure and a microRNA sequence incorporated therein. A pri-miRNA molecule can be processed in vivo or in vitro to an intermediate "pre-miRNA," which is further processed to produce a mature miRNA.

The term "pre-miRNA" refers to the intermediate miRNA species in the processing of a pri-miRNA to mature miRNA, where pri-miRNA is processed to pre-miRNA in the nucleus, where upon pre-miRNA translocates to the cytoplasm where it undergoes additional processing in the cytoplasm to form mature miRNA. Pre-miRNAs are generally about 70 nucleotides long, but can be less than 70 nucleotides or more than 70 nucleotides.

A let-7 miRNA may include miRNA flanking sequences, e.g., nucleotide sequences including miRNA processing elements. miRNA processing elements are the minimal nucleic acid sequences which contribute to the production of mature miRNA from precursor miRNA. These elements may be located within a 40 nucleotide sequence that flanks an mRNA stem-loop structure. In some instances the miRNA processing elements are found within a stretch of nucleotide sequences of between 5 and 4,000 nucleotides in length that flank a miRNA stem-loop structure. Thus, in some embodiments the flanking sequences are 5-4,000 nucleotides in length. As a result, the length of the precursor molecule can be, in some instances at least about 150 nucleotides or 270 nucleotides in length. The total length of the precursor molecule, however, can be greater or less than these values. In other embodiments the minimal length of the miRNA flanking sequence is 10, 20, 30, 40, 50, 60, 70, 80, 90, 100, 150, 200 and any integer there between. In other embodiments the maximal length of the miRNA flanking sequence is 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900 4,000 and any integer there between.

ER-α66

One of the polypeptides encoded by the ER-α gene is ER-α66. In one embodiment, a polynucleotide of the present invention is complementary to nucleotides of a target ER-α66 mRNA. In one embodiment, a polynucleotide of the present invention includes nucleotides that are substantially complementary to a target ER-α66 mRNA. The nucleotides in the target may be consecutive nucleotides. One example of a target mRNA encoding ER-α66 is depicted at SEQ ID NO:1 (FIG. 18, see also Genbank accession number X03635. Other mRNA polynucleotides encoding ER-α66 having different nucleotide sequences may also be the target of a polynucleotide of the present invention. For example, the mRNA depicted at SEQ ID NO:1 is but one member of the class of nucleotide sequences encoding a polypeptide having the amino acid sequence SEQ ID NO:2. The class of nucleotide sequences encoding SEQ ID NO:2 is large but finite, and the nucleotide sequence of each member of the class can be readily determined by one skilled in the art by reference to the standard genetic code, wherein different nucleotide triplets (codons) are known to encode the same amino acid. Other mRNA polynucleotides encoding ER-α66 are also available in databases, and others can be readily identified in cells using routine methods that do not require undue experimentation.

The nucleotides to which a polynucleotide of the present invention hybridize in a target mRNA may be part of the 5' UTR, the coding region, the 3' UTR, or a combination thereof (e.g., part of the 5' UTR and the coding region, or part of the coding region and the 3' UTR). In the example of the target ER-α66 mRNA shown at SEQ ID NO:1, the 5' UTR corresponds to nucleotides 1-360 the coding region corresponds to nucleotides 361-2148 and the 3' UTR corresponds to nucleotides 2149-6434.

In one embodiment, a polynucleotide of the present invention may be complementary to nucleotides of a target ER-α66 mRNA. Without intending to be limited by theory, it is expected that a polynucleotide of the present invention that is complementary to nucleotides of a target mRNA, such as the nucleotides of an mRNA encoding an ER-α66 polypeptide, will hybridize with a target mRNA and signal cellular endonucleases to cleave the target mRNA. The result is the inhibition of expression of the polypeptide encoded by the mRNA. Such an inhibitory polynucleotide is often referred to as an siRNA. In some embodiments, a polynucleotide of the present invention that is complementary to the target mRNA will hybridize with nucleotides that correspond to the coding region, for instance, nucleotides 293-2080 of SEQ ID NO:1.

Figure 5:
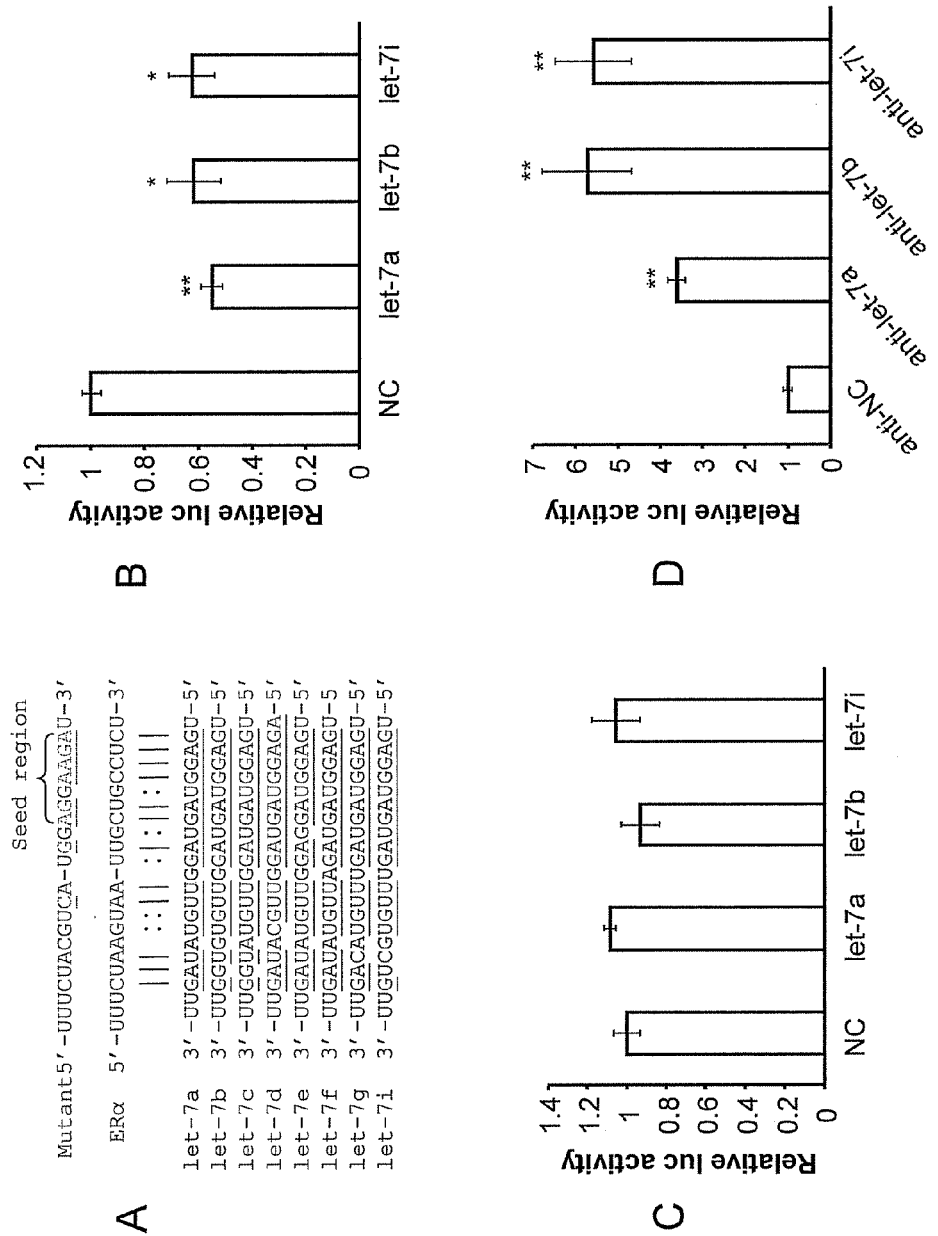
FIG. 5. Let-7 microRNAs target ER-α. A), let-7 target prediction: The pairing between let-7 miRNAs and 3'UTR of ER-α mRNAs. The paired nucleotides are underlined. The mutated nucleotides in luciferase assays are underlined in the sequence marked "Mutant." Mutant, SEQ ID NO:5; ERa, SEQ ID NO:6; let-7a, SEQ ID NO:7; let-7b, SEQ ID NO:8; let-7c, SEQ ID NO:9; let-7d, SEQ ID NO:10; let-7e, SEQ ID NO:11; let-7f, SEQ ID NO:12; let-7g, SEQ ID NO:13; and let-7i, SEQ ID NO:14. B), C), D), let-7 directly regulates ER-α as demonstrated by the luciferase reporter assay. NC, negative control #1 miRNA. B), let-7a, let-7b, and let-7i significantly inhibited the luciferase activity when the ER-α binding site was in the 3'UTR of the luciferase gene in MCF7 cells. C), they did not show inhibition when a mutated sequence was inserted into the 3'UTR of luciferase in MCF7 cells. D), anti-let-7a, anti-let7b, and anti-let7i strongly induced luciferase activity when the putative binding site was inserted into the 3' UTR of luciferase in 184A1 cells.

In one embodiment, a polynucleotide of the present invention may be substantially complementary to a target ER-α66 mRNA. Without intending to be limited by theory, it is expected that a polynucleotide of the present invention that is substantially complementary to nucleotides of a target mRNA, such as the nucleotides of an mRNA encoding an ER-α66 polypeptide, will hybridize with a target mRNA and inhibit translation of the target mRNA. The result is the inhibition of expression of the polypeptide encoded by the mRNA. Such an inhibitory polynucleotide is often referred to as an miRNA. When the polynucleotide of the present invention is substantially complementary to a target ER-α66 mRNA, the target nucleotides may be located in the 5' UTR, the coding region, or the 3' UTR. In one embodiment, the target nucleotides are located in the 3' UTR. An example of a target within a 3' UTR of an mRNA encoding a ER-α66 polypeptide is 5'-UUUCUAAGUAAUUGCUGCCUCU (SEQ ID NO:6). Examples of polynucleotides targeting 5'-UUUCUAAGUAAUUGCUGCCUCU (SEQ ID NO:6) that are not completely complementary to the target include the following: 3'-UUGAUAUGUUGGAUGAUGGAGU-5' (SEQ ID NO:7), 3'-UUGGUGUGUUGGAUGAUGGAGU-5' (SEQ ID NO:8), 3'-UUGGUAUGUUGGAUGAUG-GAGU-5' (SEQ ID NO:9), 3'-UUGAUACGUUG-GAUGAUGGAGA-5' (SEQ ID NO:10), 3'-UUGAUAUGUUGGAGGAUGGAGU-5' (SEQ ID NO:11), 3'-UUGAUAUGUUAGAUGAUGGAGU-5 (SEQ ID NO:12), 3'-UUGACAUGUUUGAUGAUGGAGU-5' (SEQ ID NO:13), and 3'-UUGUCGUGUUUGAUGAUG-GAGU-5' (SEQ ID NO:14). As can be seen at FIG. 5, polynucleotides with biological activity, e.g., that acted to inhibit the expression of ER-α66, included between 5 and 7 out of 22 nucleotides that were not complementary to the target. Further, the location of the complementary nucleotides was largely in defined regions. In some embodiments, the ΔG of an RNA duplex between an antisense strand of a polynucleotide of the present invention and a target ER-α66 mRNA is between −6.0 kcal/mole and −40 kcal/mole, and in one embodiment is −16.2 kcal/mole.

In one embodiment, a polynucleotide of the present invention may have identity with SEQ ID NO:7, SEQ ID NO:8, SEQ ID NO:9, SEQ ID NO:10, SEQ ID NO:11, SEQ ID NO:12, SEQ ID NO:13, or SEQ ID NO:14.

Other examples of polynucleotides that may be used in the methods described herein to target ER-α36 mRNAs include let-7 miRNAs. Examples of let-7 miRNAs are described herein.

Methods of Making

The polynucleotides described herein, e.g., a polynucleotide having identity, substantial identity, complementarity, or substantial complementarity to a target mRNA, or a let-7 miRNA, can be designed using methods that are routine and known in the art. For instance, polynucleotides that inhibit the expression of an ER-α36 or ER-α66 polypeptide may be identified by the use of cell lines and/or primary cells. A candidate polynucleotide is the polynucleotide that is being tested to determine if it decreases expression of an ER-α36 or ER-α66 polypeptide. Other methods are known in the art and used routinely for designing and selecting candidate polynucleotides. Candidate polynucleotides are typically screened using publicly available algorithms (e.g., BLAST) to compare the candidate polynucleotide sequences with mRNA sequences. Those that are likely to form a duplex with an mRNA expressed by a non-target coding region are typically eliminated from further consideration. The remaining candidate polynucleotides may then be tested to determine if they inhibit expression of one of the polypeptides described herein.

In general, candidate polynucleotides are individually tested by introducing a candidate polynucleotide into a cell that expresses the appropriate polypeptide. The candidate polynucleotides may be prepared in vitro and then introduced into a cell. The candidate polynucleotides may also be prepared by introducing into a cell a construct that encodes the candidate polynucleotide. Such constructs are known in the art and include, for example, a vector encoding and expressing a sense strand and an antisense strand of a candidate polynucleotide, and RNA expression vectors that include the sequence encoding the sense strand and an antisense strand of a candidate polynucleotide flanked by operably linked regulatory sequences, such as an RNA polymerase III promoter and an RNA polymerase III terminator, that result in the production of an RNA polynucleotide.

A cell that can be used to evaluate a candidate polynucleotide may be a cell that expresses the appropriate polypeptide. A cell can be ex vivo or in vivo. As used herein, the teen "ex vivo" refers to a cell that has been removed from the body of a subject. Ex vivo cells include, for instance, primary cells (e.g., cells that have recently been removed from a subject and are capable of limited growth in tissue culture medium), and cultured cells (e.g., cells that are capable of extended culture in tissue culture medium). As used herein, the term "in vivo" refers to a cell that is within the body of a subject. For instance, an in vivo cell may be a cell present in an organ or a tumor. A cell may be obtained from a subject by, for example, biopsy of human breast tissue.

Examples of readily available cells expressing an ER-α36 polypeptide and an ER-α66 polypeptide include cultured cells such as, but not limited to, T47D, HB3396, and ZR-75-1 cell lines. Examples of readily available cells expressing an ER-α36 polypeptide and not expressing an ER-α66 polypeptide include cultured cells such as, but not limited to, SK-BR-3, MDA-MB-231, MDA-MB-436, and MDA-MB-468 cell lines. An example of a readily available cell expressing an ER-α66 polypeptide and expressing an ER-α36 polypeptide at trace levels includes MCF7 cells. Sources of other suitable cells include primary cells obtained from biopsy, such as cells present in a breast cancer tumor, ovarian cancer tumor, pancreatic cancer tumor, endometrial cancer tumor, lung cancer tumor, or some colon cancer tumors, or lymph nodes draining tissues harboring such tumors. Other cells can also be modified to express one of the polypeptides by introducing into a cell a vector having a polynucleotide encoding the polypeptide.

Candidate polynucleotides may also be tested in animal models. The study of various cancers in animal models (for instance, mice) is a commonly accepted practice for the study of cancers. For instance, the nude mouse model, where human tumor cells are injected into the animal, is commonly accepted as a general model useful for the study of a wide variety of cancers. Candidate polynucleotides can be used in this and other animal models to determine if a candidate polynucleotide decreases one or more symptoms and/or signs associated with disease.

Methods for introducing a candidate polynucleotide into a cell, including a vector encoding a candidate polynucleotide, are known in the art and routine. When the cells are ex vivo, such methods include, for instance, transfection with a delivery reagent, such as lipid or amine based reagents, including cationic liposomes or polymeric DNA-binding cations (such as poly-L-lysine and polyethyleneimine). Alternatively, electroporation or viral transfection can be used to introduce a candidate polynucleotide, or a vector encoding a candidate polynucleotide. When the cells are in vivo, such methods include, but are not limited to, local or intravenous administration.

When evaluating whether a candidate polynucleotide functions to inhibit expression of one of the polypeptides described herein, the amount of target mRNA in a cell containing a candidate polynucleotide can be measured and compared to the same type of cell that does not contain the candidate polynucleotide. Methods for measuring mRNA levels in a cell are known in the art and routine. Such methods include quantitative reverse-transcriptase polymerase chain reaction (RT-PCR). Primers and specific conditions for amplification of an mRNA encoding an ER-α36 or an ER-α66 polypeptide can be readily determined by the skilled person. An example of useful primers for RT-PCR includes 5'-CAAGTGGTTTCCTCGTGTCTAAAG (SEQ ID NO:35) and 5'-ACGTCCACACACGGATTTGA (SEQ ID NO:36) for ER-α36 and 5'-GCGGCCACGGACCAT (SEQ ID NO:37) and 5'-TTCCCTTGGATCTGATGCAGTA (SEQ ID NO:38) for ER-α66. Another methods includes reporter systems that use a detectable marker such as luciferase. A reporter system with an appropriate target sequence (for instance, SEQ ID NOs: 41 and 42 for ER-α36, or SEQ ID NOs:39 and 40 for ER-α66 can be used as described in Examples 1 and 2. Other methods include, for instance, Northern blotting, and array analysis.

Other methods for evaluating whether a candidate polynucleotide functions to inhibit expression of one of the polypeptides described herein include monitoring the polypeptide. For instance, assays can be used to measure a decrease in the amount of polypeptide encoded by the mRNA, or to measure a decrease in the activity of the polypeptide encoded by the mRNA. Methods for measuring a decrease in the amount of a polypeptide include assaying for the polypeptide present in cells containing a candidate polynucleotide and comparing to the same type of cell that does not contain the candidate polynucleotide. Whether a cell expresses one of the polypeptides can be determined using methods that are routine and known in the art including, for instance, Western immunoblot, ELISA, immunoprecipitation, or immunohistochemistry. Western immunoblot and immunoprecipitation are generally used with ex vivo cells, and immunohistochemistry is generally used with in vivo cells.

A candidate polynucleotide that is able to decrease the expression of an ER-α36 or an ER-α66 polypeptide by at least 20%, at least 30%, at least 40%, at least 50%, at least 60%, at least 70%, at least 80%, at least 90% or 100% when compared to a control cell, is considered to be a polynucleotide of the present invention.

A polynucleotide of the present invention can be present in a vector. A vector is a replicating polynucleotide, such as a plasmid, phage, or cosmid, to which another polynucleotide may be attached so as to bring about the replication of the attached polynucleotide. Construction of vectors containing a polynucleotide of the invention employs standard ligation techniques known in the art. See, e.g., Sambrook et al, *Molecular Cloning: A Laboratory Manual.*, Cold Spring Harbor Laboratory Press (1989). A vector can provide for further cloning (amplification of the polynucleotide), i.e., a cloning vector, or for expression of the polynucleotide, i.e., an expression vector. The term vector includes, but is not limited to, plasmid vectors, viral vectors, cosmid vectors, transposon vectors, and artificial chromosome vectors. Examples of viral vectors include, for instance, adenoviral vectors, adeno-associated viral vectors, lentiviral vectors, retroviral vectors, and herpes virus vectors. A vector may result in integration into a cell's genomic DNA. A vector may be capable of replication in a bacterial host, for instance *E. coli*. Preferably the vector is a plasmid. A polynucleotide of the present invention can be present in a vector as two separate complementary polynucleotides, each of which can be expressed to yield a sense and an antisense strand of a dsRNA, or as a single polynucleotide containing a sense strand, an intervening spacer region, and an antisense strand, which can be expressed to yield an RNA polynucleotide having a sense and an antisense strand of the dsRNA.

Selection of a vector depends upon a variety of desired characteristics in the resulting construct, such as a selection marker, vector replication rate, and the like. Suitable host cells for cloning or expressing the vectors herein are prokaryotic or eukaryotic cells. Suitable eukaryotic cells include mammalian cells, such as murine cells and human cells. Suitable prokaryotic cells include eubacteria, such as gram-negative organisms, for example, *E. coli*.

An expression vector optionally includes regulatory sequences operably linked to the polynucleotide of the present invention. A "regulatory sequence" is a nucleotide sequence that regulates expression of a coding sequence to which it is operably linked. Nonlimiting examples of regulatory sequences include promoters, enhancers, transcription initiation sites, translation start sites, translation stop sites, transcription terminators, and poly(A) signals. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

Vectors may include constitutive, inducible, and/or tissue specific promoters for expression of a polynucleotide of the present invention in a particular tissue or intracellular environment, examples of which are known to one of ordinary skill in the art. Constitutive mammalian promoters include, but are not limited to, polymerase promoters as well as the promoters for the following genes: hypoxanthine phosphoribosyl transferase (HPTR), adenosine deaminase, pyruvate kinase, and β-actin. Exemplary viral promoters which function constitutively in eukaryotic cells include, but are not limited to, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex Other constitutive promoters are known to those of ordinary skill in the art.

Inducible promoters are expressed in the presence of an inducing agent and include, but are not limited to, metal-inducible promoters and steroid-regulated promoters. For example, the metallothionein promoter is induced to promote transcription in the presence of certain metal ions. Other inducible promoters are known to those of ordinary skill in the art.

Examples of tissue-specific promoters include, but are not limited to, the promoter for creatine kinase, which has been used to direct expression in muscle and cardiac tissue and immunoglobulin heavy or light chain promoters for expression in B cells. Other tissue specific promoters include the human smooth muscle α-actin promoter. Exemplary tissue-specific expression elements for the liver include but are not limited to HMG-COA reductase promoter, sterol regulatory element 1, phosphoenol pyruvate carboxy kinase (PEPCK) promoter, human C-reactive protein (CRP) promoter, human glucokinase promoter, cholesterol L 7-alpha hydroylase (CYP-7) promoter, beta-galactosidase alpha-2,6 sialylkansferase promoter, insulin-like growth factor binding protein (IGFBP-1) promoter, aldolase B promoter, human transferrin promoter, and collagen type I promoter. Exemplary tissue-specific expression elements for the pancreas include but are not limited to pancreatitis associated protein promoter (PAP), elastase 1 transcriptional enhancer, pancreas specific amylase and elastase enhancer promoter, and pancreatic cholesterol esterase gene promoter. Exemplary tissue-specific expression elements for the endometrium include, but are not limited to, the uteroglobin promoter. Exemplary tissue-specific expression elements for lymphocytes include, but are not limited to, the human CGL-1/granzyme B promoter, the terminal deoxy transferase (TdT), lambda 5, VpreB, and lck (lymphocyte specific tyrosine protein kinase p561ck) promoter, the humans CD2 promoter and its 3' transcriptional enhancer, and the human NK and T cell specific activation (NKG5) promoter. Exemplary tissue-specific expression elements for the colon include, but are not limited to, pp60c-src tyrosine kinase promoter, organ-specific neoantigens (OSNs) promoter, and colon specific antigen-P promoter. Exemplary tissue-specific expression elements for breast cells include, but are not limited to, the human alpha-lactalbumin promoter. Exemplary tissue-specific expression elements for the lung include, but are not limited to, the cystic fibrosis transmembrane conductance regulator (CFTR) gene promoter.

The polynucleotide of the present invention also typically includes a transcription terminator. Suitable transcription terminators are known in the art and include, for instance, a stretch of 5 consecutive thymidine nucleotides.

Polynucleotides described herein can be produced in vitro or in vivo. For instance, methods for in vitro synthesis include, but are not limited to, chemical synthesis with a conventional DNA/RNA synthesizer. Commercial suppliers of synthetic polynucleotides and reagents for in vitro synthesis are well known. Methods for in vitro synthesis also include, for instance, in vitro transcription using a circular or linear expression vector in a cell free system. Expression vectors can also be used to produce a polynucleotide of the present invention in a cell, and the polynucleotide may then be isolated from the cell.

Compositions

The present invention is also directed to compositions including one or more polynucleotides described herein. Such compositions typically include a pharmaceutically acceptable carrier. As used herein "pharmaceutically acceptable carrier" includes saline, solvents, dispersion media, coatings, antibacterial and antifungal agents, isotonic and absorption delaying agents, and the like, compatible with pharmaceutical administration. Additional active compounds can also be incorporated into the compositions.

A composition may be prepared by methods well known in the art of pharmacy. In general, a composition can be formulated to be compatible with its intended route of administration. Administration may be systemic or local. In some aspects local administration may have advantages for site-specific, targeted disease management. Local therapies may provide high, clinically effective concentrations directly to the treatment site, without causing systemic side effects. Examples of routes of administration include parenteral, e.g., intravenous, intradermal, subcutaneous, oral, transdermal (topical), and transmucosal administration. Solutions or suspensions can include the following components: a sterile diluent such as water for administration, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; electrolytes, such as sodium ion, chloride ion, potassium ion, calcium ion, and magnesium ion, and agents for the adjustment of tonicity such as sodium chloride or dextrose. pH can be adjusted with acids or bases, such as hydrochloric acid or sodium hydroxide. A composition can be enclosed in ampoules, disposable syringes or multiple dose vials made of glass or plastic.

Compositions can include sterile, aqueous solutions or dispersions and sterile powders for the extemporaneous preparation of sterile solutions or dispersions. For intravenous administration, suitable carriers include physiological saline, bacteriostatic water, Cremophor EL™ (BASF, Parsippany, N.J.) or phosphate buffered saline. A composition is typically sterile and, when suitable for injectable use, should be fluid to the extent that easy syringability exists. It should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile solutions can be prepared by incorporating the active compound (e.g., a polynucleotide of the present invention) in the required amount in an appropriate solvent with one or a combination of ingredients enumerated above, as required, followed by filtered sterilization. Generally, dispersions are prepared by incorporating the active compound into a sterile vehicle, which contains a dispersion medium and the required other ingredients from those enumerated above. In the case of sterile powders for the preparation of sterile injectable solutions, methods of preparation that may be used include vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier. Pharmaceutically compatible binding agents can be included as part of the composition. The tablets, pills, capsules, troches and the like may contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. An example of transdermal administration includes iontophoretic delivery to the dermis or to other relevant tissues.

The active compounds can also be administered by any method suitable for administration of polynucleotide agents, e.g., using gene guns, bio-injectors, and skin patches as well as needle-free methods such as the micro-particle DNA vaccine technology disclosed by Johnston et al. (U.S. Pat. No. 6,194,389). Additionally, intranasal delivery is possible, as described in, for instance, Hamajima et al. Clin. Immunol. Immunopathol., 88, 205-210 (1998). Delivery reagents such as lipids, cationic lipids, phospholipids, liposomes, and microencapsulation may also be used.

The active compounds may be prepared with carriers that will protect the compound against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially. Liposomal suspensions can also be used as pharmaceutically acceptable carriers. These can be prepared according to methods known to those skilled in the art.

A polynucleotide described herein may be used in combination with other agents assisting the cellular uptake of polynucleotides, or assisting the release of poylnucleotides from endosomes or intracellular compartments into the cytoplasm or cell nuclei by, for instance, conjugation of those to the polynucleotide. The agents may be, but are not limited to, peptides, especially cell penetrating peptides, protein transduction domains, and/or dsRNA-binding domains which enhance the cellular uptake of polynucleotides (Dowdy et al., US Published Patent Application 2009/0093026, Eguchi et al., 2009, *Nature Biotechnology* 27:567-571, Lindsay et al., 2002, Curr. Opin. Pharmacol., 2:587-594, Wadia and Dowdy, 2002, Curr. Opin. Biotechnol. 13:52-56. Gait, 2003, Cell. Mol. Life. Sci., 60:1-10). The conjugations can be performed at an internal position at the oligonucleotide or at a terminal positions either the 5'-end or the 3'-end.

Toxicity and therapeutic efficacy of such active compounds can be determined by standard pharmaceutical procedures in cell cultures or experimental animals, e.g., for determining the $ED_{50}$ (the dose therapeutically effective in 50% of the population).

The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For a compound used in the methods of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of signs and/or symptoms) as determined in cell culture. Such information can be used to more accurately determine useful doses in humans.

The compositions can be administered one or more times per day to one or more times per week, including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with an effective amount of a polynucleotide can include a single treatment or can include a series of treatments.

Methods of Use

The present invention is further directed to methods of using the polynucleotides described herein. Without intending to be limited by theory, it is believed that polynucleotides described herein mediate RNA interference (RNAi) of a mRNA polynucleotide that encodes ER-α66 or ER-α36. RNAi is the process of sequence-specific, post-transcriptional gene silencing in animals and plants, initiated by double-stranded RNA (dsRNA) that includes an antisense strand that is complementary or substantially complementary in sequence to a portion of the silenced mRNA. Silencing can result from degradation of mRNA, which often occurs when there is high complementarity between one strand of a dsRNA and a target mRNA. Silencing can also result from translational repression or deadenylation, which often occurs when there is partial complementarity between one strand of a dsRNA and a target mRNA (see Barh et al., 2010, Curr. Oncol., 17:70-80).

Methods relating to the use of RNAi to silence expression of a target coding sequence are known to the person skilled in the art. Methods of the present invention include decreasing the amount of ER-α66 polypeptide in a cell, decreasing the amount of ER-α36 polypeptide in a cell, increasing sensitivity of a cell to a selective estrogen receptor modulator (SERM), decreasing tumorigenesis, decreasing angiogenesis, decreasing metastatic progression, or a combination thereof. Typically, the presence of one of these characteristics of a cell, such as ER-α36 polypeptide, can be compared with the same type of cell that does not contain a polynucleotide of the invention. Such a cell that does not contain the polynucloetide is referred to as a control cell. A decrease in, for instance, the target mRNA or the amount of polypeptide encoded by the target mRNA in the cell containing a polynucleotide of the present invention indicates the expression of the polypeptide has been inhibited.

In some embodiments, methods of the present invention include treating certain diseases in a subject in need of treatment. The subject is a mammal, including a member of the family Muridae (a murine animal such as rat or mouse), a primate, (e.g., monkey, human), a rabbit, a sheep, a goat, a dog, a pig, or a horse, preferably a human. As used herein, the term "disease" refers to any deviation from or interruption of the normal structure or function of a part, organ, or system, or combination thereof, of a subject that is manifested by a characteristic symptom or clinical sign. Diseases include receptor positive cancers, such as breast cancer, ovarian cancer, pancreatic cancer, endometrial cancer, lung cancer, and colon cancer. Such cancers are typically primary cancers, and can include cancerous cells that are not metastatic, and cancerous cells that are metastatic. Other diseases can include cancers resulting from metastasis of a cancer, such as metastasis of a primary cancer. The metastatic cancer can be located in, for instance, the lymph nodes draining tissues containing a primary tumor.

As used herein, the term "symptom" refers to subjective evidence of disease or condition experienced by the patient and caused by disease. As used herein, the term "clinical sign," or simply "sign," refers to objective evidence of a disease present in a subject. Symptoms and/or signs associated with diseases referred to herein and the evaluation of such signs are routine and known in the art. Examples of signs of disease vary depending upon the disease. Signs of breast cancer may include tumorigenesis, metastasis, angiogenesis, expression of ER-α66 by breast cells, expression of ER-α36 by breast cells, the level of let-7 miRNA expressed by breast cells, resistance of a cell to a selective estrogen receptor modulator such as tamoxifen, or a combination thereof. Typically, whether a subject has a disease, and whether a subject is responding to treatment, may be determined by evaluation of signs associated with the disease.

Treatment of a disease can be prophylactic or, alternatively, can be initiated after the development of a disease. Treatment that is prophylactic, for instance, initiated before a subject manifests signs of a disease, is referred to herein as treatment of a subject that is "at risk" of developing a disease. An example of a subject that is at risk of developing a disease is a person having a risk factor. Risk factors include genetic markers. Examples of genetic markers indicating a subject has a predisposition to develop certain cancers such as breast cancer include family history of breast cancer and alterations in the BRAC1 and/or BRAC2 genes. Treatment can be performed before, during, or after the occurrence of the diseases described herein. Treatment initiated after the development of a disease may result in decreasing the severity of the signs of the disease, or completely removing the signs.

The methods of the present invention may also be practiced using an agent that decreases expression of ER-α36 polypeptide, ER-α66 polypeptide, or both. Examples of such agents include, but are not limited to, small molecules, polypeptides, aptamers, antibodies, etc. Examples of agents that decrease expression of ER-α36 polypeptide are disclosed by Li and Kun (U.S. Published Patent Application 20100016352). As used herein, the term "therapeutic agent" refers to the polynucleotides described herein and to agents such as small molecules, polypeptides, aptamers, antibodies, etc. that decrease expression of ER-α36 polypeptide, ER-α66 polypeptide, or both.

The methods of the present invention may also be practiced using physical therapies that may increase the level of let-7 miRNAs in cells. Examples of useful physical therapies may include massage, chiropractic, or accupuncture regimens.

In some embodiments, the methods include contacting a cell with an effective amount of a therapeutic agent, such as one or more polynucleotides described herein. The contacting is under conditions suitable for introduction of a therapeutic agent, such as one or more polynucleotides, into the cell. Conditions that are "suitable" for an event to occur, such as introduction of a polynucleotide into a cell, or "suitable" conditions are conditions that do not prevent such events from occurring. Thus, these conditions permit, enhance, facilitate, and/or are conducive to the event. As used herein, an "effective amount" relates to a sufficient amount of a therapeutic agent, such as one or more polynucleotides, to provide the desired effect. For instance, in one embodiment an "effective amount" is an amount effective to alleviate one or more symptoms and/or signs of the disease. In some embodiments, an effective amount is an amount that is sufficient to effect a reduction in a symptom and/or sign associated with a disease.

A reduction in a symptom and/or a sign is, for instance, at least 10%, at least 20%, at least 30%, at least 40%, at least 50%, at least 60%, at least 70%, at least 80%, at least 90%, or at least 100% in a measured sign as compared to a control, a non-treated subject, or the subject prior to administration of the polynucleotide. Measured or measurable signs include signs such as the level of ER-α66 polypeptide expressed by a cell, the level of ER-α36 polypeptide expressed by a cell, the resistance of a cell to an SERM, tumorigenesis, angiogenesis, metastasis, or a combination thereof. It will be understood, however, that the total daily usage of the compositions and formulations as disclosed herein will be decided by the attending physician within the scope of sound medical judgment. The exact amount required will vary depending on factors such as the type of disease being treated.

When the therapeutic agent is a polynucleotide, the polynucleotide may be introduced into a cell as a dsRNA polynucleotide, or as a vector including a DNA polynucleotide that encodes and will express the RNA polynucleotide. More than one type of polynucleotide can be administered. For instance, two or more polynucleotides that are designed to silence the same mRNA can be combined and used in the methods herein. Whether a polynucleotide is expected to function in methods of the present invention relating to treatment can be evaluated using ex vivo models and animal models. Such models are known in the art and are generally accepted as representative of disease in humans and useful for evaluation of methods of treating humans. A preferred example of such an animal model is the nude mouse. For instance, breast cancer cells can be inoculated into the mammary fatpad of ovariectomized female nude mice, and lesion formation followed and evaluated, for example, by palpation, measurement by vernier calipers, and tumor weight. Transgenic animal models are also available.

The cells may be in vivo or ex vivo. The cell is preferably a mammalian cell, such as, for instance, mouse, rat, or primate (e.g., monkey, human), preferably, human. Preferred examples of cells include breast cells, such as a breast cancer cell, a ovarian cancer cell, a pancreatic cancer cell, an endometrial cancer cell, a lung cancer cell, and a colon cancer cell. Control cells may be cultured according to methods known in the art. Examples of cells that are ER-α36 positive and ER-α66 positive include T47D, HB3396, and ZR-75-1. Examples of cells that are ER-α36 positive and ER-α66 negative include SK-BR-3, MDA-MB-231, MDA-MB-436, and MDA-MB-468. An example of a cell that expresses ER-α66 and expresses ER-α36 at trace levels is MCF7. Control cells may also be obtained from tissue samples through, for example, biopsy. Other cells can also be modified to express one of the polypeptides by introducing into a cell a vector having a polynucleotide encoding the polypeptide.

In some embodiments the methods of the present invention can include administering to a subject having a disease or at risk of developing a disease a composition including an effective amount of a therapeutic agent, such as a polynucleotide described herein. Preferred methods for administering one or more of the polynucleotides described herein include administration during surgery, for instance surgery to resect a diseased part, organ, system, or combination thereof, of a subject. A diseased part, organ, or system can include, for instance, tumor cells. For instance, after removal of cancer cells the surrounding area can be perfused with a solution containing one or more of the polynucleotides described herein, or an implant containing one or more of the polynucleotides described herein can be placed near the area of resection. The polynucleotides may also be administered by other methods known in the art including, for instance, parenteral administration, such as intravenous administration.

In some embodiments the methods of the present invention may include identifying whether cells have certain characteristics. The cells may be ex vivo or may be in a subject. In one embodiment, a method may include determining the estrogen receptor status of cancer cells of a subject. The "estrogen receptor status" of a cell refers to the level of ER-α36, ER-α66, or both ER-α36 and ER-α66. A cell may display any combination of estrogen receptors. Thus, a cell may be ER-α36 positive (ER-α36(+)) and ER-α66 positive (ER-α66(+)), ER-α36(+) and ER-α66 negative (ER-α66(−)), ER-α36 negative (ER-α36(−)) and ER-α66(+), or ER-α36(−) and ER-α66(−). Methods for determining whether a cell is ER-α36(+) or ER-α36(−) and ER-α66(+) or ER-α66(−) are known in the art and routine. For instance, real time PCR can be used to determine the amount of mRNA encoding either ER-α36 or ER-α66 (see Example 1 and 2). Another method includes the use of antibody that specifically binds ER-α66 polypeptide or ER-α36 polypeptide. Antibody that specifically binds ER-α66 is commercially available. Antibody that specifically binds ER-α36 can be easily produced using a synthetic polypeptide corresponding to the unique carboxy-terminal 20 amino acids of the ER-α36 polypeptide (see Wang, U.S. Patent Application Publication 20070258895). As used herein, an antibody that can specifically bind a polypeptide is an antibody that interacts only with the epitope of the antigen that induced the synthesis of the antibody, or interacts with a structurally related epitope. An antibody that specifically binds to an epitope will, under the appropriate conditions, interact with the epitope even in the presence of a diversity of potential binding targets. A cell is considered to be ER-α66(−) when the level of ER-α66 mRNA or ER-α66 polypeptide, measured using currently available techniques for the detection of mRNA or polypeptides, respectively, is equal to or less than the level of ER-α66 mRNA or ER-α66 polypeptide present in MDA-MB-231 cells. MDA-MB-231 cells are available from ATCC (ATCC number HTB-26). A cell is considered to be ER-α36(−) when the level of ER-α36 mRNA or ER-α36 polypeptide, measured using currently available techniques for the detection of mRNA or polypeptides, respectively, is equal to or less than the level of ER-α36 mRNA or ER-α36 polypeptide present in MCF7 cells. MCF7 cells are available from ATCC (ATCC number HTB-22).

Thus, in one embodiment, a method of the present invention includes identifying a subject that has a cancer cell that is either ER-α36(+) or ER-α36(−). In one embodiment, a method of the present invention includes identifying a subject that has a cancer cell that is either ER-α66(+) or ER-α66(−). In some embodiments, a method of the present invention includes identifying a subject that has a cancer cell that is either ER-α36(+) and ER-α66(+), ER-α36(+) and ER-α66(−), ER-α36(−) and ER-α66(+), or ER-α36(−) and ER-α66(−), and administering to the subject a therapeutic agent, such as a polynucleotide described herein. Optionally, a method of the present invention includes identifying a subject that has a cancer cell that is either progesterone receptor positive or progesterone receptor negative. Optionally, a method of the present invention includes identifying a subject that has a cancer cell that is either Human Epidermal growth factor Receptor 2 (HER2) positive or HER2 negative. The cancer cells in a subject may have any combination of expression of ER-α66, ER-α36, progesterone receptor, and HER2. In one embodiment the subject has cells that are ER-α66(−) and ER-α36(+). In one embodiment the subject has cells that are ER-α66(−) and ER-α36(−). In another embodiment the subject has cells that are ER-α66(+) and ER-α36(−). In another embodiment the subject has cells that are ER-α66(+) and ER-α36(+). In one embodiment the cells are triple negative. As used herein, a cell is considered "triple negative" when it is ER-α66(−), progesterone receptor negative, and Human Epidermal growth factor Receptor 2 (HER2) negative (Zhang et al., 2010, Oncogene, October 11, doi:10.1038/onc.2010.458). Such cells are often associated with aggressive forms of breast cancer, and are often resistant to an SERM. Most triple negative breast cancer cells express ER-α36. Thus, a triple negative cell may be ER-α36(+) or ER-α36(−). In one embodiment the subject has cells that are ER-α66(−) and ER-α36(+), progesterone receptor negative, and HER2 positive.

In another embodiment, a method may include determining whether a cell, such as a breast cancer cell, is resistant to antiestrogen agents. An example of an antiestrogen agent is a selective estrogen receptor modulator (SERM). Examples of SERMs include tamoxifen, raloxifene, ormeloxifene, clomifene, femarelle, toremifene, afimoxifene, arzoxifene, lasofoxifene, and bazedoxifene. Another example of an antiestrogen agent is ICI-182,780. Methods for determining whether a cancer cell in a subject (in vivo) is tamoxifen resistant are known to the skilled person and are routine. For example, tamoxifen sensitive tumors regress (decrease in size) during treatment with tamoxifen. A subject with a tumor that does not decrease in size after 10-14 weeks of treatment with tamoxifen is considered to have a tamoxifen resistant tumor, and that the tumor contains tamoxifen resistant cancer cells. A subject may exhibit acquired resistance, e.g., a tumor may initially regress after tamoxifen treatment, but then become resistant and begin to increase in size. Likewise, ex vivo methods for determining if a cancer cell is tamoxifen resistant are known to the skilled person and are routine. Such methods include culturing the cell and contacting the cell with clinically relevant concentrations of tamoxifen. In one embodiment, if growth, replication, migration, proliferation, differentiation, or a combination thereof, of the cell does not decrease relative to a control cell not contacted with tamoxifen, the cell is considered to be tamoxifen resistant. In one embodiment, an ex vivo cancer cell, such as a breast cancer cell, is considered to be tamoxifen sensitive if the $IC_{50}$ is less than or equal to 5 micromolar, less than or equal to 10 micromolar, less than or equal to 20 micromolar, or less than or equal to 30 micromolar, or less than or equal to 40 micromolar, or less than or equal to 50 micromolar, or less than or equal to 60 micromolar, or less than or equal to 70 micromolar. In one embodiment, an ex vivo cancer cell, such as a breast cancer cell, is considered to be tamoxifen resistant if the $IC_{50}$ is greater than 5 micromolar, is greater than 10 micromolar, is greater than 20 micromolar, or is greater than 30 micromolar, or is greater than 40 micromolar, or is greater than 50 micromolar, or is greater than 60 micromolar, or is greater than 70 micromolar. Methods for determining an $IC_{50}$ are known to the skilled person and are routine.

Thus, in some embodiments, a method of the present invention includes identifying a subject that has a cancer cell that is resistant to a SERM, such as tamoxifen, and administering to the subject an effective amount of therapeutic agent, such as a polynucleotide described herein. In one embodiment the subject has tamoxifen resistant cells that are ER-α36(+) and ER-α66(−). In one embodiment the subject has tamoxifen resistant cells that are ER-α66(−) and ER-α36(+). In one embodiment the subject has tamoxifen resistant cells that are ER-α66(−) and ER-α36(−). In another embodiment the subject has tamoxifen resistant cells that are ER-α66(+) and ER-α36(−). In another embodiment the subject has tamoxifen resistant cells that are ER-α66(+) and ER-α36(+).

In one embodiment the subject has cells that are ER-α66(−), progesterone receptor negative, HER2 negative, and ER-α36 (+). In one embodiment the subject has cells that are ER-α66 (−), progesterone receptor negative, HER2 negative, and ER-α36(−). In one embodiment the subject has cells that are ER-α66(−), ER-α36(+), progesterone receptor negative, and HER2 positive. In one embodiment the cell is a breast cancer cell. The administration of an effective amount of a polynucleotide of the present invention is effective to decrease the tamoxifen resistance (increase tamoxifen sensitivity) of a cancer cell in the subject.

Identifying whether cells of a subject have certain characteristics may include non-invasive techniques. For instance, determining whether an in vivo cell is resistant to a SERM can be accomplished through the use of imaging technologies that measure tumor size. Other methods for identifying whether cells of a subject have certain characteristics may include obtaining a biological sample. As used herein, a "biological sample" refers to a sample of tissue or fluid isolated from a subject, including but not limited to, for example, blood, plasma, serum, urine, bone marrow, bile, spinal fluid, lymph tissue and lymph fluid, samples of the skin, external secretions of the skin, respiratory, intestinal, and genitourinary tracts, tears, saliva, milk, blood cells, and organs. Biological samples can also include sections of tissues such as biopsy and autopsy samples, and frozen sections taken for histologic purposes. Biological samples also include explants and primary and/or transformed cell cultures derived from patient tissues. A biological sample can be provided by removing a sample of cells from a subject, but can also be accomplished by using previously isolated cells (e.g., isolated by another person, at another time, and/or for another purpose). Archival tissues, such as those having treatment or outcome history can also be used.

The polynucleotides described herein can also be administered to a subject in combination with other therapeutic compounds to increase the overall therapeutic effect. Therapeutic compounds useful for the treatment of the diseases described herein are known and used routinely. A wide variety of antitumor agents are available that may be used as a second, supplemental agent, to complement the activity of the polynucleotides described herein. In some embodiments, other therapeutic compounds are anti-cancer agents. In some embodiments, the therapeutic compounds are chemotherapeutic agents, for example cisplatin, paxicital, etc. In some embodiments, the therapeutic compounds are radiotherapeutic agents. Examples of useful chemotherapeutic agents include, for example, nitrogen mustards such as cyclophosphamide, ifosfamide, and melphalan; ethylenimines and methylmelamines such as hexamethylmelamine and thiotepa; pyrimidine analogs such as fluorouracil and fluorodeoxyuridine; vinca alkaloids such as vinblastine; epipodophyllotoxins such as etoposide and teniposide; antibiotics such as actinomycin D, doxorubicin, bleomycin, and mithramycin; biological response modifiers such as interferon; platinum coordination complexes such as cisplatin and carboplatin; estrogens such as diethylstilbestrol and ethinyl estradiol; antiandrogens such as flutamine; and gonadotropin releasing hormone analogs such as leuprolide. Other compounds such as decarbazine, nitrosoureas, methotrexate, diticene, and procarbazine are also effective. In some embodiments, a SERM may be administered with the polynucleotide. Other chemotherapeutic agents which are known to those of ordinary skill in the art can readily be substituted, and this list should not be considered exhaustive or limiting.

The present invention also includes methods for determining whether SERM sensitivity of cancer cells in a subject may be increased using the methods described herein. In one embodiment, the method includes obtaining a biological sample from a subject, wherein the biological sample includes an SERM resistant cancer cell, and determining the estrogen receptor status of the SERM resistant cancer cell. In one embodiment the SERM is tamoxifen. In one embodiment, determining the estrogen receptor status of the SERM resistant cancer cell includes determining expression of ER-α36. The presence of an SERM resistant cell that is ER-α36 positive indicates the SERM sensitivity of cancer cells in the subject may be increased using methods as described herein. In one embodiment, determining the estrogen receptor status of the SERM resistant cancer cell includes determining expression of ER-α66. The presence of an SERM resistant cell that is ER-α66 positive indicates the SERM sensitivity of cancer cells in the subject may be increased using methods as described herein. Such a method may be used to evaluate treatment options for a subject having a cancer. For instance, such a method may indicate that treatment with a therapeutic agent, such as a polynucleotide described herein, is appropriate.

Determining the estrogen receptor status of the SERM resistant cancer cell may also include determining expression of ER-α66, HER2, and/or progesterone receptor. Methods for detecting expression of ER-α66, HER2, and/or progesterone receptor are known to the skilled person and are routine. Any combination of expression of ER-α36, ER-α66, HER2, and progesterone receptor can be detected. Thus, in some embodiments, the method may include determining whether the SERM resistant cell is either ER-α36(+) and ER-α66(+), ER-α36(+) and ER-α66(−), or ER-α36(−) and ER-α66(+). In one embodiment the SERM resistant cell is ER-α36(+), ER-α66(−), progesterone receptor negative, and HER2 negative. In one embodiment the SERM resistant cell is ER-α36(+), ER-α66(−), progesterone receptor negative, and HER2 positive.

The present invention also includes methods for diagnosing whether a subject has, or is at risk for developing, a cancer. The methods may include measuring the level of a let-7 miRNA in a biological sample from a subject. An increase in the level of let-7 miRNA in the biological sample relative to the level of the let-7 miRNA in a control sample, indicates the subject has, or is at risk for developing, cancer. The cancer may be an receptor positive cancer, such as breast cancer, ovarian cancer, pancreatic cancer, endometrial cancer, lung cancer, or a colon cancer. In one embodiment the cancer is a breast cancer. In another embodiment the breast cancer is an early stage breast cancer, such as ductal carcinoma in situ (DCIS). The subject may display one of more signs of a cancer, and may display one or more symptoms of a cancer. In one embodiment the method may also include administering to the subject a polynucleotide described herein in an amount effective to increase the level of the polynucleotide in a cancer cell of the subject.

The let-7 miRNA that is measured may be a primary transcript ("pri-miRNA"), an intermediate miRNA ("pre-miRNA"), or a processed (e.g., mature) RNA transcript from a let-7 miR gene. The pri-miRNA may include miRNA flanking sequences as described herein.

The level of a let-7 miRNA in a sample can be measured using techniques suitable for detecting RNA expression levels in a biological sample. Examples of suitable techniques include Northern blot analysis and RT-PCR, and are well known to the skilled person. In one embodiment, the level of a let-7 miRNA is detected using Northern blot analysis. For example, nucleic acids present in a biological sample, such as blood, plasma, serum, or urine, are precipitated, and DNA is removed by treatment with DNase and precipitation. The RNA molecules may then be separated by gel electrophoresis on agarose gels according to standard techniques, and transferred to nitrocellulose filters. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7.

Suitable probes for Northern blot hybridization of a let-7 miRNA can be produced from the nucleic acid sequences and include, but are not limited to, probes that are complementary or substantially complementary to a let-7 miRNA. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11. A nucleic acid probe can be labeled with, e.g., a radionuclide, such as $^3H$, $^{32}P$, $^{33}P$, $^{14}C$, or $^{35}S$; a heavy metal; a ligand capable of functioning as a specific binding pair member for a labeled ligand (e.g., biotin, avidin or an antibody); a fluorescent molecule; a chemiluminescent molecule; an enzyme or the like.

The relative number of let-7 miRNAs in a biological sample may be determined by reverse transcription of let-7 miRNAs, followed by amplification of the reverse-transcribed miRNAs by polymerase chain reaction (RT-PCR). The levels of let-7 miRNAs can be quantified in comparison with an internal standard, for example, the level of mRNA from a "housekeeping" gene present in the same sample. A suitable "housekeeping" gene for use as an internal standard includes, e.g., RU48. Methods for performing quantitative and semi-quantitative RT-PCR, and variations thereof, are well known to those of skill in the art.

A corresponding control biological sample may be obtained from a normal human individual or population of normal individuals. The control biological sample may then be processed along with the sample from the subject, so that the levels of let-7 miRNA in the subject's biological sample can be compared to the levels of let-7 miRNA in the control biological sample. A reference miRNA expression standard for the biological sample can also be used as a control.

The present invention also includes methods for identifying an agent that increases the amount of a let-7 miRNA in a cell. The method includes contacting a cell, such as a cancer cell, with an agent. The cell may be, for instance, a breast cancer cell, an ovarian cancer cell, a pancreatic cancer cell, an endometrial cancer cell, a lung cancer, or a colon cancer cell. The cancer cell may be ER-α36 positive or ER-α36 negative and ER-α66 positive or ER-α66 negative in any combination. In one embodiment, the cancer cell is a breast cancer cell that is ER-α36 positive. The cancer cell may be progesterone receptor positive or progesterone receptor negative, and may be HER2 positive or HER2 negative. In one embodiment, the cancer cell is a triple negative breast cancer cell (i.e., ER-α36 positive, ER-α66 negative, progesterone receptor negative, and HER2 negative).

The method further includes incubating the cell and the agent under conditions suitable for culturing the cell, and measuring the amount of let-7 miRNA present in the cell. The let-7 miRNA may be in the cytoplasm of the cell and/or in the nucleus of the cell. The cell contacted with the agent having more let-7 miRNA present when compared to let-7 miRNA present in a corresponding control cell that does not include the agent indicates the agent increases the amount of let-7 miRNA in a cell. The agent can be a chemical compound, including, for instance, an organic compound, an inorganic compound, a metal, a polypeptide, a non-ribosomal polypeptide, a polyketide, or a peptidomimetic compound. The sources for potential agents to be screened include, for instance, chemical compound libraries, cell extracts of plants and other vegetations.

The present invention also provides kits for practicing the methods described herein. A kit includes one or more of the polynucleotides described herein in a suitable packaging material in an amount sufficient for at least one use. Optionally, other reagents such as buffers and solutions needed to practice the invention are also included. Instructions for use of the packaged polynucleotide(s) or antibodies are also typically included.

As used herein, the phrase "packaging material" refers to one or more physical structures used to house the contents of the kit. The packaging material is constructed by well known methods, preferably to provide a sterile, contaminant-free environment. The packaging material has a label which indicates that the polynucleotide(s) or antibodies can be used for the methods described herein. In addition, the packaging material contains instructions indicating how the materials within the kit are employed to practice the methods. As used herein, the term "package" refers to a solid matrix or material such as glass, plastic, paper, foil, and the like, capable of holding within fixed limits the polynucleotide(s) or antibodies. Thus, for example, a package can be a glass vial used to contain appropriate quantities of the polynucleotide(s) or antibodies. "Instructions for use" typically include a tangible expression describing the conditions for use of the polynucleotide(s) or antibodies.

The present invention is illustrated by the following examples. It is to be understood that the particular examples, materials, amounts, and procedures are to be interpreted broadly in accordance with the scope and spirit of the invention as set forth herein.

Example 1

Let-7 Family miRNAs Regulate Estrogen Receptor Alpha Signaling in Breast Cancer

To understand how microRNAs (miRNAs) regulate breast cancer tumorigenesis, a RNA expression microarray screening was performed using RNA from formalin-fixed paraffin-embedded (FFPE) breast tissues, which included benign (n=13), ductal carcinoma in situ (DCIS) (n=16), and invasive ductal carcinoma (IDC) (n=15). Twenty-five differentially expressed miRNAs (p<0.01) were identified, of which let-7 family miRNAs were down-regulated in human breast cancer tissues at stages of DCIS and IDC compared to benign stage. It was further found that there was an inverse correlation between ER-α expression and several members of let-7 family in the FFPE tissues. Next, bioinformatics analysis was performed and it was found that let-7 miRNA sequences match sequence in the 3' UTR of estrogen receptor alpha (ER-α), suggesting ER-α may be a target of let-7, which was further confirmed by a number of experimental assays, including luciferase assay, protein expression, and mRNA expression. Overexpression of let-7 miRNAs in ER-positive breast cancer MCF7 cell line negatively affected ER-α activity. Dampening of the ER-α signaling by let-7 miRNAs inhibited cell proliferation, and subsequently triggered the cell apoptotic process in MCF7 cells. In conclusion, these findings not only indicate a new regulatory mechanism of let-7 miRNAs in ER-α mediated cellular malignant growth of breast cancer, but also provide potential biomarkers and/or surrogate therapeutic targets useful for early diagnosis and/or therapeutic options for breast cancer.

Materials and Methods

Cell culture. All breast cell lines were obtained from American Type Culture Collection. The normal breast cell line 184A1 was cultured in 10% Fetal Bovine Serum (FBS) and MEGM (MEBM plus SingleQuots, Clonetics). Breast cancer cell lines, MCF7, ZR-75-1, T47D and HB3396 were kept in phenol-red free IMEM (Cellgro) plus 10% FBS, 1% nonessential amino acid, 10 mmol/L HEPES and 2 µg/mL insulin. For estrogen starvation, the medium was changed into IMEM medium with 2.5% charcoal-stripped FBS instead of 10% FBS. BT474, MDA-MB-231, MDA-MB-436, MDA-MB-468, and SK-BR-3 were cultured in DMEM (Cellgro) plus 10% FBS. Cells were incubated at 37° C. with 5% $CO_2$.

MiRNA microarray. We collected 13 benign, 16 ductal carcinomas in situ (DCIS), and 15 invasive ductal carcinomas (IDC) formalin-fixed paraffin-embedded (FFPE) breast tissues, which were cut into 50 µm thick sheets with a microtome. The benign tissues came from plastic surgery, or some operations for non-malignant tumors (ductal hyperplasia, fibrocystic diseases, adenosis, stromal fibrosis, fibroadenomas, and ruptured cyst). Therefore, these tissues have low levels of ER-α. Because we tried to select pure DCIS and IDC tissues, we did not apply further separation to pinpoint the cancer tissue. We extracted total RNA using the Qiagen miRNeasy FFPE Kit following the manufacturer's instructions, except that the tissues were de-waxed three times and homogenized before proteinase K treatment.

The microarray was a custom service from LC Sciences (Houston, Tex.) using the Sanger's version 11.0. Data adjustment included data filtering, log 2 transformation, and gene centering and normalization. Cluster analysis and visualization were done in Cluster and TreeView (Eisen et al., 1998, Proc Natl Acad Sci USA 95:14863-8).

Quantitative real-time PCR. For miRNA quantification in FFPE tissues, total RNA was extracted as described above; for miRNA quantification in cell lines, total RNA was isolated using mirVana miRNA Isolation Kit (Ambion Inc.). cDNA was synthesized by using 100 ng total RNA in a reaction volume of 15 µL, by following the protocol of Taqman miRNA Reverse Transcription Kit (Applied Biosystems). After 15 times dilution, 9 µL cDNA was used for real-time PCR in a 20 µL reaction volume, including 10 µL of master mix and 1 µL Taqman probe (Applied Biosystems). This reaction system only detects mature miRNAs not pre-miRNAs. The level of each miRNA was expressed following the $2^{-\Delta\Delta Ct}$ or $2^{-\Delta Ct}$ method using the small nuclear RNA, RNU48, as the internal reference.

For real-time PCR on the expression of ER-α, total RNA was extracted using Trizol reagent (Invitrogen). One microgram RNA was used for cDNA synthesis following the protocol of SuperScript III First-Strand Synthesis System (Invitrogen). After 10 times dilution, 4 µL cDNA was used in a 20 µL reaction volume, which included 4 µL of 1.5 µM primers, 2 µL of 2 µM probes, and 10 µL master mix (Applied Biosystems). β-actin was the internal control. The oligos for ER-α are: forward primer, 5'-GCGGCCACGGACCAT (SEQ ID NO:17); reverse primer, 5'-TTCCCTTGGATCTGATG-CAGTA (SEQ ID NO:18); probe, 5'-FAM-CCATGAC-CCTCCACACCAAAGCATC-TAMRA (SEQ ID NO:19).

For FFPE tissues, there was the same repeat number as in microarray; for cell lines, there were three biological repeats. Each sample had three technical repeats on the PCR plate. Real-time PCR was performed on an Applied Biosystems 7900HT real-time PCR instrument. PCR was initiated by two holds of 52° C. 2 min and 94° C. 10 min each, followed by 40 cycles of 15 s at 95° C. and 1 min at 60° C.

Luciferase assay. A fragment of the 3' UTR of human ER-α gene, which contains the putative let-7 target sites, was synthesized (IDT technology). With attached SpeI and HindIII restriction sites, the fragments are 48 by long. The sense strand was 5'-CTAGTTTAAAATTGTTTTCTAAGTAAT-TGCTGCCTCTATTATGGCACA (SEQ ID NO:39) while the antisense strand was 5'-AGCTTGTGCCATAATAGAG-GCAGCAATTACTTAGAAAACAATTTTAAA (SEQ ID NO:40). The corresponding mutant sequences were generated as shown in FIG. 5. The cloning and transfection followed previous protocol (Hu et al., 2009, J Immunol 183: 1617-24). Sixty nanomolar let-7 mimics, anti-let-7 inhibitors, pre-miR negative control #1 (AM17110, Ambion), or anti-miR negative control #1 (AM17010, Ambion) were transfected together with a 0.25 µg luciferase construct and a 0.25 µg β-galactosidase plasmid, which were used as a normalization reference. After 24 hour post-transfection, the luciferase activity was measured in a Veritas Microplate Luminometer (Turner Biosystems). Every treatment had 3 replicates. The luciferase activity was expressed as a fraction of negative control.

For checking on the genomic estrogen pathway, $10^5$ MCF7 cells were first seeded into each well on a 24-well plate and cultured in IMEM with 2.5% charcoal-stripped FBS for 2 days. Then the cells were transfected as described above except that the estrogen response element (ERE) construct (2 ERE-tk-Luc; obtained from Katarine Pettersson, Karolinska Institute, Stockholm) replaced the pMIR-REPORT plasmid for 1 day. After stimulation with 10 nmol/L E2 for 12 hours, luciferase activity was measured as described above.

Immunoblot analysis. For Western blot in FFPE tissues, an established method was followed (Addis et al., 2009, Proteomics 9:3815-23). For MCF7 cell line, let-7 mimics and negative control miRNA (60 nmol/L), or let-7 inhibitors and anti-miR negative control (60 nmol/L) were transfected following the protocol of siPORT NeoFX Transfection Agent (Applied Biosystems), The Western blot procedure was described before (Zhang et al., 2010, J Proteome Res., 9(2): 980-989). Antibody information is as follows: ER-α, RB-9016-P1, Thermoscientific; Cyclin D1, sc-8396, Santa Cruz; pS2, ab80782 was Abeam; β-Actin, sc-69879, Santa Cruz.

MTT cell proliferation assay. MCF7 cells were transfected with let-7 mimics or negative controls (60 nmol/L) in normal growth medium for 1 day, or in medium with 2.5% charcoal-stripped FBS for 2 days to exhaust endogenous estrogen, following the protocol of siPORT NeoFX Transfection Agent (Applied Biosystems). For the experiment in normal growth medium, $10^4$ cells in the volume of 100 µL were seeded in a 96-well plate for 12 hours and assay lasted for another 4 days. For experiments in E2 free medium, 1.5 $10^4$ cells were seeded in a 96-well plate for 12 hours and then exposed to 10 nmol/L E2, or not, for up to 4 days. For both experiments, each treatment had 12 replicates on the plate. The cells were then incubated in 0.83 mg/mL 3-[4,5-dimethylthiazol-2-yl]-2,5-diphenyltetrazolium bromide (MTT) in growth medium at 37° C. for 4 h and lysed in 100 µL of DMSO at room temperature for 15 min. The absorbance in each well was measured at 490 nm by an ELx800 Absorbance Microplate Reader (Biotek). Cell proliferation was normalized to day 0.

Annexin-V binding assay for apoptosis. After transfection with let-7 mimics or negative control as in immunoblot analysis, MCF7 cells were cultured for 6 days. The staining followed the protocol of FITC Annexin V Apoptosis Detection Kit I (Cat #556547, BD Biosciences). Cell populations were analyzed with a BD FACSAria™ flow cytometer. Approximately 20,000 cells were counted for each sample.

Statistical analysis. For miRNA microarray analyses, the ANOVA test was performed among benign, DCIS, and IDC groups. mRNAs with p-values below a critical p-value (<0.01) were selected for cluster analysis. All microarray data were based on four probe replicates for each miRNA prediction. For comparison among means, a one-way ANOVA with the Tukey's adjustment was used for multiple comparisons in SPSS16.0 (SPSS Inc., Chicago, Ill.). Pearson correlation coefficient analysis was used to test the correlation between ER-α protein expression and members of let-7 family, let-7a, let-7b, and let-7i, in FFPE tissues excluding the three ER-α negative cancer tissues (SPSS Inc., Chicago, Ill.).

Results

MiRNA microarray of FFPE tissues. The results show that miRNAs are stable in FFPE tissues. We found that nine miRNAs are upregulated in DCIS and IDC breast cancer samples (p<0.01, Table 1). Among them, miR-21 and miR-155, as reported by other researchers, are associated with breast cancer development (Kong et al., 2008, Mol Cell Biol 28:6773-84, Zhu et al., 2008, Cell Res 18:350-9). The remaining seven miRNAs are oncomirs not reported previously in the development of breast cancer. The miRNAs down-regulated in breast tissues are listed in Table 2 (p<0.01). Down-regulation of let-7a, let-7b, let-7c, miR-125b, miR-145 have been reported in breast cancer (Scott 2007 J Biol Chem 282:1479-86, Yu 2007, Cell 131:1109-23, Wang et al., 2009, Int J Oncol 34:1461-6). The remaining 11 miRNAs were found for the first time to be down-regulated in breast cancer cells. A heat-map of up- and down-regulated miRNAs is shown in FIG. 1A.

TABLE 1 miRNAs up-regulated in DCIS and IDC FFPE samples compared to benign samples based on normalized data. $p < 0.01$.

| Reporter Name | p-value | Benign Mean | Benign SEM | DCIS Mean | DCIS SEM | IDC Mean | IDC SEM |
|---|---|---|---|---|---|---|---|
| hsa-miR-155 | 2.3E−03 | −0.34 | 0.16 | −0.38 | 0.26 | 0.70[b,c] | 0.23 |
| hsa-miR-375 | 8.6E−03 | −0.69 | 0.13 | 0.22[a] | 0.21 | 0.36[b] | 0.31 |
| hsa-miR-1826 | 1.6E−03 | −0.55 | 0.27 | −0.19 | 0.21 | 0.68[b,c] | 0.21 |
| hsa-miR-1280 | 9.9E−04 | −0.81 | 0.31 | 0.25[a] | 0.22 | 0.43[b] | 0.13 |
| hsa-miR-1274b | 5.0E−04 | −0.81 | 0.24 | 0.15[a] | 0.20 | 0.54[b] | 0.22 |
| hsa-miR-720 | 1.5E−04 | −0.84 | 0.25 | 0.12[a] | 0.21 | 0.61[b] | 0.19 |
| hsa-miR-342-3p | 6.8E−03 | −0.66 | 0.16 | 0.08 | 0.25 | 0.49[b] | 0.26 |
| hsa-miR-425 | 2.6E−04 | −0.86 | 0.21 | 0.22[a] | 0.23 | 0.51[b] | 0.20 |
| hsa-miR-21 | 1.2E−03 | −0.64 | 0.24 | −0.10 | 0.25 | 0.66[b,c] | 0.18 |

Note:
[a]significant difference between benign and DCIS;
[b]significant difference between benign and IDC;
[c]significant difference between DCIS and IDC

TABLE 2 miRNAs down-regulated in DCIS and IDC FFPE samples compared to benign samples based on normalized data. $p < 0.01$.

| Reporter Name | p-value | Benign Mean | Benign SEM | DCIS Mean | DCIS SEM | IDC Mean | IDC SEM |
|---|---|---|---|---|---|---|---|
| hsa-miR-212 | 5.8E−03 | 0.72 | 0.21 | −0.28[a] | 0.25 | −0.33[b] | 0.24 |
| hsa-miR-205 | 7.2E−03 | 0.70 | 0.22 | −0.35[a] | 0.25 | −0.23[b] | 0.23 |
| hsa-miR-125b | 9.5E−03 | 0.53 | 0.14 | 0.10 | 0.29 | −0.57[b] | 0.23 |
| hsa-miR-99a | 9.0E−03 | 0.42 | 0.16 | 0.23 | 0.29 | −0.61[b,c] | 0.22 |
| hsa-miR-132 | 2.1E−03 | 0.77 | 0.29 | −0.24[a] | 0.17 | −0.42[b] | 0.23 |
| hsa-let-7b | 5.4E−04 | 0.77 | 0.16 | −0.07[a] | 0.23 | −0.60[b] | 0.25 |
| hsa-let-7a | 2.2E−03 | 0.75 | 0.17 | −0.15[a] | 0.27 | −0.48[b] | 0.21 |
| hsa-let-7c | 7.0E−04 | 0.77 | 0.16 | −0.08[a] | 0.24 | −0.58[b] | 0.24 |
| hsa-miR-423-5p | 6.8E−03 | 0.61 | 0.21 | 0.02 | 0.24 | −0.55[b] | 0.25 |
| hsa-miR-768-5p | 1.3E−03 | 0.77 | 0.24 | −0.15[a] | 0.27 | −0.50[b] | 0.15 |
| hsa-miR-379 | 6.2E−03 | 0.59 | 0.29 | 0.06 | 0.18 | −0.57[b] | 0.25 |
| hsa-miR-497 | 1.9E−03 | 0.68 | 0.31 | 0.01 | 0.21 | −0.60[b] | 0.17 |
| hsa-miR-34a | 7.0E−05 | 0.93 | 0.24 | −0.33[a] | 0.23 | −0.45[b] | 0.16 |
| hsa-miR-145 | 1.2E−05 | 0.94 | 0.17 | −0.15[a] | 0.24 | −0.65[b] | 0.18 |
| hsa-miR-335 | 3.1E−03 | 0.42 | 0.32 | 0.30 | 0.21 | −0.68[b,c] | 0.17 |
| hsa-miR-195 | 1.1E−04 | 0.81 | 0.28 | −0.03[a] | 0.20 | −0.67[b] | 0.16 |

Note:
[a]significant difference between benign and DCIS;
[b]significant difference between benign and IDC;
[c]significant difference between DCIS and IDC Another heat-map was made of all let-7 family members and it was found that they tend to be down-regulated, although some of them did not reach the p<0.01 level (the p value of let-7d and let-7f was <0.05, but that of let-7e, let-7g, and let-7i was >0.05, FIG. 1B, Table 3). Let-7a, let-7b, let-7c, and let-7i were confirmed to be down-regulated with real-time PCR using the same set of FFPE tissues (FIG. 1C). We further confirmed expression levels of these miRNAs in established breast cancer cell lines by means of real-time PCR. The immortal, but non-malignant breast cell line, 184A1, was used as the control. The Ct values of internal reference gene RNU48 were shown in FIG. 2. Because there was no significant difference in Ct values among the cell lines, RNU48 was a good reference gene. FIG. 1D shows that the endogenous levels of let-7 miRNAs such as let-7a, let-7b, let-7c, let-7e, and let-7g, are consistently low in tested human breast cancer cell lines when compared to the non-malignant human breast cell line 184A1 (FIG. 1D, Table 4). For the classical ER-α positive cell line MCF7, let-7 miRNAs except let-7i (no significant difference) were consistently down-regulated. Particularly, let-7a, let-7b, and let-7c are greatly reduced (less than or equal to 10% of control).

TABLE 3

Other down-regulated let-7 miRNAs in DCIS and IDC FFPE samples compared to benign samples based on normalized data although $p > 0.01$.

| Reporter Name | p-value | Benign Mean | Benign SEM | DCIS Mean | DCIS SEM | IDC Mean | IDC SEM |
|---|---|---|---|---|---|---|---|
| hsa-let-7d | 1.5E−02 | 0.63 | 0.18 | −0.13 | 0.29 | −0.41[b] | 0.22 |
| hsa-let-7e | 3.8E−01 | 0.33 | 0.19 | −0.12 | 0.32 | −0.16 | 0.23 |
| hsa-let-7f | 3.0E−02 | 0.60 | 0.17 | −0.17 | 0.30 | −0.33[b] | 0.22 |
| hsa-let-7g | 4.0E−01 | 0.32 | 0.20 | −0.16 | 0.32 | −0.11 | 0.22 |
| hsa-let-7i | 1.8E−01 | 0.29 | 0.14 | −0.36 | 0.35 | 0.13 | 0.19 |

Note:
[a]significant difference between benign and DCIS;
[b]significant difference between benign and IDC.

TABLE 4

Endogenous levels of let-7 microRNAs in human breast cancer cell lines.

| Cell lines | Let-7 microRNAs | | | | | | | |
|---|---|---|---|---|---|---|---|---|
| | a | b | c | d | e | f | g | i |
| 184A1 | — | — | — | — | — | — | — | — |
| BT474 | ↓ | ↓ | ↓ | ↓ | ↓ | ↓ | ↓ | ↓ |
| SK-BR-3 | ↓ | ↓ | ? | ↓ | ↓ | ↓ | ↓ | ↓ |
| MDA-MB-231 | ↓ | ↓ | ↓ | ↓ | ↓ | ↓ | ↓ | ↓ |
| MDA-MB-436 | ? | ↓ | ↓ | ? | ↓ | ? | ↓ | ? |
| MDA-MB-468 | ↓ | ↓ | ↓ | ↓ | ↓ | ↓ | ↓ | ↓ |
| T47D | ↓ | ↓ | ↓ | ↓ | ↓ | ↓ | ↓ | ↓ |
| HB3396 | ↓ | ↓ | ? | ? | ↓ | ? | ↓ | ? |
| ZR-75-1 | ? | ? | ↓ | ? | ? | ? | ↓ | ? |
| MCF-7 | ↓ | ↓ | ↓ | ? | ↓ | ↓ | ↓ | ? |

Note:
↓ indicates significant change in let-7 expression compared to non-malignant breast cell line (184A1).
? indicates no significant down-regulation in let-7 expression compared to non-malignant breast cell line (184A1).

Figure 3:
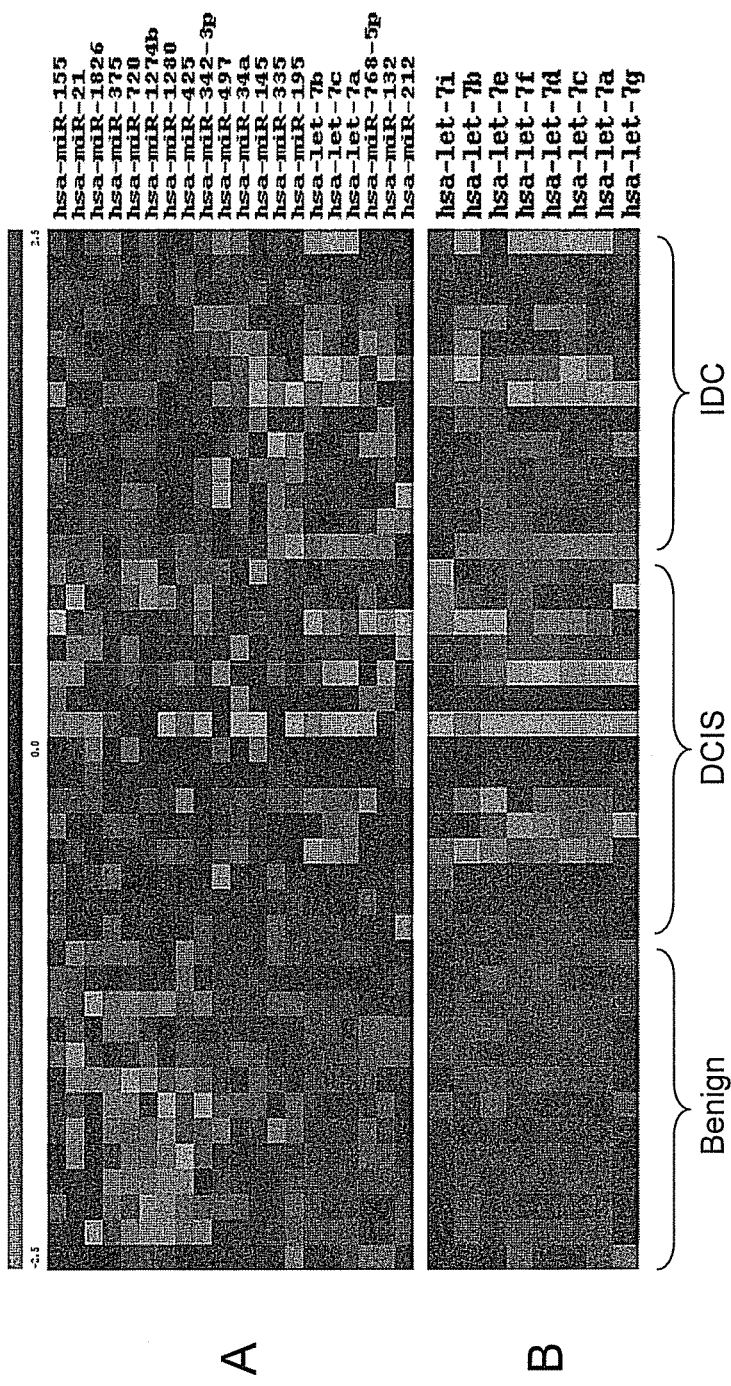
FIG. 3. Heat-map of miRNA microarray of FFPE breast cancer tissues excluding ER-α negative breast cancer tissues. Let-7 a, let-7b, and let-7c are downregulated in DCIS and IDC samples. A), all deregulated miRNAs that reach the $p<0.01$ level; B), let-7 family miRNAs are deregulated in breast cancer tissues, although some of them do not reach the $p<0.01$ level.
Figure 4:
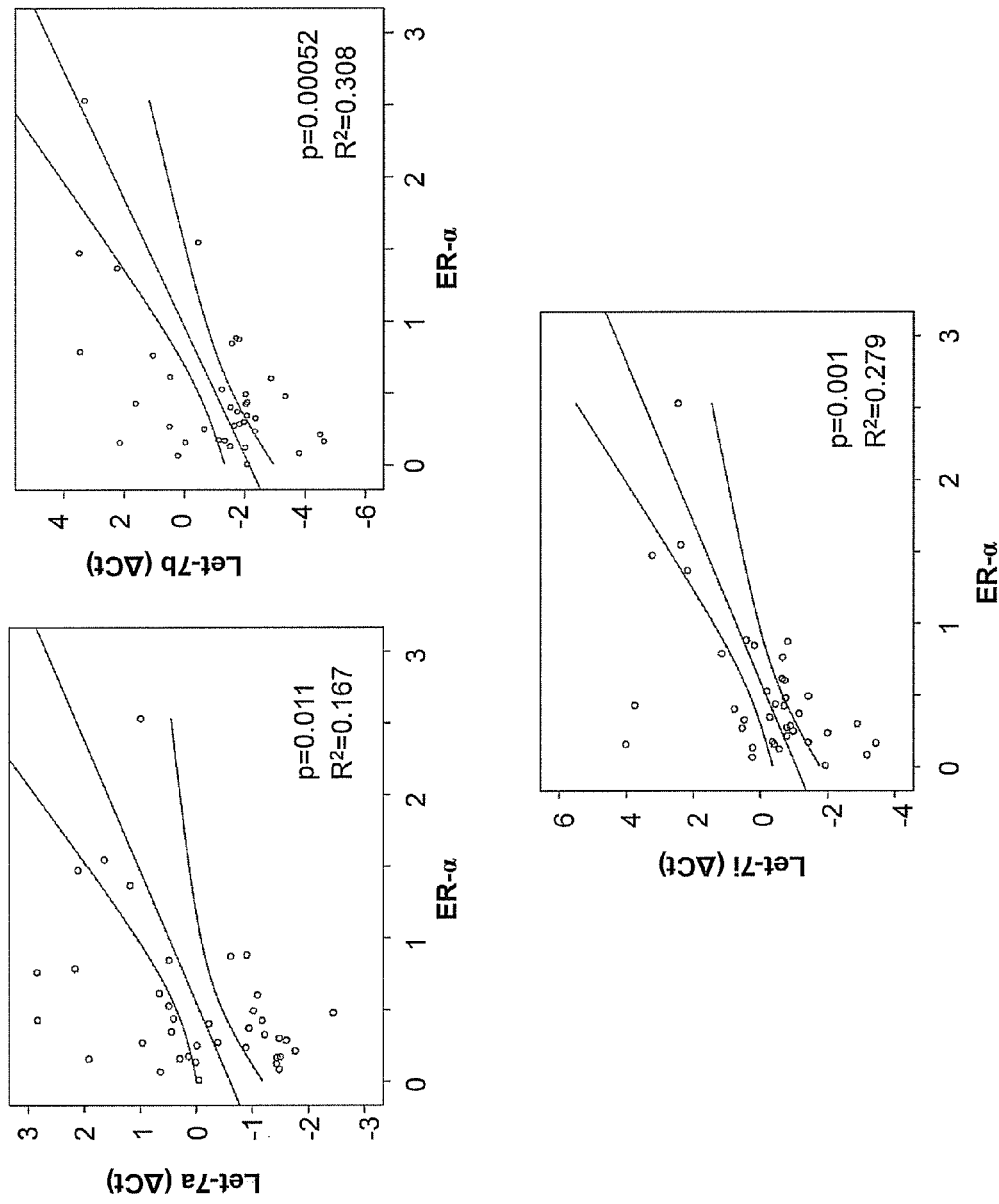
FIG. 4. Inverse correlation between ER-α protein expression and members of let-7 family, let-7a, let-7b, and let-7i, in FFPE tissues excluding the three ER-α negative cancer tissues. Confidence Interval (95% CI) on Pearson's Correlation is shown in each chart.

Let-7 miRNAs target ER-α. ER-α plays a crucial role in development of breast cancer. After reanalyzing the FFPE microarray data excluding ER-α negative breast cancer tissues (one in DCIS group and two in IDC group), We found that let-7a, let-7b, and let-7c were still among the downregulated miRNAs (p<0.01, FIG. 3). As a matter of fact, all let-7 family members tend to be downregulated in ER-α positive breast cancer tissues (FIG. 3B, Table 5). Because the benign tissues express low level ER-α, there is an inverse correlation between the expressions of let-7 miRNAs and ER-α. This inverse correlation between ER-α and let-7a, let-7b, and let-7i is further established based on the ΔCt values of let-7 and Western blot data of FFPE tissue (FIG. 4). The reason to exclude ER-α negative tissues from analysis is because previous reports show that let-7 is lower in ER-α negative than in ER-α positive breast cancer (Mattie et al., 2006, Mol Cancer 5:24, Blenkiron et al., 2007, Genome Biol 8:R214).

TABLE 5

Let-7 miRNAs are downregulated in DCIS and IDC FFPE samples compared to benign samples based on normalized data excluding ER-α negative breast cancer tissues.

| Reporter Name | p-value | Benign | | DCIS | | IDC | |
|---|---|---|---|---|---|---|---|
| | | Mean | SEM | Mean | SEM | Mean | SEM |
| hsa-let-7a | 4.7E−03 | 0.70 | 0.17 | −0.21[a] | 0.28 | −0.46[b] | 0.24 |
| hsa-let-7b | 1.5E−03 | 0.73 | 0.16 | −0.12[a] | 0.24 | −0.59[b] | 0.28 |
| hsa-let-7c | 1.9E−03 | 0.73 | 0.15 | −0.15[a] | 0.25 | −0.56[b] | 0.27 |
| hsa-let-7d | 2.6E−02 | 0.60 | 0.17 | −0.20 | 0.30 | −0.36[b] | 0.25 |
| hsa-let-7e | 3.1E−01 | 0.36 | 0.19 | −0.14 | 0.33 | −0.19 | 0.23 |
| hsa-let-7f | 4.1E−02 | 0.57 | 0.17 | −0.23 | 0.31 | −0.31 | 0.25 |
| hsa-let-7g | 3.7E−01 | 0.32 | 0.20 | −0.19 | 0.33 | −0.11 | 0.24 |
| hsa-let-7i | 1.6E−01 | 0.35 | 0.14 | −0.37 | 0.37 | 0.07 | 0.18 |

Note:
[a] significant difference between benign and DCIS;
[b] significant difference between benign and IDC.

The MiRanda software (a web-accessible information resource produced and maintained at cBio, the Computational Biology Center at Memorial Sloan-Kettering Cancer Center) indicated that let-7 miRNAs complement with 3'-UTR of ER-α (FIG. 5). The ΔG of the RNA duplex is −16.2 kcal/mole between the 3' UTR of ER-α and let-7a Zuker et al., 1999, In: RNA Biochemistry and Biotechnology, Barciszewski and Clark, eds., NATO ASI Series, Kluwer Academic Publishers). The pairing between ER-α and other members of let-7 family is similar (FIG. 5A). We cloned the putative binding and flanking sequence in the 3' UTR of ER-α into 3' UTR of luciferase in the pMIR-REPORT plasmid. We chose let-7a, let-7b, and let-7i for further study because let-7a and let-7b were similarly downregulated in MCF7 cell line (FIG. 1D). Although let-7i is not downregulated in MCF7 cell line compared to benign cell line 184A1, the inclusion of it was to test the hypothesis that let-7 family members have common targets because of the high similarity among their sequences. Co-transfection assays with 60 nmol/L let-7 miRNA mimics in MCF7 cells showed that let-7a, let-7b and let-7i similarly decreased the luciferase activity when compared to controls, which were transfected with negative control miRNA (FIG. 5B). Mutations in the putative binding sequences abrogated the effects of these miRNAs (FIG. 5C). The effect of let-7 inhibitors was also tested in 184A1 cell line because it contains relatively abundant let-7 miRNAs. We found that let-7a, let-7b and let-7i inhibitors greatly increased the luciferase activity (3-5 fold) of the reporter gene carrying the putative binding site (FIG. 5D).

Next, we transfected miRNA mimics of let-7a, let-7b, and let-7i into MCF7 cells to determine the expression levels of ER-α. After 2 days, all three mimics significantly depressed the expression of ER-α. However, let-7b appeared the most effective (FIG. 6A). After 6 days, let-7b and let-7i dramatically down-regulated the expression of ER-α, while let-7a had a modest effect on the protein expression (FIG. 6A). At the mRNA level, real-time PCR results showed that all three let-7 miRNAs inhibited ER-α mRNA expression after 2 days (37%-56% of negative control, p<0.01, FIG. 6B), indicating that let-7 miRNAs accelerated the degradation of ER-α mRNA. However, the inhibition of let-7a was relieved after 6 days (FIG. 6B).

In order to probe the reason for the relatively mild effect of let-7a on ER-α protein expression, the mature forms of the three miRNAs after transfection were quantified by real-time PCR (FIG. 6C). Because MCF7 cell line has different baseline levels of the three miRNAs, the relative quantity against RNU48 ($2^{-\Delta Ct}$) was shown in FIG. 6C. The fold change data can be found in FIG. 7. At one day post transfection, let-7b was ~20 higher than let-7a and ~6 higher than let-7i although the original concentration was the same (60 nmol/L). After 2 days, the expression of let-7b was 2 higher than those of let-7a and let-7i. After 6 days, let-7b was ~10 higher than let-7a. Throughout the time course, let-7b had the highest expression, let-7i was in the middle, and let-7a had the lowest expression (FIG. 6C). The difference in the quantity of three miRNAs offered good explanation for the inconsistency observed.

ER-α is a transcription factor that induces expression of many downstream genes such as cyclin D1, pS2 and c-Myc (Oxelmark et al., 2006, Mol Cell Biol 26:5205-13). We checked the expression levels of cyclin D1 and pS2 after transfection of mimics of let-7a, let7-b, and let-7i in the MCF7 cell line (FIG. 6A). After 2 days, all three mimics significantly inhibited the expression of cyclin D1 and pS2. However, let-7b and let-7i had stronger effect than let-7a, corresponding to their expression level (FIGS. 6A and C). After 6 days, let-7b significantly decreased the protein expression of cyclin D1, yet, let-7i showed a modest effect on cyclin D1. The protein expression of pS2 was significantly suppressed by both let-7b and let-7i (FIG. 6A). However, let-7a affected neither cyclin D1 nor pS2.

On the other hand, let-7 inhibitors had the opposite effect on ER-α expression. We first checked the transfection efficiency by real-time PCR. As reported earlier (Yu 2007, Cell 131:1109-23), inhibitor of one let-7 family member could inhibit the level of other members except that let-7i inhibitor did not inhibit the level of let-7b (FIG. 8A). All three inhibitors boosted the expression of ER-α although the mRNA levels were not affected (FIGS. 8B and C).

To examine the effects of these miRNAs on transcriptional activity of ER-α, we co-tranfected miRNA mimics with p2 ERE-tk-Luc. FIG. 6C shows that all three miRNAs (let-7a, let-7b, and let-7i) significantly down-regulated luciferase activity compared to negative controls. Let-7a and let-7i inhibited the luciferase activity to about 60% of negative control while let-7b inhibited to about 40% (p<0.01).

Let-7 miRNAs inhibit cell proliferation in MCF7. ER-α is important for cell proliferation in ER-positive breast cancer. We studied the effect of let-7 miRNAs on cell proliferation in MCF7. First, we checked the effect in normal growth medium. Let-7a did not show a significant effect over the time course. However, let-7b and let-7i significantly inhibited cell proliferation (FIG. 9A). The significant effect of let-7i was detected from the $3^{rd}$ day, while the effect of let-7b was detected from the $2^{nd}$ day. Particularly, cells growth stopped with the treatment of let-7b (FIG. 9A).

Next, we examined cell proliferation with and without the exogenous estrogen addition. With addition of 10 nmol/L E2, all three mimics showed inhibition on cell growth. Again, let-7a showed the least inhibition and the inhibition even disappeared at the $4^{th}$ day (FIG. 9B). Let-7b and let-7i showed consistent inhibition on estrogen-dependent cell proliferation (FIG. 9C and FIG. 9D). Even without E2 addition, the three let-7 mimics still showed obvious cell growth inhibition (FIG. 9B, C, D). This could be explained by the fact that let-7 not only targets ER-α, but also targets many other proteins, like RAS, HMGA2, cyclin D1, and c-Myc Johnson et al., 2005, Cell 120:635-47, Lee and Dutta 2005, Genes Dev 21:1025-30, Mayr et al., 2007, Science 15:1576-9, Kim et al., 2009, Genes Dev 23:1743-8, Schultz et al., 2008, Cell Res 2008; 18:549-57). Another possible reason is that there was still some estrogen even after two days of culture in medium with charcoal-stripped FBS. However, none of the three miRNAs significantly inhibited cell growth in ER-α negative cell line MDA-MB-231 (FIG. 10), which strongly indicates that the inhibition on cell growth in MCF7 cell line is largely due to inhibition on ER-α function.

Figure 11:
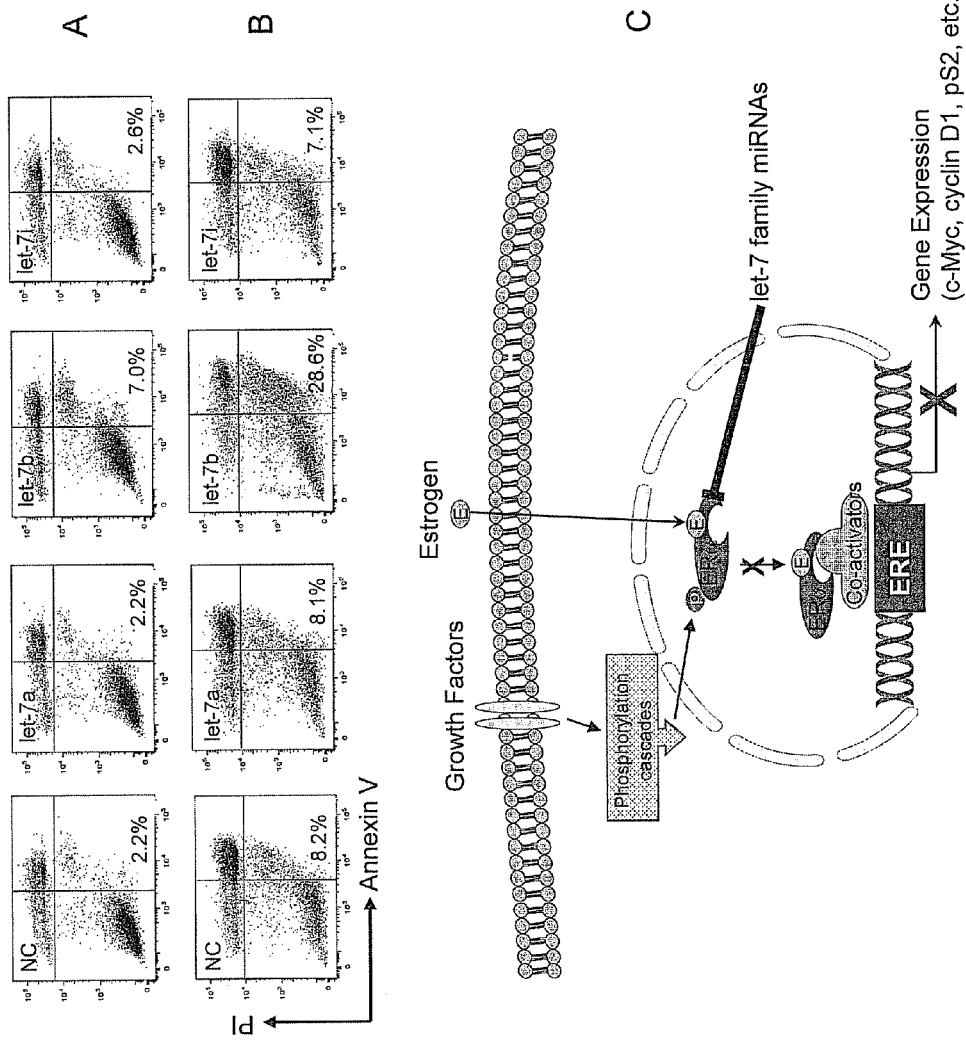
FIG. 11. A), B), the effects of let-7a, let-7b, and let-7i miRNAs on breast cancer cell apoptosis in MCF7 cell line. Apoptosis was measured after application of a negative control, let-7a, let-7b, and let-7i for 3 days (A) and 6 days (B) by dual staining with the viability dye propidium iodide and Annexin V-FITC followed by flow cytometric analysis. The proportion of early apoptotic cells are shown in the bottom right quadrant of each graph. (C), a schematic diagram about the regulatory role of let-7 miRNAs on ER-α signaling in breast cancer based on the results of Example 1.

Let-7 miRNAs caused cell apoptosis in MCF7. To find out whether the inhibitory effect of let-7 miRNAs on the cell proliferation was caused by apoptosis, we checked the effect of let-7a, let-7b, and let-7i on cell apoptosis in MCF7 cells. Three days post-transfection, only let-7b significantly increased the apoptotic rate (7%) compared to controls (2.2%) (FIG. 11A). After 6 days, let-7b further promoted the apoptotic rate to 28.6% while control cells had only 8.2% (FIG. 11B). However, the effects of let-7a and let-7i were not significant after either 3 days or 6 days (FIG. 11]). Obviously, at least, let-7b strongly stimulates apoptosis in MCF7 cell line.

Discussion

Figure 2:
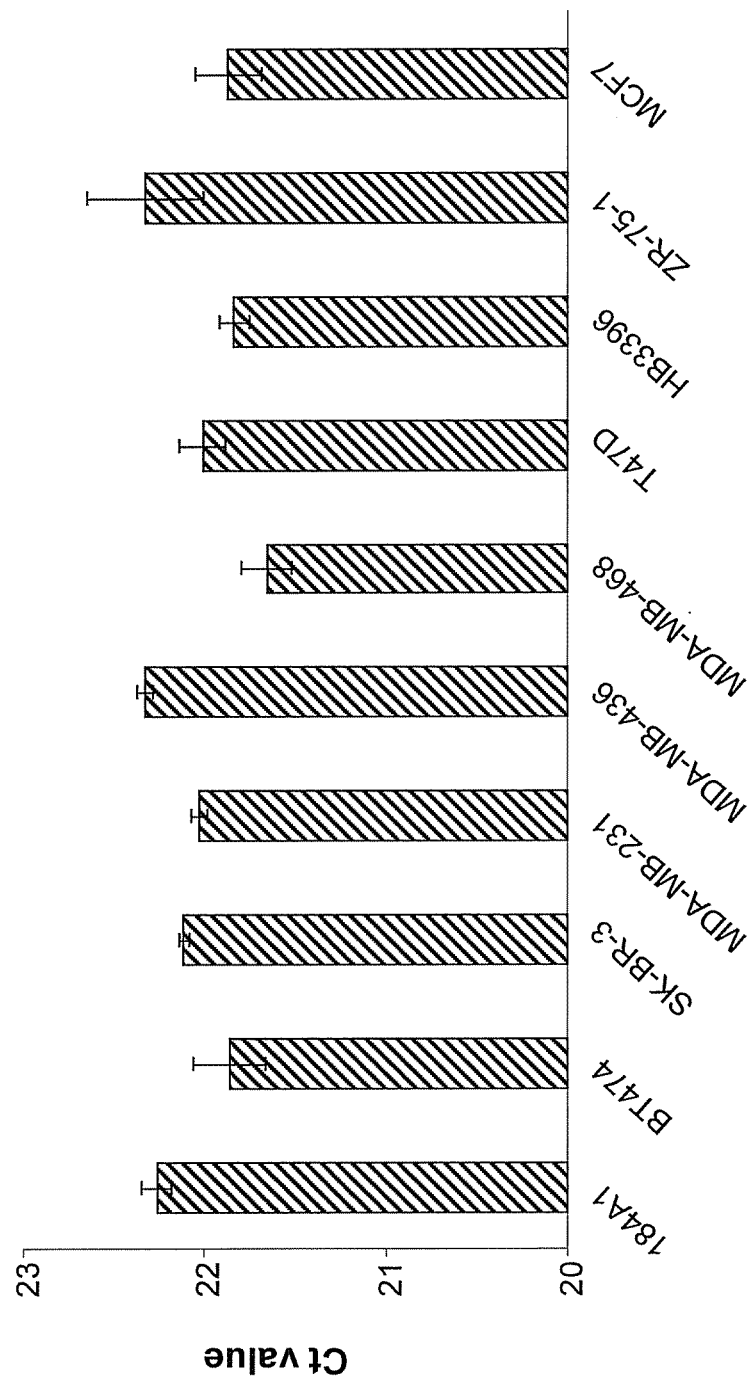
FIG. 2. Ct values of reference gene RNU48 among different breast cancer cell lines. RNA samples were extracted at three different culture times and each sample has three technical replicates.

FFPE samples are widely available and precious for miRNA profiling studies (Table 1, 2, 3; FIG. 1). Global miRNA profiling on FFPE samples is far more reliable and robust than mRNA profiling because mRNA is more easily degraded (Cronin et al., 2004, Am J Pathol 164:35-42). Previous research shows that miRNA expression profiling of FFPE samples are very similar to those of fresh frozen tissues (Liu et al., 2009, Int J Clin Exp Pathol 2:519-27, Xi et al., 2007, RNA 13:1668-74, Zhang et al., 2008, J Mol Diagn 10:513-9, Hui et al., 2009, Lab Invest 89:597-606). This is because miRNAs are resistant to methylol cross-linking between RNA and protein (Li et al., 2007, BMC Biotechnol 7:36). These multiple examples demonstrate the validity of using FFPE samples for miRNA profiling. Our study adds new information to the long list of miRNAs associated with breast cancer. Statistical analysis shows 9 miRNAs are upregulated (Table 1) in breast cancer, including those identified previously such as miR-21 and miR-155. MiR-21 is associated with advanced clinical stage, metastasis and poor prognosis (Yon et al., 2008, RNA 14:2348-60) as well as targeting suppressor genes for invasion and metastasis (Zhu et al., 2008, Cell Res 18:350-9). miR-155 was upregulated in breast cancer tissue (Iorio et al., 2005, Cancer Res 65:7065-70) and plays an important role in TGF-β controlled epithelial-mesenchymal transition by targeting RhoA (Kong et al., 2008, Mol Cell Biol 28:6773-84). We also identified 16 downregulated miRNAs (Table 2), which included some known miRNAs, like let-7, miR-145, and miR-125b. Downregulation of miR-125b has been repeatedly detected in breast cancers (Mattie et al., 2006, Mol Cancer 5:24, Iorio et al., 2005, Cancer Res 65:7065-70). Expression of miR-145 was found to be restricted to the myoepithelial/basal cell compartment of normal mammary ducts and lobules, while its expression was reduced or completely eliminated in matching tumor specimens (Sempere et al, 2007, Cancer Res 67:11612-20). Our study identified some poorly characterized dysregulated miRNAs in breast cancer as shown in Tables 1 and 2, which provide new insight into the complex mechanism of breast cancer.

The connection between breast cancer and estrogen has been recognized for more than 100 years. ER-α is a ligand-regulated transcription factor with a broad range of physiological functions and its overexpression is an important prognostic factor for human breast cancer. The ER-α mRNA has a long 3' UTR of about 4.3 kb, which has evolutionarily conserved miRNA target sites. Previous research has shown that ER-α expression is downregulated by miR-18a, miR-19b, miR20b (Castellano et al., 2009, Proc Natl Acad Sci USA, 106:15732-15737). Another group identified 21 miRNAs that downregulate ER-α expression, among which miR-18a, miR-18b, miR-193b, miR-206, miR-302c were confirmed by luciferase assay (Leivonen et al., 2009, Oncogene, 28 (44):3926-3936). MiR-22 also strongly represses ER-α expression, compromising estrogen signaling as demonstrated by its inhibitory impact on the ER-α-dependent proliferation of breast cancer cells (Pandey and Picard 2009, Mol Cell Biol 29:3783-90). MiR-221 and miR-222 directly target ER-α (Zhao et al., 2008, J Biol Chem 283:31079-86), as does miR-206 (Adams et al., 2007, Mol Endocrinol 21:1132-47, Kondo et al., 2008, Cancer Res 68:5004-8).

Figure 6:
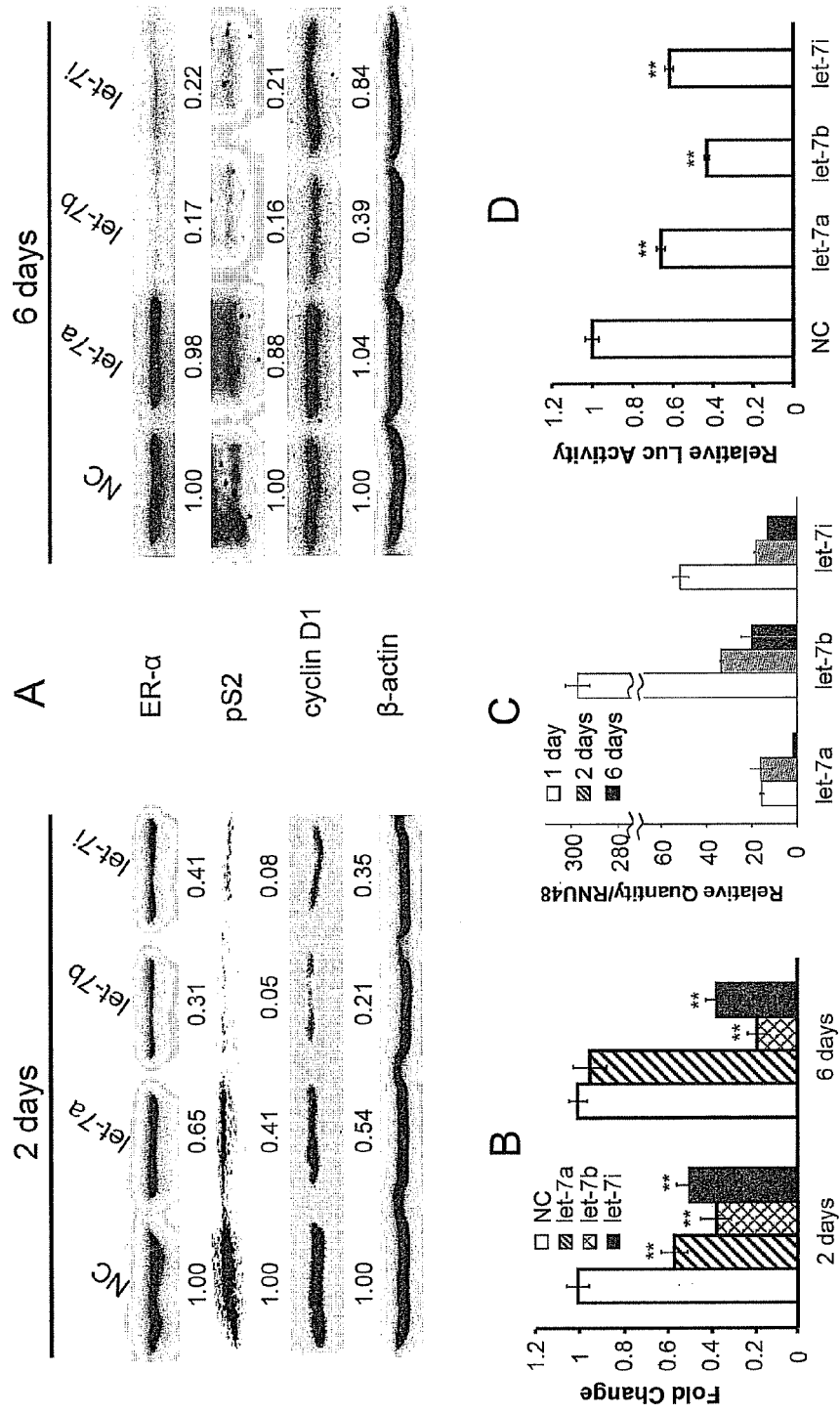
FIG. 6. Let-7 miRNAs affect the estrogen genomic signal transduction pathway. **, $p<0.01$. A), The effect of let-7a, let-7b, and let-7i on the expression of ER-α, pS2, and cyclin D1 in MCF7 cell line after 2 days and 6 days. B), the mRNA level of ER-α after transfection as quantified by realtime PCR. C), quantification of forced overexpression of let-7a, let-7b, and let-7i in MCF7 cell line. The relative quantity was calculated by $2^{-\Delta Ct}$ using RNU48 was the internal reference. D), let-7a, let-7b, and let-7i inhibit the luciferase activity of the ERE construct in the MCF7 cell line.
Figure 7:
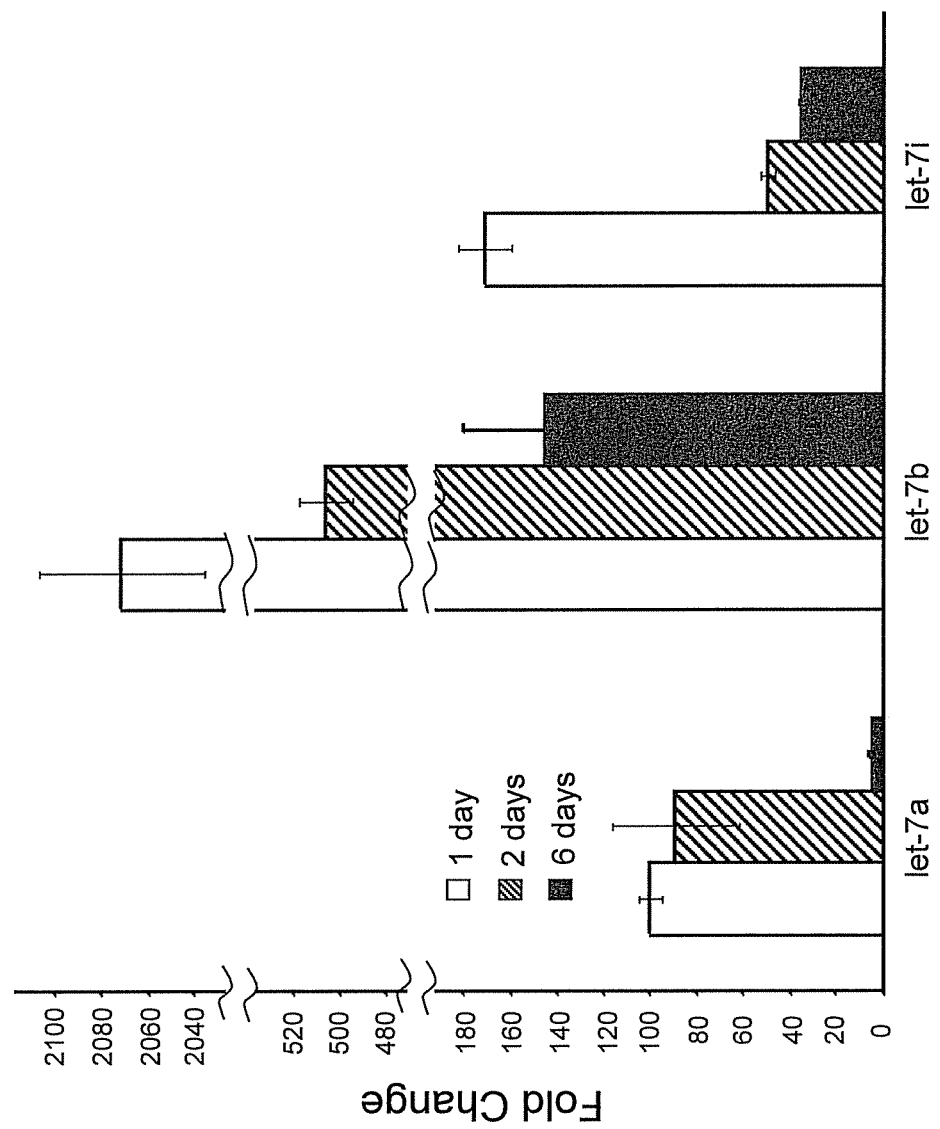
FIG. 7. Quantification of forced overexpression of let-7a, let-7b, and let-7i in MCF7 cell line, expressed as fold change, which was calculated by $2^{-\Delta\Delta Ct}$ using RNU48 was the internal reference.
Figure 8:
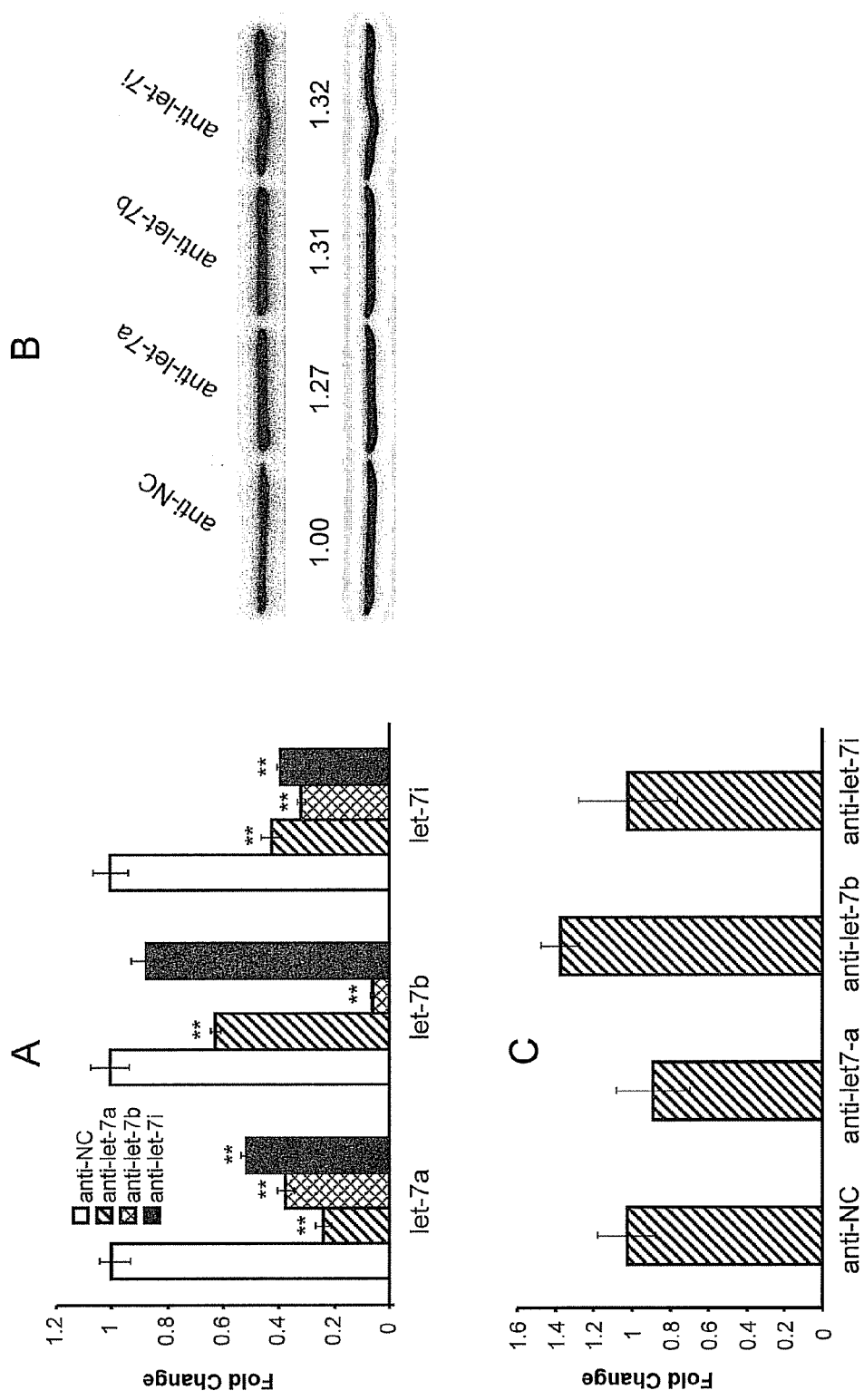
FIG. 8. Let-7 miRNA inhibitors affect the expression of ER-α in MCF7 cell line after 2 days. **, $p<0.01$. A), quantification of let-7a, let-7b, and let-7i after application of their inhibitors (60 nmol/L) in MCF7 cell line. The relative quantity was calculated by $2^{-\Delta\Delta Ct}$ using RNU48 as the internal reference. B), the effect of let-7a, let-7b, and let-7i inhibitors on the expression of ER-α. C), the mRNA level of ER-α after transfection as quantified by realtime PCR.
Figure 9:
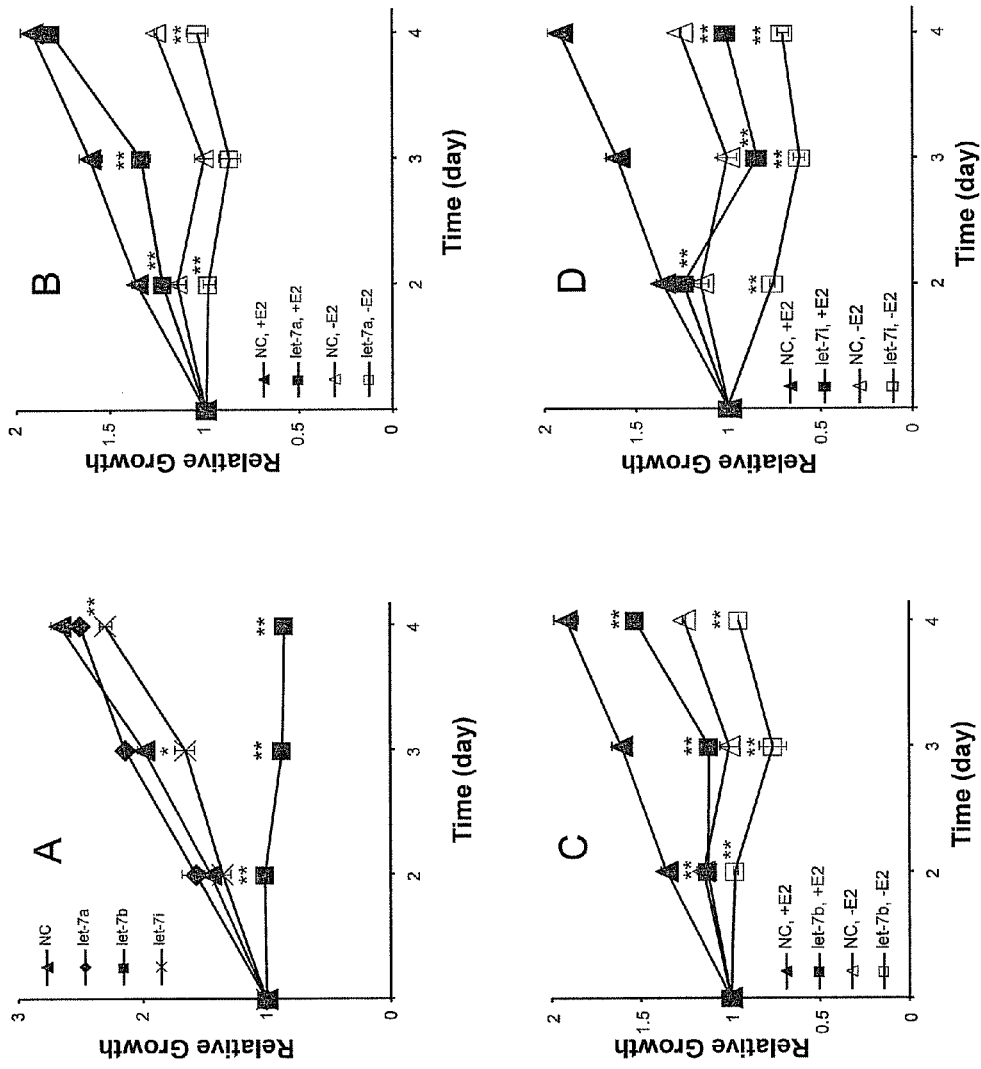
FIG. 9. The effects of let-7a, let-7b, and let-7i miRNAs on cell proliferation in MCF7 cell line. Cancer cell proliferation was monitored by MTT assays. *, $p<0.05$; **, $p<0.01$ compared to NC (negative control). A), cell growth in normal growth medium. B), C), D), cell growth in E2 free medium with or without addition of 10 nmol/L E2. B), cell growth was slightly inhibited by let-7a. C), cell growth was strongly inhibited by let-7b. D), cell growth was strongly inhibited by let-7i.
Figure 10:
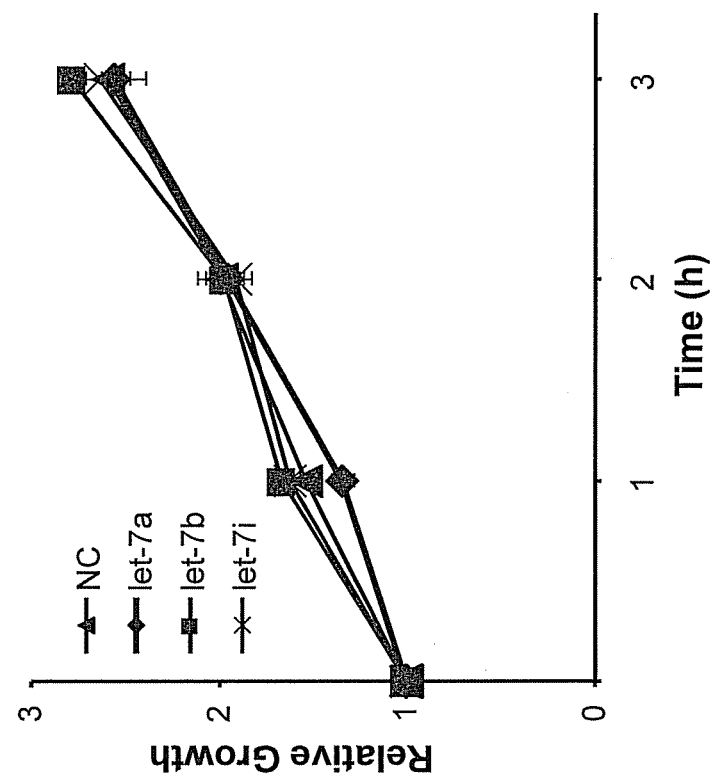
FIG. 10. The effects of let-7a, let-7b, and let-7i miRNAs on cell proliferation in ER-α negative MDA-MB-231 cell line. Cancer cell proliferation was monitored by MTT assays in the same way as in MCF7 cell line except MDA-MB-231 cells were grown in DMEM with 10% FBS. None of three miRNAs significantly inhibited cell growth.

Adding to this long list, we have shown that let-7 miRNAs targets ER-α and represses estrogen signaling. Multiple evidences are offered in this study. We further demonstrated that let-7 overexpression resulted in impaired ER-α-dependent genomic signal pathway based on two pieces of evidence. One is the effect of let-7 miRNAs on downstream targets of ER-α, cyclin D1, and pS2 (FIG. 6A). The other piece of evidence is that all three mimics inhibited the luciferase activity of the ERE construct (FIG. 6D). The disturbed estrogen signaling pathway caused cell proliferation inhibition and apoptosis (FIG. 9, 11). In this study, let-7b appears the most effective in inhibiting the ER-α protein and mRNA levels, cyclin D1 expression, pS2 expression, and in affecting the p2 ERE-tk-luc construct (FIG. 6), cell proliferation (FIG. 7), and cell apoptosis (FIG. 11). This is not because let-7b is more powerful but because it had the highest quantity in our working system although starting concentration was the same (60 nmol/L). We consistently got highest let-7b expression with different batches of miRNA mimics and at different times in MCF7 cell line. It is either because let-7b mimic had higher transfection efficiency or was more resistant to degradation. The effect of the three miRNAs was consistent with corresponding quantities of forced expression in MCF7 cell line. Let-7a had the least expression (FIG. 6C) and had the least effect on ER-α function; let-7b had the highest expression and had the strongest function; and let-7i had the moderate expression and had moderate function. The low forced expression level of let-7a offers explanation for the inconsistency of its effect throughout the study. Our result actually strengthens the assumption that let-7 family members have similar target genes and similar functions (Schickel et al., 2008, Oncogene 27:5959-74, Pasquinelli et al., 2000, Nature 408:86-9). The result of let-7i further illustrates this point because, although it is not downregulated in MCF7 cell line (FIG. 1D), the forced overexpression of let-7i has largely similar effect as let-7b. Additionally, anti-let-7 inhibitors decrease the level of each other and similarly boosted the expression of ER-α (FIG. 8).

Let-7 miRNAs are extremely important for cell differentiation and carcino genesis (Medina and Slack, 2008 Cell Cycle 7:2485-92). Let-7 family miRNAs are reported to be tumor suppressors that play critical roles in tumorigenesis and metastatic progression of many diseases such as lung, colon, ovarian, and breast cancers (Yu 2007, Cell 131:1109-23, Michael et al., 2003 Mol Cancer Res 1:882-91, Takamizawa et al., 2004 Cancer Res 64:3753-6, Dahiya et al., 2008, PLoS One 3:e2436). Although many target genes for let-7 family miRNAs have been found, our research led to the discovery of another important target, ER-α. Our result offers another explanation for the carcinogenesis of ER-α breast cancer, which is that the down-regulation of let-7 miRNAs caused the up-regulation of ER-α and caused a series of downstream events (FIG. 11C). It is reported that cyclin D1 is the direct target of let-7 in other cancers (Schultz et al., 2008, Cell Res 2008; 18:549-57) (31). Therefore, the regulation of let-7 miRNAs on cyclin D1 could be a double "blow"—one is direct, the other is indirect, through ER-α.

Our conclusion that let-7 targets ER-α does not contradict the two recent reports that let-7 levels are lower in ER-α negative breast cancer than in ER-α positive cancer (Mattie et al., 2006, Mol Cancer 5:24, Blenkiron et al., 2007, Genome Biol 8:R214). Because we have only a few ER-α negative tissues in our study, we cannot compare the let-7 levels between these two subtypes. However, we do observe similar decrease in let-7 level in breast cancer cell lines (FIG. 1D). Our reasoning is that ER-α breast cancer develops from benign tissue, not from ER-α negative breast cancer. Therefore, the comparison between ER-α positive breast cancer and benign tissue offers clue for the regulation of ER-α by let-7. It is absolutely possible that ER-α negative cancers have even lower level of let-7, which may have other functions other than regulating ER-α. In fact, the function of let-7 in ER-α negative breast cancer is a good topic for future study.

In summary, we have compelling evidence showing that let-7 miRNAs are greatly reduced in breast cancer as they are in other cancers. Let-7, especially let-7b, targets ER-α, which is a critical component in breast cancer initiation and progression, and cause a halt in cell proliferation and cell apoptosis. For ER-α-positive breast cancer let-7 miRNAs could be candidate targets for drug therapies in the future.

Example 2

Let-7 microRNAs Induce Tamoxifen Sensitivity by Down-Regulation of Estrogen Receptor Alpha Signaling in Breast Cancer MicroRNAs (miRNAs) play an important regulatory role in breast tumorigenesis. Previously, we found that let-7 miRNAs were significantly downregulated in formalin fixed paraffin-embedded (FFPE) breast cancer tissues (Example 1). In order to further understand the potential role of let-7 miRNAs in breast cancer tissues, we found that endogenous levels of let-7 family miRNAs are inversely correlated with levels of estrogen receptor (ER)-α36, a new variant of ER-α66, in the FFPE tissue set. Bioinformatic analysis suggested that ER-α36 may be also a target of let-7 miRNAs. To test this hypothesis further, cotransfection of let-7 mimics with ER-α36 3' UTR luciferase construct was performed, and we found that let-7 mimics suppressed the activity of reporter gene significantly, which was restored remarkably by let-7 inhibitors. Transfection of let-7 mimics inhibited both mRNA and protein expression of ER-α36 and its mediated non-genomic estrogen signaling in triple negative breast cancer cell line MDA-MB-231 and tamoxifen (Tam) resistant MCF7 cells. Transfection of let-7 mimics to Tam-resistant MCF7 cells enhanced the sensitivity of the MCF7 cells to Tam, resulting in apoptosis of Tam resistant MCF7 cells. Our results suggested a novel regulatory mechanism of let-7 miRNAs on ER-α36 mediated Tam resistance.

Material and Methods

Cell Culture

All breast cancer cell lines were obtained from American Type Culture Collection (Manassas, Va.). The normal breast cell line 184A1 was cultured in 10% Fetal Bovine Serum (FBS) and MEGM (MEBM plus SingleQuots, Clonetics). ER-positive breast cancer cell lines, MCF7, ZR-75-1, T47D and HB3396 were maintained in phenol-red free IMEM (Cellgro, Manassas, Va.) plus 10% FBS, 1% nonessential amino acid, 10 mmol/L HEPES and 2 µg/mL insulin. MDA-MB-231, MDA-MB-436, MDA-MB-468, and SKBR-3 were cultured in DMEM (Cellgro, Manassas, Va.) plus 10% FBS. Tamoxifen resistant MCF7 cell line (MCF7-Tam) was established by culturing ER-positive breast cancer MCF7 cells in 1 µmol/L tamoxifen over 6 months. All cells were incubated at 37° C. with 5% $CO_2$ atmosphere.

Quantitative Real-Time PCR

To analyze mature let-7 miRNAs with real-time PCR, total RNA was isolated from the cell lines using mirVana miRNA isolation kit (Ambion Inc., Austin, Tex.) or from FFPE tissues using the miRNeasy FFPE Kit (Qiagen, Valencia, Calif.) following the manufacturer's instructions. We collected FFPE breast tissues from 13 benign, 16 ductal carcinomas in situ (DCIS), and 15 invasive ductal carcinomas (IDC), all of which were prepared as 50 µm thick sheets. The benign breast tissues were from surgical resections of abnormal breast lesions with non-neoplastic phenotypes such as calcification, fibrocystic changes or stromal fibrosis. cDNA was synthesized using 100 ng total RNA in a reaction volume of 15 µL and following the protocol of Taqman microRNA reverse transcription kit (Applied Biosystems, Foster City, Calif.). After 15 dilution, 9 µl, cDNA mixture was used for real-time PCR in 20 µL reaction volume, including 10 µL of TaqMan universal PCR master mix (no ampErase UNG) and 1 µL Taqman probe (Applied Biosystems, Foster City, Calif.). Real-time PCR was performed on 7900HT realtime PCR instrument (Applied Biosystems). PCR was initiated by two holds of 52° C. 2 min and 94° C. 10 min each, followed by 40 cycles of 15 s at 95° C. and 1 min at 60° C. The level of each miRNA was expressed following the $2^{-\Delta Ct}$ method using the small nuclear RNA RNU48 as the internal reference.

To assess the expression levels of ER-α66 and ER-α36 with real-time PCR, total RNA was extracted using Trizol reagent (Invitrogen, Carsbad, Calif.). One microgram RNA was used for cDNA synthesis with the SuperScript III first-strand synthesis system (Invitrogen, Carsbad, Calif.). After 10 dilution, 4 μL cDNA was used in 20 μL reaction volume, which includes 4 μL of 1.5 μmol/L primers, 2 μL of 2 μmol/L probes, and 10 μL TaqMan universal PCR master mix with ampErase UNG (Applied Biosystems). The reaction condition was the same as miRNA real-time PCR. β-Actin was the internal control (Applied Biosystems, Foster City, Calif.). The primers for ER-α66 are: 5'-GCGGCCACGGACCAT (forward) (SEQ ID NO:20); 5'-TTCCCTTGGATCTGATG-CAGTA (SEQ ID NO:21) (reverse); 5'-FAM-CCATGAC-CCTCCACACCAAAGCATC-TAMRA-3' (probe) (SEQ ID NO:22). The primers for ER-α36 are: 5'-CAAGTGGTTTC-CTCGTGTCTAAAG (forward) (SEQ ID NO:23); 5'-ACGTCCACACACGGATTTGA (reverse) (SEQ ID NO:24); 5'-FAMTGGTCATAAGGCCTCACAGTATCCT-GCA TAMRA-3' (probe) (SEQ ID NO:43).

miRNA Transfection

Let-7 miRNA or negative control #1 miRNA of 60 nmol/L (Ambion, Austin, Tex.) was transfected into cells with the siPORT NeoFX reagent (Ambion, Austin, Tex.) following the manufacturer's protocol.

Immunoblotting Analysis

Cells were lysed with NP40 cell lysis buffer (250 mM NaCl, 50 mM Tris-HCl, pH 7.4, 5 mM EDTA, 50 mM NaF, 1 mM Na3VO4, 1% Nonidet P40, 1 mM PMSF, proteinase and phosphoproteinase inhibitor cocktails). The protein was also extracted from FFPE sections. FFPE sections (50 μm thick) were transferred into a microcentrifuge tube and treated with xylene, followed by vortexing vigorously for 10 seconds. After centrifugation and removal of supernatant, the sections were washed with xylene two more times, followed by one more wash with 1 mL of 100% ethanol. The resultant pellets were vacuum dried, then resuspended in 300 μL of 20 mM Tris-HCl (pH 8.0) and 2% SDS and homogenized. The samples were then boiled at 100° C. for 20 minutes and incubated at 60° C. for 1 hour. After centrifugation at 10,000 g for 15 min at 4° C., the supernatant protein was saved for immunoblot analysis.

After mixed with gel-loading buffer and boiled for 5 minutes, the protein samples were separated with 10% SDS-PAGE and transferred to a PVDF membrane (Millipore, Billerica, Mass.). The blots were probed with specific first antibodies and appropriate second antibodies. The blots were visualized with enhanced chemiluminescence (ECL) reagents (Pierce, Minneapolis, Minn.) and documented with a Fluor Chem FC2 (Alpha Innotech, Santa Clara, Calif.) image system. Gel density was quantified with Quantity One and expressed as a relative value against β-actin. The anti-ERK1/2 (#9102) and antipERK1/2 (#9106) were purchased from Cell Signaling Technology (Danvers, Mass.). Anti-ER-α66 (RB-9016) was obtained from Thermoscientific (Rockford, Ill.). Anti-ER-α36 antibody was an affinity-purified rabbit polyclonal anti-ER-36 antibody generated as a custom service from Pacific Immunology Corp (Ramona, Calif.). The ER-α36 antibody was raised against a synthetic peptide antigen corresponding to the unique C-terminal 20 aa of ER-α36.

Luciferase Assay

A fragment of the 3' UTR of human ER-α36 gene, which harbors the putative let-7 target sites, was synthesized (IDT, Coralville, Iowa). With the SpeI and HindIII restriction sites at the ends, respectively, the sense strand is 5'-ctagTGTTC-CCTAGAAACACCAGGAAGGCCTACCT-CAAATAGCAACAA (SEQ ID NO:41) and the antisense strand is 5'-agctTTGTTGCTATTTGAGGTAGGCCT-TCCTGGTGTTTCTAGGGAACA (SEQ ID NO:42). The corresponding mutant sequences were generated as shown in FIG. 13. The sense and antisense oligonucleotides were annealed and ligated into the SpeI/HindIII sites of the pMIR-REPORT luciferase vector (Ambion, Austin, Tex.). The sequences were verified by DNA sequencing. Transfection was performed in 24-well plate using Lipofectamine 2000 (Invitrogen). Let-7 mimics, anti-let-7 inhibitors, or negative controls were transfected with 0.25 μg luciferase construct and 0.25 μg β-galactosidase plasmid (Ambion) to check transfection efficiency. Twenty-four hours post-transfection, the luciferase activity was measured using Dual-Glo Luciferase Assay System (Promega, Fitchburg, Wis.) in Veritas Microplate Luminometer (Turner Biosystems, Sunnyvale, Calif.).

MTT Cell Proliferation Assay

MCF7-Tam cells were transfected with let-7 mimics or negative control in normal growth medium for 1 day, or in medium with 2.5% charcoal-stripped FBS for 2 days to exhaust endogenous estrogen. Ten thousand cells in the volume of 100 μL were seeded in a 96-well plate for 12 hours and assay lasted for another 4 days. For tamoxifen treatment, 1 μmol/L tamoxifen was added to each well of 96-well plate. Each treatment had 12 replicates on the plate. Medium volume was increased to 200 μL after the assay began. The cells were then incubated in 0.83 mg/mL 3-[4,5-dimethylthiazol-2-yl]-2,5-diphenyltetrazolium bromide (MTT) in growth medium at 37° C. for 4 hours and lysed in 100 μL of dimethyl sulfoxide at room temperature for 15 minutes. The absorbance in each well was measured at 490 nmol/L with an ELx800 Absorbance Microplate Reader (Biotek, Winooski, Vt.). Cell growth was expressed as a fraction of absorbance at day 0.

Statistical Analysis

The correlation between let-7 miRNA expression and ER-α36 was analyzed in SPSS16.0 (SPSS Inc., Chicago, Ill.). For comparison among means of different treatments, oneway ANOVA with the Tukey's adjustment was used for multiple comparisons in SPSS 16.0. * represents $p<0.05$; ** represents $p<0.01$.

Results

ER-α36 is Widely Expressed in Breast Cancer Cell Lines

After the cloning and identification of ER-α36 in 2005 (Wang et al., 2005, Biochem. Biophys. Res. Commun. 336: 1023-7), its important function has just begun to be recognized. We first checked the ER-α36 expression in some established breast cancer cell lines (FIG. 12A) and found that ER-α36 was expressed in both ER-α66 positive and negative cell lines. ER-α36 is highly expressed in ER-α66 negative cell lines: SK-BR-3, MDA-MB-231, MDA-MB-436, and MDA-MB-468. It was also highly expressed in ER-α66 positive cell lines: T47D, HB3396, and ZR-75-1. However, there was only trace expression in the classical ER-α66 positive cell line MCF7. FIG. 12A shows the expression of Her2, ER-α66, and ER-α36 in breast cancer cell lines.

Let-7 miRNAs Target ER-α36

Recently, we reported that the let-7 family miRNAs are involved in regulation of ER-α66 expression (Zhao Y et al., 2010, Breast Cancer Res. Treat, DOI: 10.1007/s10549-010-0972-2). To examine if let-7 miRNAs also regulate ER-α36 expression, we extracted proteins and total RNAs from 45 cases of FFPE breast cancer samples and assessed the expression levels of ER-α36 and let-7 miRNAs with Western blot and realtime PCR 25 analysis, respectively. We found an inverse correlation between ER-α36 expression and two members of let-7 family miRNAs (let-7b and let-7i) (FIG. 12B). A strong complementary match was found between let-7 miRNAs and 3'-UTR of ER-α36 gene (FIG. 13A); the seed regions of let-7 miRNAs pair perfectly with the corresponding region located in the 3'-UTR of ER-α36 gene. The ΔG of the RNA duplex is −15.8 30 kcal/mole between the 3'-UTR of ER-α36 and let-7i Zuker et al., 1999, In: RNA Biochemistry and Biotechnology, Barciszewski and Clark, eds., NATO ASI Series, Kluwer Academic Publishers). To determine whether ER-α36 expression is subjected to regulation of let-7 miRNAs, the putative binding and flanking sequences in the 3'-UTR of ER-α36 were cloned into the 3'UTR of luciferase in the pMIR-REPORT plasmid. Co-transfection assays with 60 nmol/L let-7 miRNA mimics in MCF7 cells showed that both let-7b and let-7i potently decreased the luciferase activity, about 60% of the activity in the control cells transfected with nonfunctional negative control miRNA (FIG. 13B). Mutations in the putative let-7 miRNAs binding sequences in the 3'-UTR of ER-α36 abrogated the inhibitory effects of these miRNAs (FIG. 13C). The effect of let-7 inhibitors was also tested in co-transfection 10 assays in the normal mammary epithelial184A1 cell line that expresses high levels of let-7 miRNAs (Zhao et al., 2010, Breast Cancer Res. Treat, DOI: 10.1007/s10549-010-0972-2). We found that let-7b and let-7i inhibitors strongly increased the activity (2-3 fold) of the luciferase reporter gene carrying the putative binding site from the 3'-UTR of ER-α36 gene (FIG. 13D).

To further determine the inhibitory effects of let-7b and let-7i on expression of endogenous ER-α36, we transfected their miRNA mimics separately into ER-α66 negative breast cancer MDA-MB-231 cells that express high levels of ER-α36. We found that transfection of both let-7b and let-7i strongly inhibited ER-α36 at the protein level compared to cells transfected with negative control miRNA (FIG. 14A). At the mRNA level, real-time PCR analysis indicated that the two miRNA mimics had similar inhibitory effect on ER-α36 mRNA expression (30% of the controls transfected with the negative control miRNA, FIG. 14B), indicating that let-7 miRNAs inhibited ER-α36 expression. The expression levels of let-7b and let-7i after 2 days of miRNA mimic transfection was shown in FIG. 14C. Let-7b achieved ~400 fold increase and let-7i reached ~200 fold compared to the negative control cells.

ER-α36 is mainly localized on the plasma membrane and mediates the non-genomic estrogen pathways (Wang et al., 2005, Biochem. Biophys. Res. Commun. 336:1023-7, Wang et al., 2006, Proc. Natl. Acad. Sci. U.S.A., 103:9063-8). We reasoned that the inhibition on ER-α36 expression by let-7 family miRNAs might dampen the non-genomic estrogen pathway. To test this, we examined the activation of the MAPK/ERK signaling by estrogen in cells transfected with let-7 miRNAs. The MDA-MB-231 cells transfected with let-7b and let-7i mimics or negative control were cultured in 2.5% charcoal-stripped FBS for 48 h and starved in serum free medium for 24 h. The transfected cells were then treated with 10 nmol/L of E2 and the activation of ERK1/2 was examined with Western blot analysis using phos-ERK specific antibody. Transfection of let-7b and let-7i significantly inhibited estrogen induced activation of the ERK1/2 (FIG. 14D) presumably through down-regulation of ER-α36 expression. This result indicates that let-7 miRNAs is involved in regulation of the non-genomic estrogen pathway.

To confirm the result, normal mammary epithelial 184A1 cells were transfected with anti-let-7b, anti-let-7i inhibitor, or negative control miRNA. FIG. 14E shows that both let-7 inhibitors significantly enhanced the levels of ER-α36 protein and mRNA expression. FIG. 3F) while reduced the levels of let-7b and let-7i miRNAs (FIG. 3G).

Let-7 miRNA and ER-α36 Expression in the MCF7-Tam Cell Line

Figure 15:
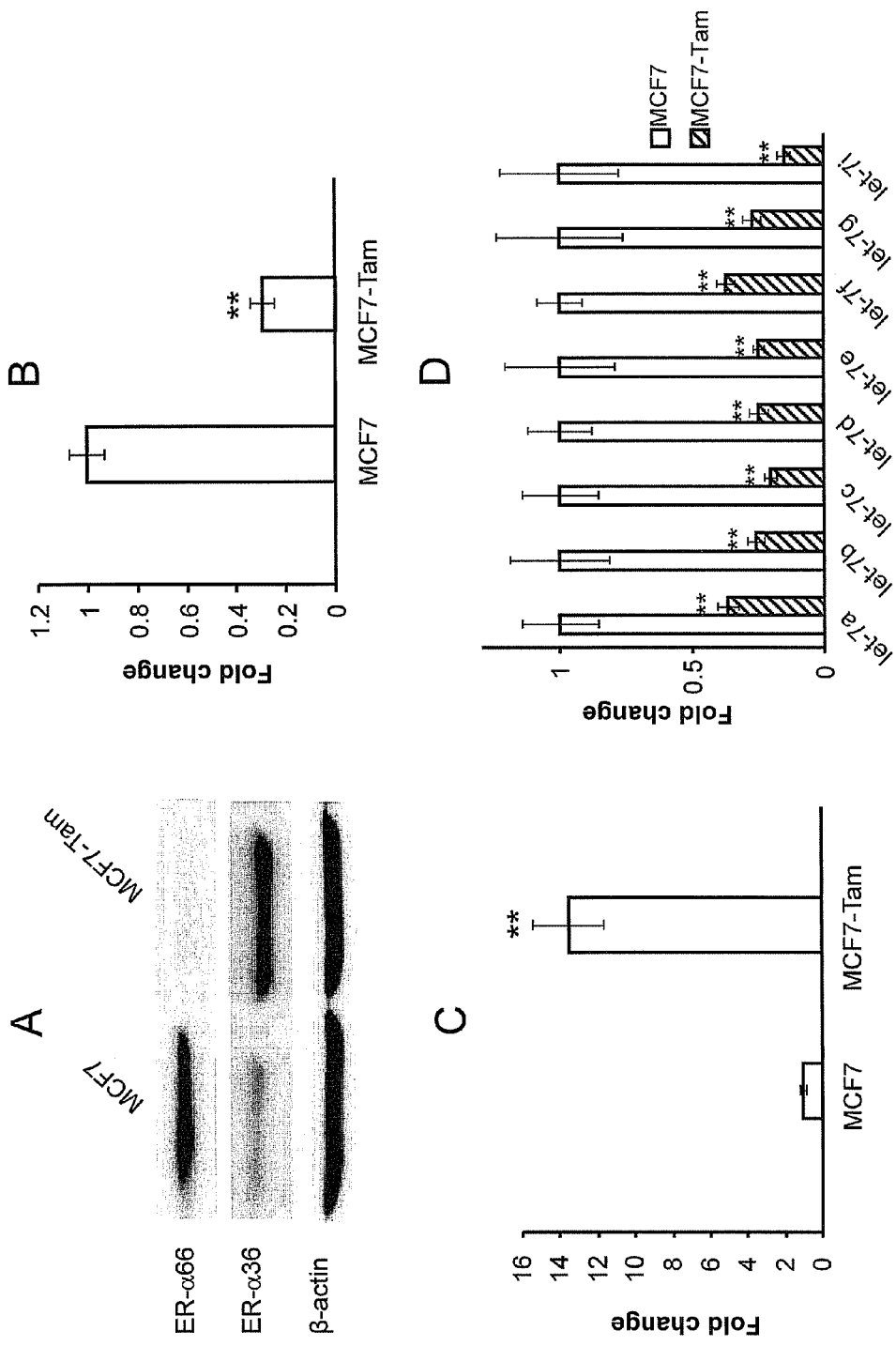
FIG. 15. A), ER-α66 protein expression is inhibited and ER-α36 protein expression is enhanced in MCF7 tamoxifen resistant (MCF7-Tam) cell line compared to parental MCF7. B), mRNA of ER-α66 is reduced in MCF7-Tam cell line. C), mRNA of ER-α36 is enhanced in MCF7-Tam cell line. D), all let-7 miRNAs are downregulated in MCF-7 Tam cell line. **, p<0.01.

Anti-estrogen resistance is a major obstacle in clinical breast cancer treatment. However, the exact mechanism is still unknown. In a tamoxifen resistant MCF7 cell line, MCF-Tam, we found that ER-α36 protein level was greatly increased, whereas ER-α66 protein was greatly reduced to trace level (FIG. 15A). The mRNA level of ER-α66 in MCF7-Tam was ~30% of parent cell line (FIG. 4B). ER-α36 mRNA expression in MCF7-Tam increased about 14 folds compared to tamoxifen sensitive parental MCF7 cells (FIG. 15C). Meanwhile, let-7 miRNA levels in MCF7-Tam cells were significantly reduced to less than half of the levels in parental MCF7 cells (FIG. 15D). Thus, there is inverse relationship between ER-α36 and let-7 miRNA expression. We then examined whether transfection of let-7 miRNAs could decrease the ER-α36 expression in MCF7-Tam cells. We found that transfection of the let-7 miRNA mimics, significantly decreased both protein and mRNA levels of ER-α36 (FIGS. 16A, C). This inhibition lasted for 6 days (FIGS. 16B, C). Transfection of let-7b and let-7i mimics achieved ~600 and ~300 fold increase of levels of let-7 b and let-7i, two days after transfection and 100 fold compared to negative control 6 days after transfection (FIGS. 16D).

Recently, we reported that the enhanced expression of ER-α36 is involved in tamoxifen resistance (Shi et al., 2009, J. Clin. Oncol., 27:3423-9). We then examined the tamoxifen sensitivity in tamoxifen resistant MCF7-Tam cells transfected with let-7 miRNAs or negative control miRNA. When grown in complete medium, which contained estrogen, no difference was detected between let-7 transfection and negative control transfection (FIG. 16E) with tamoxifen in the medium. However, when grown in E2 free medium, those cells transfected with let-7b or let-7i grew significantly slower than those transfected with negative control miRNA with tamoxifen in the medium (FIG. 16F), which demonstrates that let-7 miRNAs increase tamoxifen sensitivity by decreasing ER-α36 expression.

Discussion

ER-α36 is the product of a transcript initiated from the promoter located in the first intron of ER-α66 gene. ER-α36 is expressed in tumor tissues from ER-α66 positive and negative breast cancer patients (Shi et al., 2009, J. Clin. Oncol., 27:3423-9). Thus, breast cancer patients who are clinically characterized as ER-negative (lack of the nuclear ER-α66 expression) may still express ER-α36 (Wang et al., 2006, Proc. Natl. Acad. Sci. U.S.A., 103:9063-8, Shi et al., 2009, J. Clin. Oncol., 27:3423-9). ER-α36 inhibits the transcription regulatory function of ER-α66 and ER-β (Wang et al., 2006, Proc. Natl. Acad. Sci. U.S. A., 103:9063-8) while ER-α66 down-regulates the promoter activity of ER-α36 (Zou et al., 2009, FEBS Lett. 583:1368-74). We also found that ER-α36 was expressed in both ER-α66 positive and -negative cell lines (FIG. 12A), indicating its important function in breast cancer.

Figure 14:
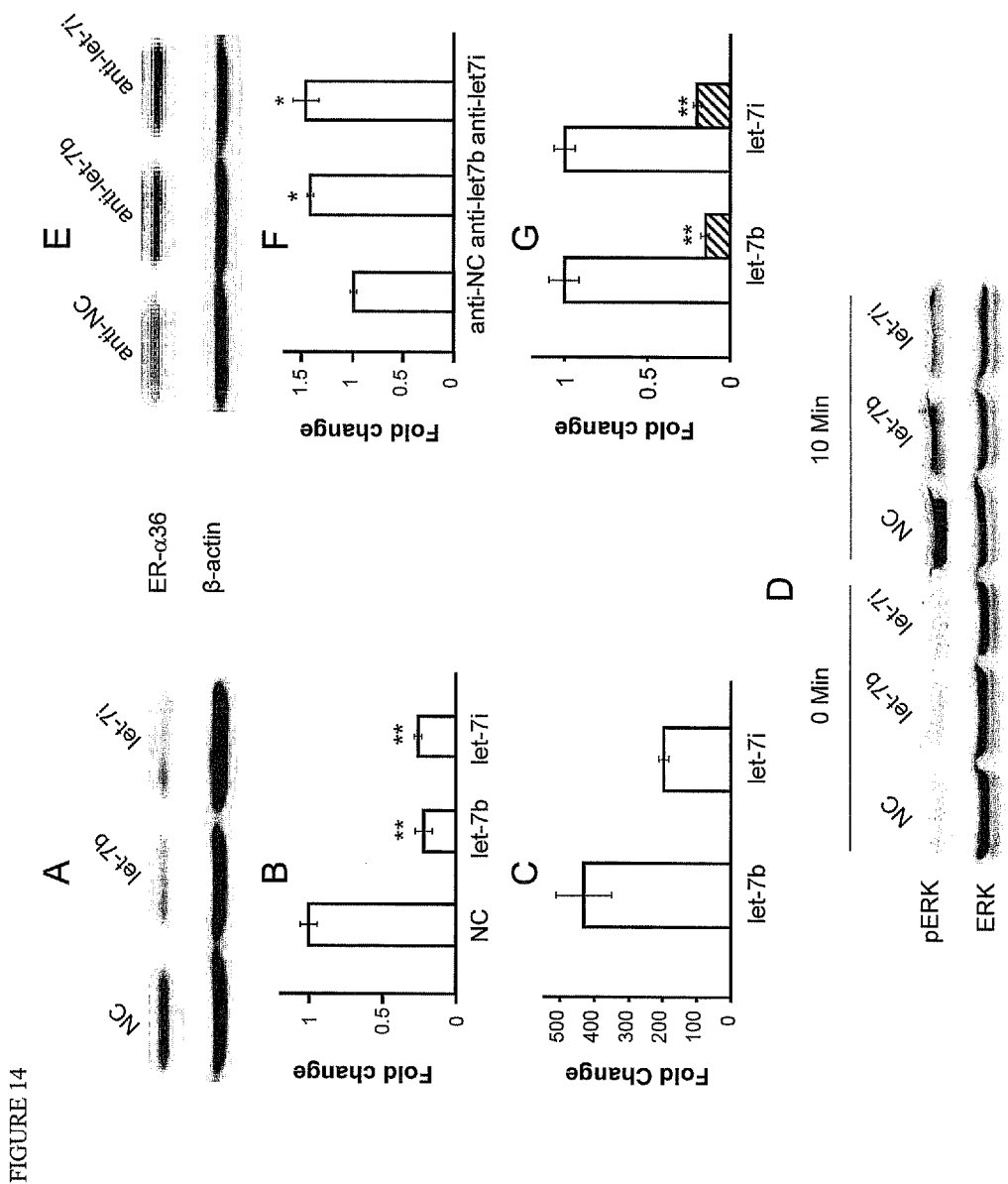
FIG. 14. Transfection results in different cell lines. The protein level (A) and mRNA level (B) of ER-α36 were inhibited after two days post transfection of let-7b and let-7i in MDA-MB-231 cell line. C), successful transfection of let-7b and let-7i in MDA-MB-231 cell after 2 days. D), the nongenomic estrogen pathway was significantly inhibited after transfection of let-7b and let-7i miRNAs. Post transfection, MDA-MB-231 cell was cultured in IMEM with 2.5% charcoal-stripped FBS for 2 days and in IMEM with 1 mg/ml BSA for 1 day before 10 nmol/L or vehicle stimulation. The protein level (E) and mRNA level (F) of ER-α36 were promoted after two days post transfection of anti-let-7b and anti-let-7i in 184A1 cell line. C), successful knockdown of let-7b and let-7i after transfection of anti-let7b and anti-let7i in 184A1 cell for 2 days. *, p<0.05; **, p<0.01.

Let-7 family miRNAs are the first miRNAs discovered in human (Roush and Slack, 2008, Trends Cell Biol. 18:505-16), and play important roles in maintaining sternness (Yu et al. 2007, Cell 131:1109-23). Dysregulated let-7 miRNA expression is involved in carcinogenesis (Jerome et al., 2007, Curr. Genomics 8:229-33). The expression of let-7 miRNAs increases with differentiation and cancer development (Yu et al. 2007, Cell 131:1109-23). The low level of let-7 miRNAs in stem cell is caused by uridylation mediated by Lin28 in concert with TUT4 (Heo et al., 2008, Mol. Cell. 32:276-84, Heo et al., 2009, Cell 138:696-708). Because cancer cells have similar stemness with stem cells, let-7 miRNAs are down-regulated in many types of cancers, including breast cancer (Michael et al., 2003, Mol. Cancer. Res. 1:882-91, Takamizawa et al., 2004, Cancer Res., 64:3753-6, Dahiya et al., 2008, PLoS. One. 3:e2436, Yu et al. 2007, Cell 131:1109-23, Kumar et al., 2008, Proc. Natl. Acad. Sci. U.S.A 105:3903-8). Some targets of let-7 family have been found, including Ras, HMGA2, and c-Myc (Johnson et al., 2005, Cell, 120:635-47, Lee and Dutta, 20007, Genes Dev. 21:1025-30, Mayr et al., 2007, Science 315:1576-9, Kim et al., 2009, Genes Dev. 23:1743-8). Previously, we found that let-7 family miRNAs target ER-α66 and down-regulate its expression (Zhao Y et al., 2010, Breast Cancer Res. Treat. DOI: 10.1007/s10549-010-0972-2]) suggesting let-7 miRNA play an important role in development of ER-α66 positive breast cancer. In this study, we present strong evidence to demonstrate that let-7 miRNAs also regulate a variant of ER-α66, ER-α36. The luciferase assay with the report gene harboring 3'UTR of ER-α36 indicated that let-7 miRNAs directly regulate ER-α36 expression (FIG. 13). The findings of inverse correlation between the expression of let-7 and ER-α36 (FIG. 12B), and the down-regulation of ER-α36 by let-7 miRNA transfection (FIG. 14) demonstrated that let-7 family miRNAs regulate ER-α36 expression. The results that let-7 miRNA transfection impeded the non-genomic estrogen pathway (FIG. 14) and enhances tamoxifen sensitivity in MCF7-Tam cells (FIG. 16) further indicated that let-7 family miRNA also regulates estrogen and antiestrogen signaling presumably through regulation of ER-α36 expression. Previous study shows that the knockdown of GPR30 does not affect nongenomic estrogen pathway, but knockdown of ER-α36 significantly affects nongenomic estrogen pathway (Kang et al., 2010, Mol. Endocrinol., 24:709-21). The compound G1, which was regarded as the ligand of GPR30, actually binds to ER-α36. Besides, ER-α36 binds to estrogen in vitro (Kang et al., 2010, Mol. Endocrinol., 24:709-21). Our experiment strengthens the concept that ER-α36 was the membrane estrogen receptor, which mediates nongenomic estrogen pathway, because knockdown of ER-α36 by let-7 significantly decreases the phosphorylation of ERK, which is an important component of MAPK pathway (FIG. 14).

Figure 16:
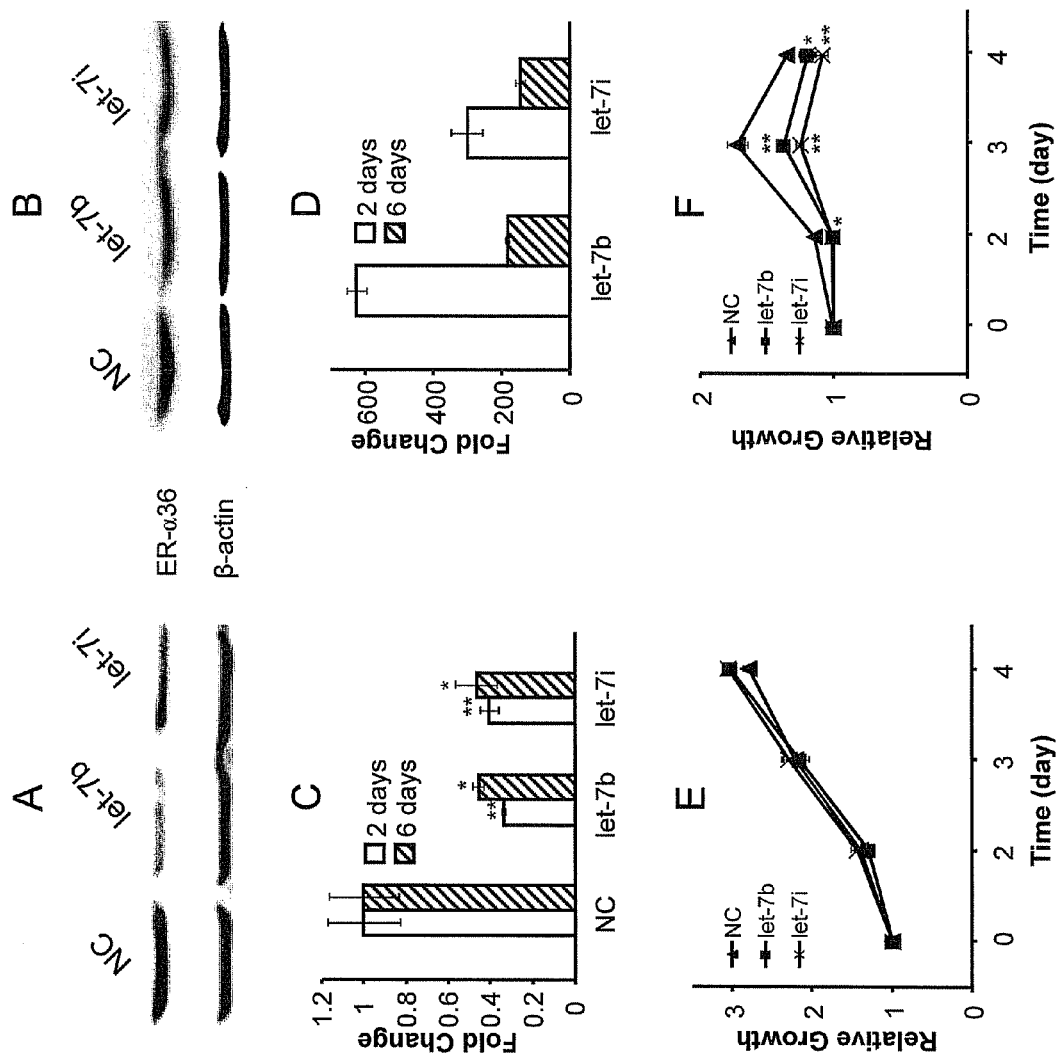
FIG. 16. Knock down of ER-α36 by let-7b and let-7i increased tamoxifen sensitivity in MCF7-Tam. The protein level of ER-α36 after 2 days (A) and 6 days (B) post transfection of let-7b and let-7i. C), the mRNA level of ER-α36 after transfection of let-7b and let-7i. D), the forced overexpression of let-7b and let-7i detected by real-time PCR. E), the transfection of let-7b and let-7i does not affect tamoxifen sensitivity of MCF7-Tam in normal growth medium with 10% FBS. F), transfection of let-7b and let-7i significantly enhanced tamoxifen sensitivity of MCF7-Tam in growth medium with 2.5% charcoal-stripped FBS. *, p<0.05; **, p<0.01.
Figure 17:
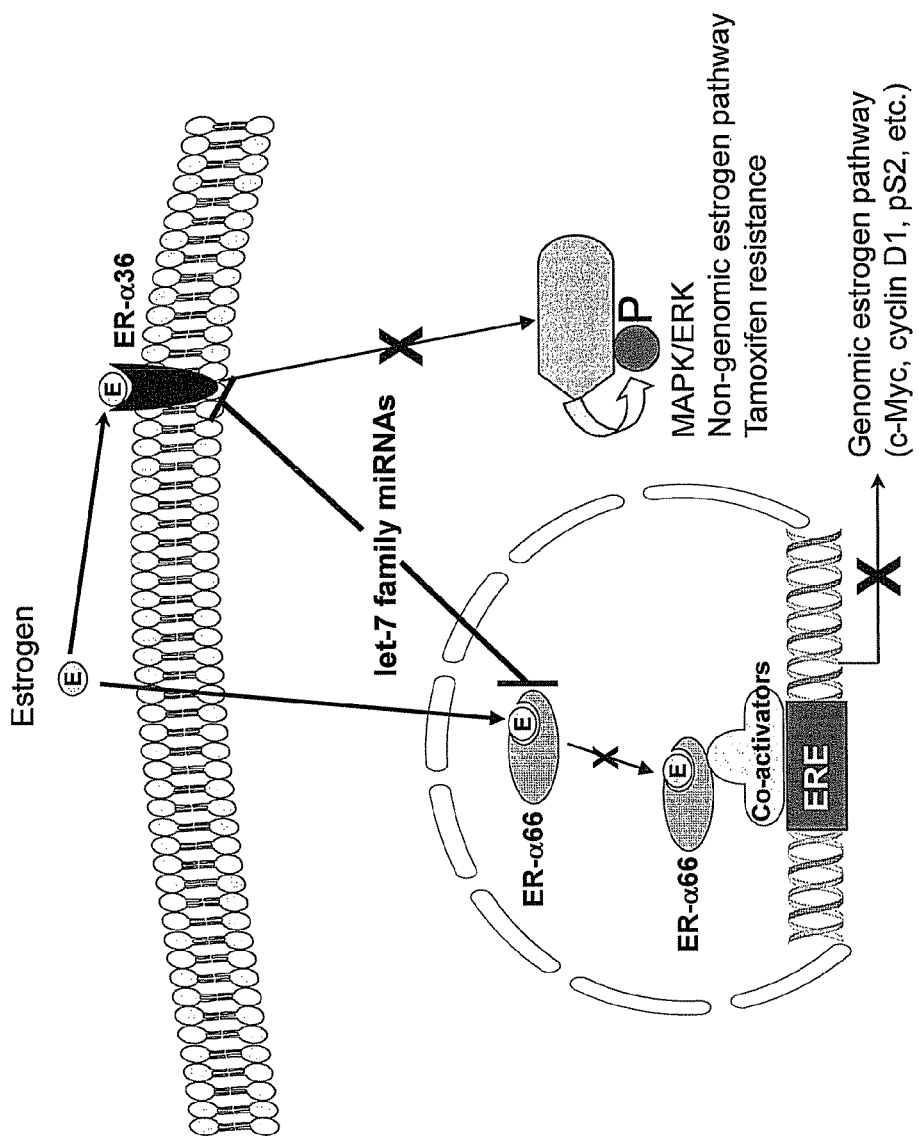
FIG. 17. A schematic diagram about the regulatory role of let-7 miRNAs on ER-α66 mediated genomic estrogen signaling and ER-α36 mediated nongenomic estrogen signaling in breast cancer.

Tamoxifen is the most successful adjuvant therapy drug for ER-positive breast cancer patients. It is well-known that tamoxifen acts as both agonist and antagonist of estrogen signaling. The acquired and de novo tamoxifen resistance in breast cancer patients is a significant clinical problem. Our current study revealed that MCF7-Tam cells exhibits enhanced expression of ER-α36 and decreased expression of ER-α66 (FIGS. 15A-C) suggesting that ER-α36 is involved in tamoxifen resistance. Previous study showed that tamoxifen acts as an agonist in ER-α36-expressing cells by activation of the MAPK/ERK signaling pathway (Wang et al., 2006, Proc. Natl. Acad. Sci. U.S.A., 103:9063-8) and patients who have expression of both ER-α66 and ER-α36 will benefit less from tamoxifen treatment (Shi et al., 2009, J. Clin. Oncol., 27:3423-9). Here, we found that let-7 family miRNAs are down-regulated in MCF7-Tam cells that have an enhanced expression of ER-α36 (FIG. 15D). The transfection of let-7b and let-7i miRNA not only inhibited the expression of ER-α36, but also enhanced the tamoxifen sensitivity in MCF7-Tam cells (FIG. 16). Therefore, our study indicates that downregulation of let-7 miRNAs causes upregulation of ER-α36, which causes tamoxifen resistance. ER-α36 is an important predictive marker for tamoxifen therapy in ER-α66 positive breast cancer patients. In fact, tamoxifen can cause more endurable ERK phosphorylation than estrogen in ER-α36 expressing cells (Wang et al., 2006, Proc. Natl. Acad. Sci. U.S.A., 103:9063-8). Combined with our previous study (Zhao et al., 2010, Breast Cancer Res. Treat., DOI: 10.1007/s10549-010-0972-2), let-7 miRNAs can regulate the expression of both ER-α66 and ER-α36 in breast cancer. The down-regulation of let-7 miRNAs in breast cancer causes the upregulation of ER-α66 and ER-α36. ER-α66 mediates the genomic estrogen pathway, which includes the downstream transcription of c-Myc, cyclin D1, and pS2, etc. ER-α36 mediates the non-genomic estrogen pathway, which includes phosphorylation of ERK, tamoxifen resistance, etc. Overexpression of let-7 miRNAs can effectively inhibit these two pathways (FIG. 17).

In conclusion, Let-7 miRNAs regulate the expression of ER-α36, resulting in enhanced sensitivity to tamoxifen treatment in breast cancer. Let-7 could be therapeutic target for breast cancer treatment.

Example 3

MicroRNAs Let-7 can be Used as Biomarker for Early Detection of Breast Cancer

Results from our previous studies and others showed that endogenous miRNAs are expressed differentially in breast cancer tissues at various stages, suggesting that these miRNAs can be developed as potential biomarkers useful for early diagnosis, prognosis, and therapy of breast cancer (Zhao et al., 2010, Breast Cancer Res. Treat. DOI: 10.1007/s10549-010-0972-2, Mitchell et al., 2008, Proc. Natl. Acad. Sci. U.S.A 29; 105:10513-8, Heneghan et al., 2010, Ann. Surg. 251:499-505). Recent reports confirmed the association between differentially expressed miRNAs and several clinicopathologic features, including mRNA expression-based classification (Blenkiron et al., 2007, Hum. Mol. Genet. April 15; 16 Spec No 1:R106-R113), tumor grade, and clinical stage scoring (Iorio et al., 2005, Cancer Res. 65:7065-70). Generally, these miRNAs related to cancer can be classified into two categories: tumor suppressors (e.g. let-7, miR-335) and oncogenic enhancers (e.g. miR-375, miR-155) (Zhao et al., 2010, Breast Cancer Res. Treat. DOI: 10.1007/s10549-010-0972-2, and also Table 6). The ideal biomarker should be easily accessible such that it can be sampled relatively non-invasively (e.g. blood draw), sensitive enough to detect early presence of tumors in almost all patients and absent or minimal present in healthy, tumor-free individuals. Although the diagnostic and prognostic use of circulating miRNAs as blood-based biomarkers has recently been revealed (Gilad et al., 2008, PLoS. One. 3 (9):e3148, Ng et al., 2009, Gut 58 (10):1375-81, Wang et al., 2009, Proc. Natl. Acad. Sci. U.S.A 106:4402-7), challenge for this field still remains regarding the feasibility and reliability of serum miRNAs use as surrogate diagnostic markers of cancer or asymptomatic population screening tool (Wang et al., 2010, Gynecol. Oncol. 119 (3):586-593).

TABLE 6

Differential expressed miRNAs in DCIS and invasive ductal carcinoma (IDC) FFPE samples compared to benign samples based on normalized data. p < 0.01.

| Regulation | Name of microRNAs |
|---|---|
| Up-regulated | hsa-miR-155 |
| | hsa-miR-375 |
| | hsa-miR-1826 |
| | hsa-miR-1280 |
| | hsa-miR-1274b |
| | hsa-miR-720 |
| | hsa-miR-342-3p |
| | hsa-miR-425 |
| | hsa-miR-21 |
| Down-regulated | hsa-miR-212 |
| | hsa-miR-205 |
| | hsa-miR-125b |
| | hsa-miR-99a |
| | hsa-miR-132 |
| | hsa-let-7b |
| | hsa-let-7a |
| | hsa-let-7c |
| | hsa-miR-423-5p |
| | hsa-miR-768-5p |
| | hsa-miR-379 |
| | hsa-miR-497 |
| | hsa-miR-34a |
| | hsa-miR-145 |
| | hsa-miR-335 |
| | hsa-miR-195 |

In the development of a clinical blood-based biomarker, the following factors should be generally considered: 1) whether miRNAs expressed in breast tumor are correlated with those in the circulation; 2) whether circulating miRNA biomarkers are stable enough to withstand storage conditions e.g. temperature variations (including freezing and thawing and potential influence of physiological conditions of women such as menstrual cycle, age, and menopausal status; 3) and whether data obtained from the individuals with same status of the disease is identical. Recently, results from several studies regarding development of clinical accessible assays using miRNAs showed that: a) A high correlation of miRNAs expression level was found between breast tumor tissues and sera (Wang et al., 2010, Gynecol. Oncol., 119 (3):586-593); b) A high correlation of miRNAs expression level was found between plasma and sera (Mitchell et al., 2008, Proc. Natl. Acad. Sci. U.S.A 29; 105:10513-8); c) serum miRNAs were found stable in numbers of clinical lab conditions such as temperature and freeze/thaw (Mitchell et al., 2008, Proc. Natl. Acad. Sci. U.S.A 29; 105:10513-8); d) spiked unrelated exogenous miRNAs as external control were found useful for enhancing reliability of qRT-PCR assays (Mitchell et al., 2008, Proc. Natl. Acad. Sci. U.S.A 29; 105:10513-8). Although several other studies have confirmed this protocol in clinic (Mitchell et al., 2008, Proc. Natl. Acad. Sci. U.S.A 29; 105:10513-8), how women's physiological conditions such as menstrual cycle and age, affect on clinical assays are still not clear. In this aim, using the established conditions in our lab, we performed analysis of the correlation of expression level of several dysregulated miRNAs (from Table 6 and additional significant miRNAs) associated with breast cancer, at precancerous and early invasive carcinoma, between tissue and matching serum samples.

Material and Methods

Plasma samples. Blood samples were obtained from 20 healthy female subjects and 20 breast cancer female subjects. After centrifuge at 1000 rpm for 30 min, the plasma was collected and frozen at −80° C.

RNA isolation from human plasma samples. Three hundred μl of plasma was thawed on ice and lysed with an equal volume of 2× Denaturing Solution (Ambion). For the purpose of normalization of sample-to-sample variation in RNA isolation, synthetic C. elegans miRNAs cel-miR-39, cel-miR-54, and cel-miR-238 (synthesized by Sigma) were added (as a mixture of 25 fmol of each oligonucleotide in a 7.5 μl total volume) to each sample after Denaturing Solution was added. RNA was isolated using the mirVana PARIS kit following the manufacturer's protocol for liquid samples (Ambion). RNA was eluted with 50 μl of nuclease-free water.

QRT-PCR. RNA was reverse transcribed using the TaqMan miRNA Reverse Transcription Kit and miRNA-specific stem-loop primers (Applied BioSystems) in a 15 μl reaction volume (6.16 μl of H2O, 1.5 μl of 10× Reverse-Transcription Buffer, 0.19 μl of RNase-Inhibitor, 0.15 μl of 100 mM dNTPs, 1 μl of Multiscribe Reverse-Transcriptase, and 3 μl of total RNA) using a GeneAmp PCR Systems 9700 at 16° C. for 30 min, 42° C. for 30 min and 85° C. for 5 min.

For realtime PCR, 9 μl of diluted RT product (prepared by combining 15 μl of RT product with 60 μl of H2O) was combined with 10 μl of TaqMan 2× Universal PCR Master Mix, No AmpErase UNG and 1 μl of TaqMan miRNA probe in 20 μl of total volume. Real-time PCR was carried out on an Applied BioSystems 7900HT thermocycler at 95° C. for 10 min, followed by 40 cycles of 95° C. for 15 s and 60° C. for 1 min.

Data Analysis. The Ct values obtained for the three spiked-in C. elegans miRNAs were averaged to generate SpikeIn_Average_Ct value. The mean value of the SpikeIn_Average_Ct values obtained from all of the samples to be compared was designated as the Mean_SpikeIn_Ct value. Normalized_Ct value for the miRNA in the sample=Raw Ct value−[(SpikeIn_Average_Ct value of the given sample)−(Mean_SpikeIn_Ct value)].

Number of copies per microliter plasma=$[2^{(Ct(SpikeIn\_Average\_Ct\ value\ of\ the\ sample)-Ct(sample))}](25\ fmol\ (10^{-15}\ mole)\ 6.02\ 10^{23}/300\ \mu L)$.

Results

Figure 20:
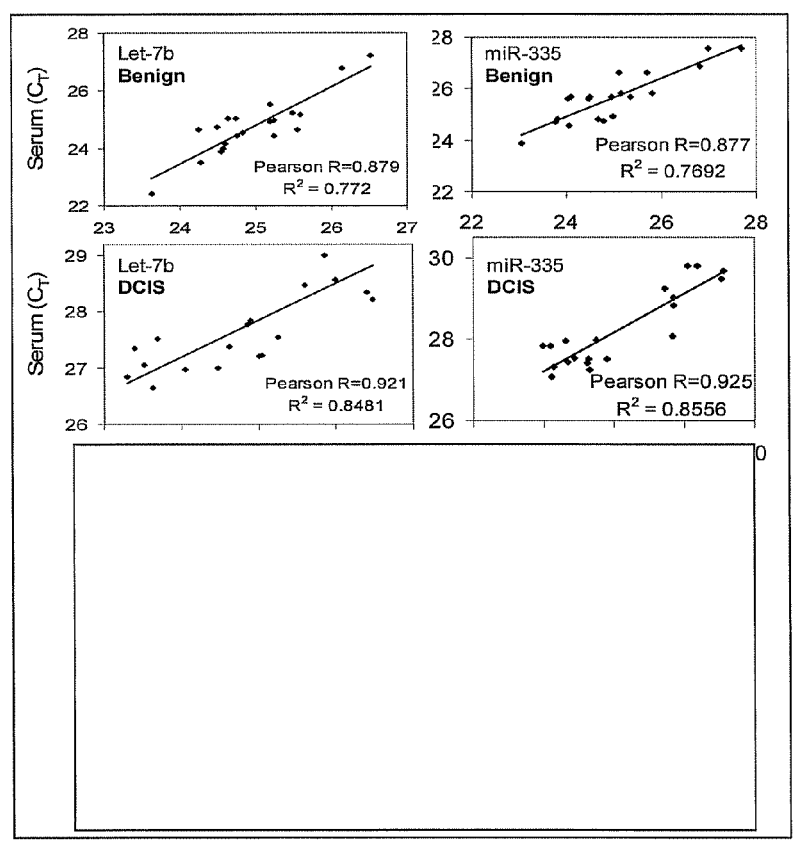
FIG. 20. Positive correlation of let-7b/miR-335 miRNAs' level between breast tissue and matching serum. Benign tissues were the adjacent tissues to DCIS and selected by LCM, Sera were collected from different population of healthy women (Yu et al., 2009, Breast Cancer Res. Treat. 118 (3): 661-3) and matching sera from women with breast cancer at DCIS (Yu et al., 2009, Breast Cancer Res. Treat. 118 (3):661-3). Total RNA was extracted from the selected breast tissues (about $6 \times 10^4$ cells per sample from ten core biopsies) and serum (300 ul each sample). The level of miRNAs was measured by using qRT-PCR (ABI 7900HT Fast real-time PCR systems). Correlation analyses of let-7b/miR-335 miRNAs were performed by using Pearson coefficient method. Linear regression model was used to estimate the R-square. All experiments were repeated three times.

First, Correlation analysis of miRNAs expression level in tissues and matching sera: Although a recent study reported a positive relationship between miRNA level in tissues and sera, we needed to establish assay conditions in our own laboratory. We selected FFPE breast tissue specimens from twenty women with breast cancer at the stage of DCIS and matching serum samples, and twenty serum samples from healthy women (age-matched to subjects with breast cancer) to perform qRT-PCR analysis of the selected miRNAs (tumor suppressors, let-7b and miR-335) (FIG. 20). For the purpose of normalization of sample-to-sample variation in RNA isolation, we used synthetic C. elegans miRNAs cel-miR-39, cel-miR-54, and cel-miR-238 (synthesized by Sigma) (Mitchell et al., 2008, Proc. Natl. Acad. Sci. U.S.A 105: 10513-8) as external controls to spike them (as a mixture of 25 fmol of each oligonucleotide in a 7.5 μl total volume) to each sample after induction of denaturing solution. As expected, these two selected miRNAs level in tissue and serum are highly correlated (FIG. 20).

Figure 21:
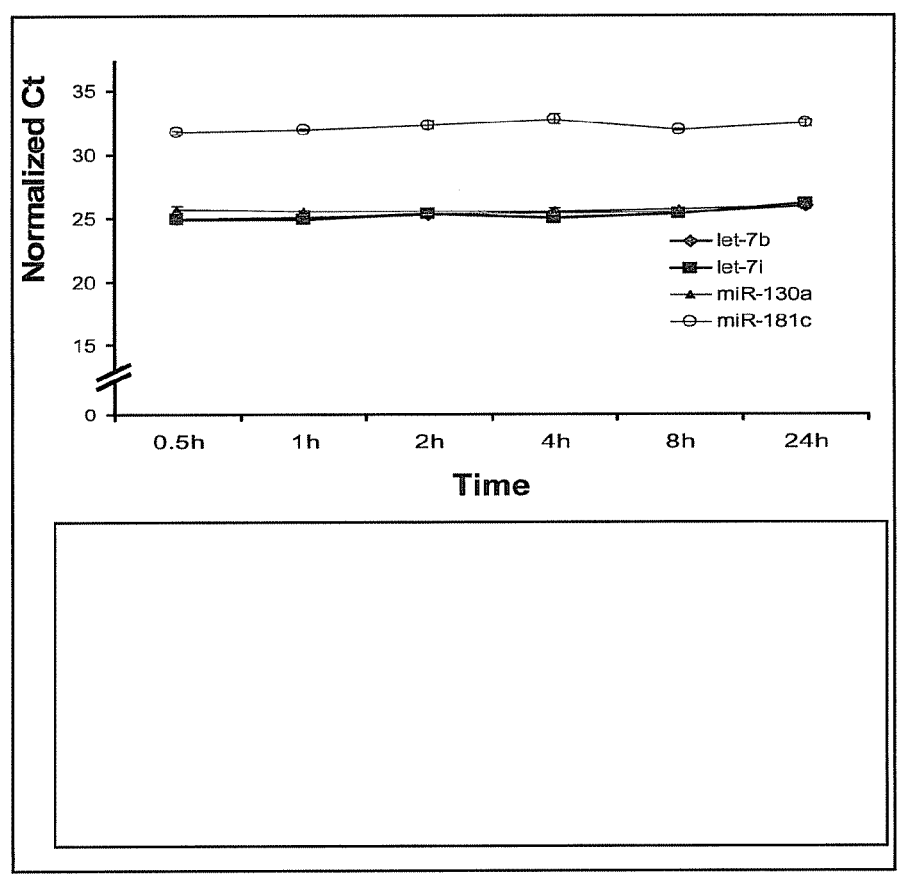
FIG. 21. Stability of miRNAs in room temperature for number of time points. 300 μl of sera from a healthy woman was thawed on ice and lysed with an equal volume of 2× Denaturing Solution (Ambion). RNA was isolated spiked sera using the mirVana PARIS kit following the manufacturer's protocol for liquid samples (Ambion). RNA was eluted with 50 μl of nuclease-free water. This experiment was performed in triplicates.

Second, we wanted to know whether our lab conditions such as temperature and freezing and thawing affect the stability of miRNAs. We selected a serum sample from healthy woman, and incubated in room temperature for a series of time points (spiked three exogenous miRNAs as external controls) (FIG. 21). As expected, the selected miRNAs were very stable throughout the experiment. This observation is in consistent with the literature (Mitchell et al., 2008, Proc. Natl. Acad. Sci. U.S.A 105:10513-8).

Figure 22:
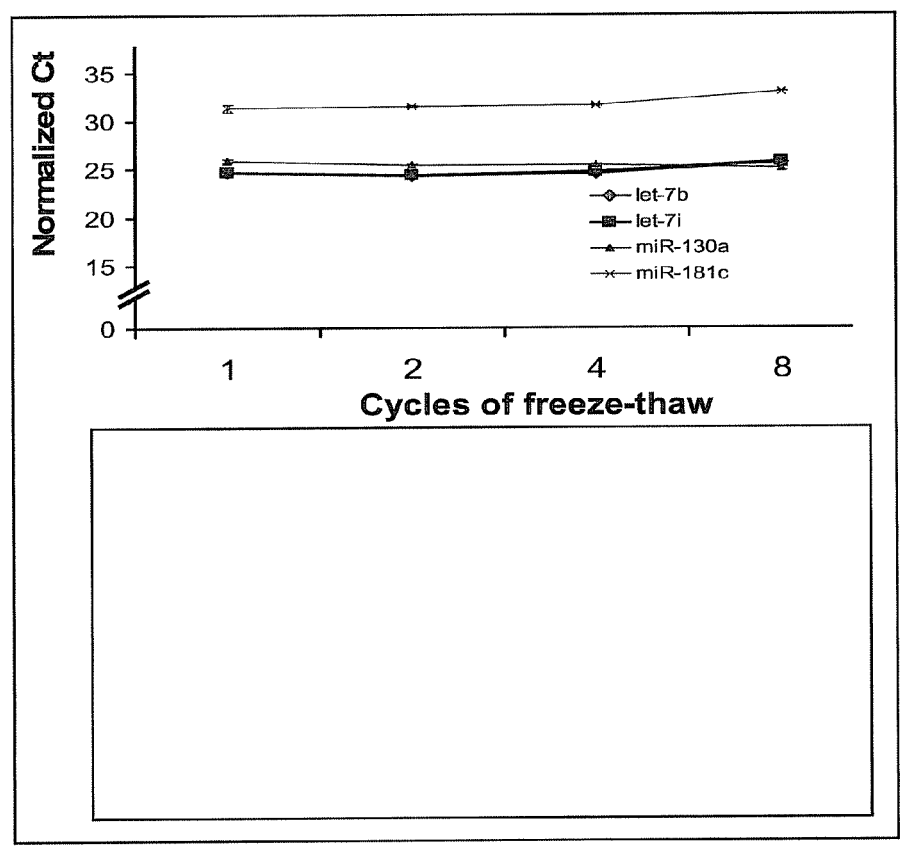
FIG. 22. Stability of miRNAs in freeze/thaws. 300 μl of sera from a healthy woman was thawed on ice, exogenous miRNAs were spiked in, and then performed freeze/thaw cycles for the indicated times, then lysed with an equal volume of 2× Denaturing Solution (Ambion). RNA was isolated spiked sera using the mirVana PARIS kit following the manufacturer's protocol for liquid samples (Ambion). RNA was eluted with 50 μl of nuclease-free water. This experiment was performed in triplicates.

Third, we tested whether frequent freeze/thaw affects stability of miRNAs. We performed the freeze/thaw for the spiked serum sample for up to eight times, and RNA was extracted from it and used for analysis of the selected miRNAs (i.e. let-7b/7i, miR-181c and miR-130a) (FIG. 22). As expected, these miRNAs show relatively stable in repeated freeze/thaws for eight times. This also agrees with the literature (Mitchell et al., 2008, Proc. Natl. Acad. Sci. U.S.A 105: 10513-8).

Figure 23:
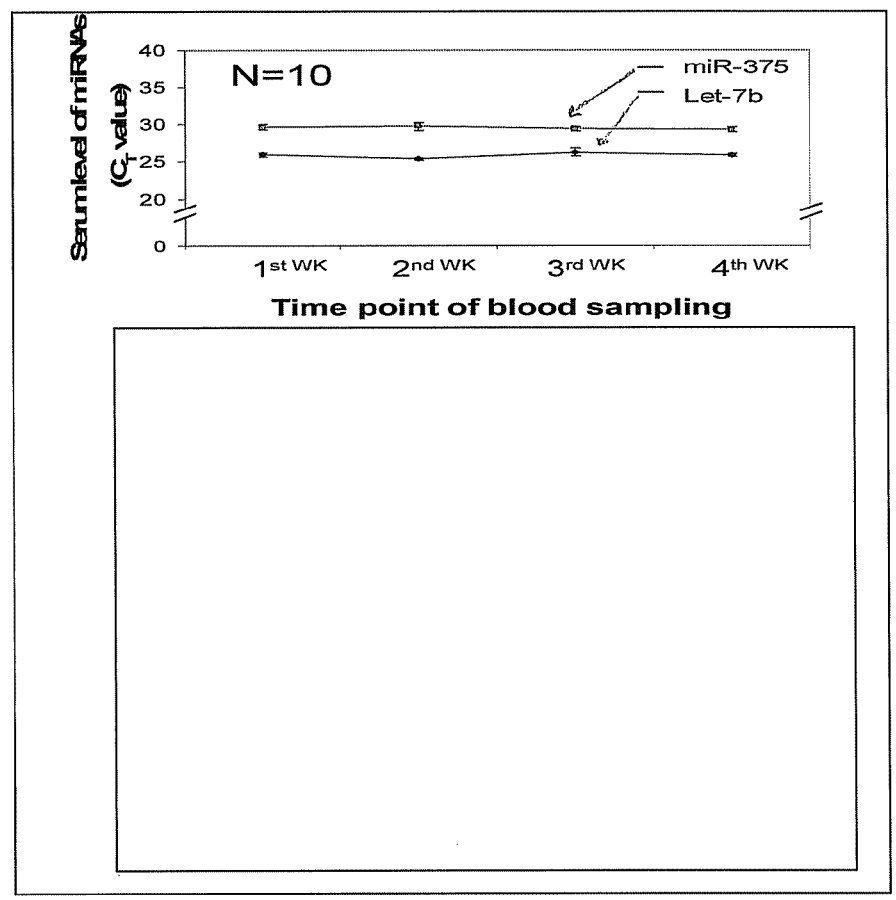
FIG. 23. Dynamic changes of miRNAs in a women's menstrual cycle. Blood sampling was occurred every week for one month from ten healthy Asian women (no history of bearing child) with age range of 22-24 year-old. Total RNA was extracted from 300 ul of serum. miRNAs (let-7b and miR-375) were analyzed by using qRT-PCR. Data were analyzed by one-way ANOVA, indicating that no significant changes of two miRNAs tested were observed during the women's menstrual cycle. All measurements were performed three times.

Fourth, we tested sera for the endogenous level of the selected miRNAs in the stages of women's menstrual cycle. We recruited ten healthy non-pregnant Asian women rageing in age between 22-24 years. Blood draw was performed four times in a month with 10 ml each time. RNA was extracted from sera with the spiked external miRNAs (see above) standard, and used for analysis of the selected miRNAs (tumor suppressor let-7b and oncogenic miR-375) (FIG. 23). The levels of these two miRNAs were not affected by menstrual cycle, suggesting that these miRNAs are relatively stable and may not be affected by women's physiological cycle changes. This is the first report showing that miRNAs may be stable during the women's menstrual cycle condition.

Figure 24:
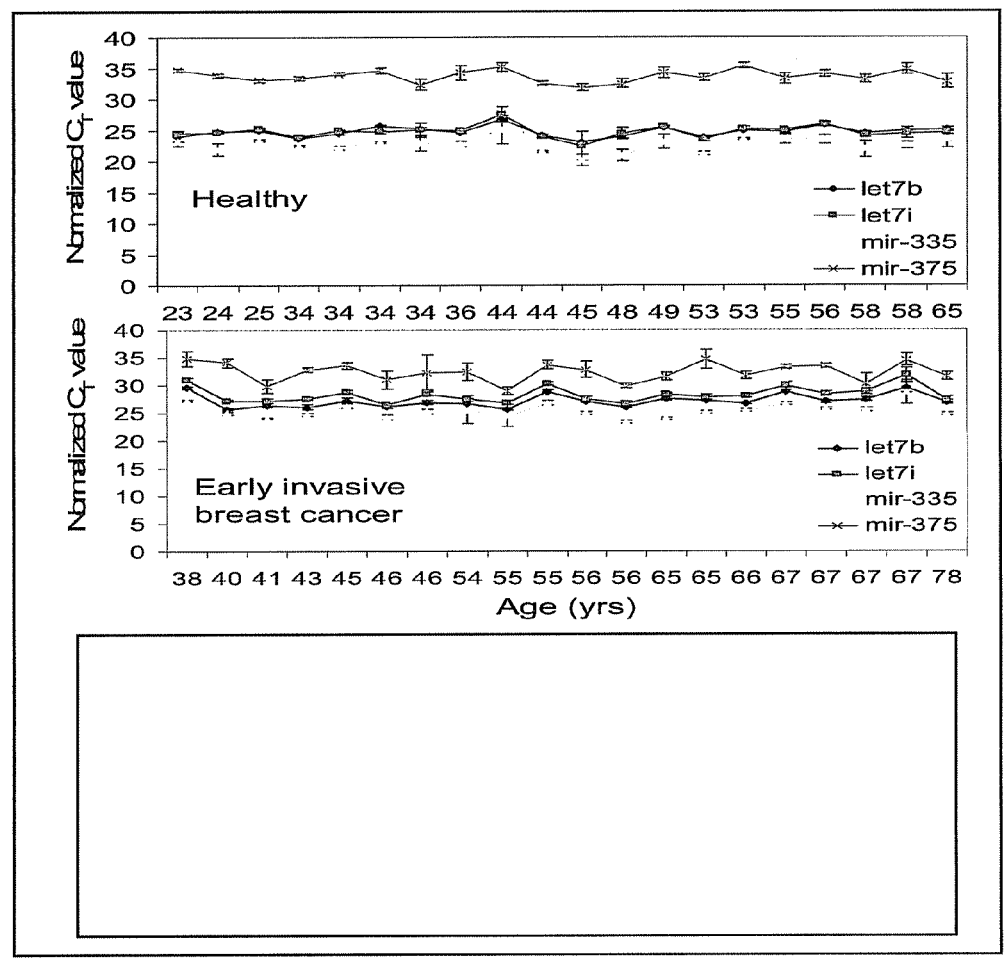
FIG. 24. Age/menopausal status on the circulating miRNAs. Serum samples were collected from 20 healthy women or 20 women with breast cancer at early invasive carcinoma. Total RNA was extracted from 300 ul of serum. miRNAs (let-7b/i and miR-335/miR-375) were analyzed by using qRT-PCR. Data were analyzed by one-way ANOVA, indicating that no significant changes of four miRNAs tested were observed at each disease status. All measurements were performed three times.

Fifth, to find out whether age or menopausal status affects the stability of miRNAs, we selected 20 serum samples from healthy women in the age range of 23-65, and 20 serum samples from women with breast cancer at early invasive carcinoma in the age range of 38-78. RNA was extracted from pre-spiked sera and used for analysis of the selected miRNAs (let-7b/7i, miR-335 and miR-375) (FIG. 24). We found that age or menopausal status doesn't affect level of miRNAs significantly among individuals in each group (regardless healthy group or cancer group) (FIG. 24).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of treating breast cancer in a subject in need thereof, the method comprising:
    identifying breast cancer cells associated with the subject that are resistant to a selective estrogen receptor modulator (SERM); and
    thereafter administering to the subject a polynucleotide in an amount effective to increase tamoxifen sensitivity of the breast cancer cells, wherein the polynucleotide is a single strand miRNA substantially complementary to 5'-AACACCAGGAAGGCCUACCUCA (SEQ ID NO: 16).

2. The method of claim 1 wherein the breast cancer cells are identified as being ER-α66 positive prior to administration of the polynucleotide.

3. The method of claim 1 further comprising administering a selective estrogen receptor modulator (SERM).

4. The method of claim 1 wherein between 12 and 17 nucleotides of the polynucleotide are complementary to 5'-AACACCAGGAAGGCCUACCUCA (SEQ ID NO:16).

5. The method of claim 3 wherein the SERM is tamoxifen.

6. The method of claim 1 wherein the breast cancer cells are identified as ER-α66 negative, progesterone receptor negative, and Human Epidermal growth factor Receptor 2 negative before the polynucleotide is administered to the subject.

7. The method of claim 1 wherein the breast cancer cells are identified as ER-α66 negative, ER-α36 positive, progesterone receptor negative, and Human Epidermal growth factor Receptor 2 positive before the polynucleotide is administered to the subject.

8. The method of claim 1 wherein the SERM is tamoxifen.

9. The method of claim 1 wherein the step of identifying comprises obtaining breast cancer cells by biopsy from the subject.

10. The method of claim 1 further comprising administration of a therapeutic compound.

11. The method of claim 10 wherein the therapeutic compound is selected from an anti-cancer agent, a chemotherapeutic agent, and a radiotherapeutic agent.

12. A method of reducing expression of ER-α36 and/or ER-α66 in a subject having breast cancer or at risk of developing breast cancer, the method comprising:
    obtaining a biological sample from the subject;
    determining a baseline level of expression of ER-α36 and/or ER-α66 in a biological sample;
    thereafter administering to the subject a polynucleotide in an amount effective to reduce expression of ER-α36 and/or ER-α66 in the subject by at least 20% compared to the baseline level of expression, wherein the polynucleotide is a single stranded miRNA and is substantially complementary to SEQ ID NO: 16.

13. The method of claim 12 wherein between 12 and 17 nucleotides of the polynucleotide are complementary to SEQ ID NO:16.

14. The method of claim 12 wherein the expression of ER-α36 and/or ER-α66 is reduced in the subject by at least 30% compared to the baseline level of expression.

15. The method of claim 12 further comprising administering to the subject a SERM.

16. The method of claim 15 wherein the SERM is tamoxifen.

17. A method of treating breast cancer in a subject in need thereof, the method comprising:
   identifying breast cancer cells associated with the subject that are resistant to a selective estrogen receptor modulator (SERM); and
   thereafter administering to the subject a single strand miRNA in an amount effective to increase tamoxifen sensitivity of the breast cancer cells,
   wherein the single strand miRNA has at least 80% sequence identity to 3'-UUGAUAUGUUG-GAUGAUGGAGU-5' (SEQ ID NO:7) and down-regulates ER-α36 expression.

* * * * *